United States Patent
Shirai et al.

(10) Patent No.: US 9,389,289 B2
(45) Date of Patent: Jul. 12, 2016

(54) MAGNETIC RESONANCE IMAGING DEVICE

(75) Inventors: Toru Shirai, Hachioji (JP); Yoshitaka Bito, Kokubunji (JP); Satoshi Hirata, Kodaira (JP); Yoshihisa Soutome, Tokyo (JP); Yo Taniguchi, Kokubunji (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 720 days.

(21) Appl. No.: 13/881,739

(22) PCT Filed: Oct. 26, 2011

(86) PCT No.: PCT/JP2011/074706
§ 371 (c)(1),
(2), (4) Date: Apr. 26, 2013

(87) PCT Pub. No.: WO2012/057222
PCT Pub. Date: May 3, 2012

(65) Prior Publication Data
US 2013/0214785 A1    Aug. 22, 2013

(30) Foreign Application Priority Data

Oct. 28, 2010  (JP) .................................. 2010-242585
Aug. 25, 2011  (JP) .................................. 2011-184160

(51) Int. Cl.
*G01R 33/36*    (2006.01)
*A61B 5/055*    (2006.01)
(Continued)

(52) U.S. Cl.
CPC ............ *G01R 33/3621* (2013.01); *A61B 5/055* (2013.01); *G01R 33/465* (2013.01); *G01R 33/485* (2013.01); *G01R 33/4828* (2013.01); *G01R 33/5611* (2013.01)

(58) Field of Classification Search
CPC ............ G01R 33/465; G01R 33/3621; G01R 33/4828; G01R 33/5611; G01R 33/485; A61B 5/055
See application file for complete search history.

(56) References Cited

U.S. PATENT DOCUMENTS

2014/0002083 A1*  1/2014  Asaba .................... G01R 33/32
                                        324/318
2014/0253123 A9*  9/2014  Asaba .................... G01R 33/32
                                        324/318

FOREIGN PATENT DOCUMENTS

JP    60-168041       8/1985
JP    2007-202903     8/2007
(Continued)

OTHER PUBLICATIONS

Uwe Klose, In vivo proton spectroscopy in presence of eddy currents, Magnetic Resonance in Medicine, 1990, pp. 26-30, vol. 14.
(Continued)

*Primary Examiner* — Dixomara Vargas
(74) *Attorney, Agent, or Firm* — Baker Botts L.L.P.

(57) ABSTRACT

Images of two or more kinds of substances showing different chemical shifts, such as water image and metabolite image, are obtained without extending measurement time. For example, images of two or more kinds of desired substances showing different chemical shifts, such as water image and metabolite image, are obtained by one time of execution of an imaging sequence. In this execution, a pre-pulse is applied so that signals of the substances to be separated shift on the image, and magnetic resonance signals are received with receiver RF coils in a number not smaller than the number of types of the substances to be separated. An image reconstructed from the magnetic resonance signals is separated into images of the individual substances using sensitivity maps of the receiver RF coils. Then, correction is performed for returning the shifted image to the original position. Further, residual signals induced by errors generated in the measurement and the separation processing are eliminated by using spectroscopic images obtained after the separation.

15 Claims, 31 Drawing Sheets

(51) Int. Cl.
*G01R 33/465* (2006.01)
*G01R 33/48* (2006.01)
*G01R 33/485* (2006.01)
*G01R 33/561* (2006.01)

(56) References Cited

FOREIGN PATENT DOCUMENTS

| JP | 2008-264306 | 11/2008 |
|---|---|---|
| WO | WO 2008/087822 A1 | 7/2008 |
| WO | WO 2009/057353 A1 | 5/2009 |
| WO | WO 2010/116782 A1 | 10/2010 |

OTHER PUBLICATIONS

J.C. Hindman, Proton Resonance shift of Water in the Gas and Liquid States, The Journal of Chemical Physics, Jun. 15, 1996, pp. 4582-4592, vol. 44, No. 12.

Ernest B. Cady, et al., "The Estimation of Local Brain Temperature by In Vivo $^1H$ Magnetic Resonance Spectroscopy", Magnetic Resonance in Medicine, 1995, pp. 862-867, vol. 33.

\* cited by examiner

100

101

102

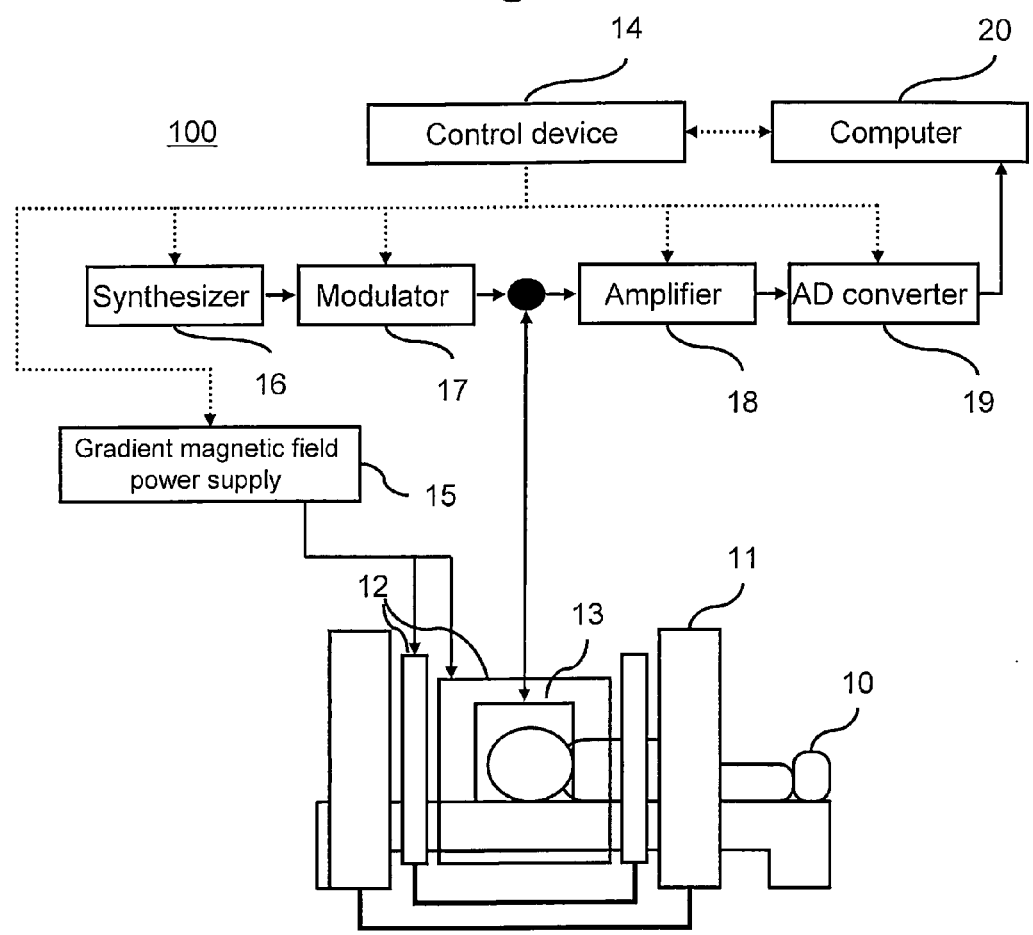

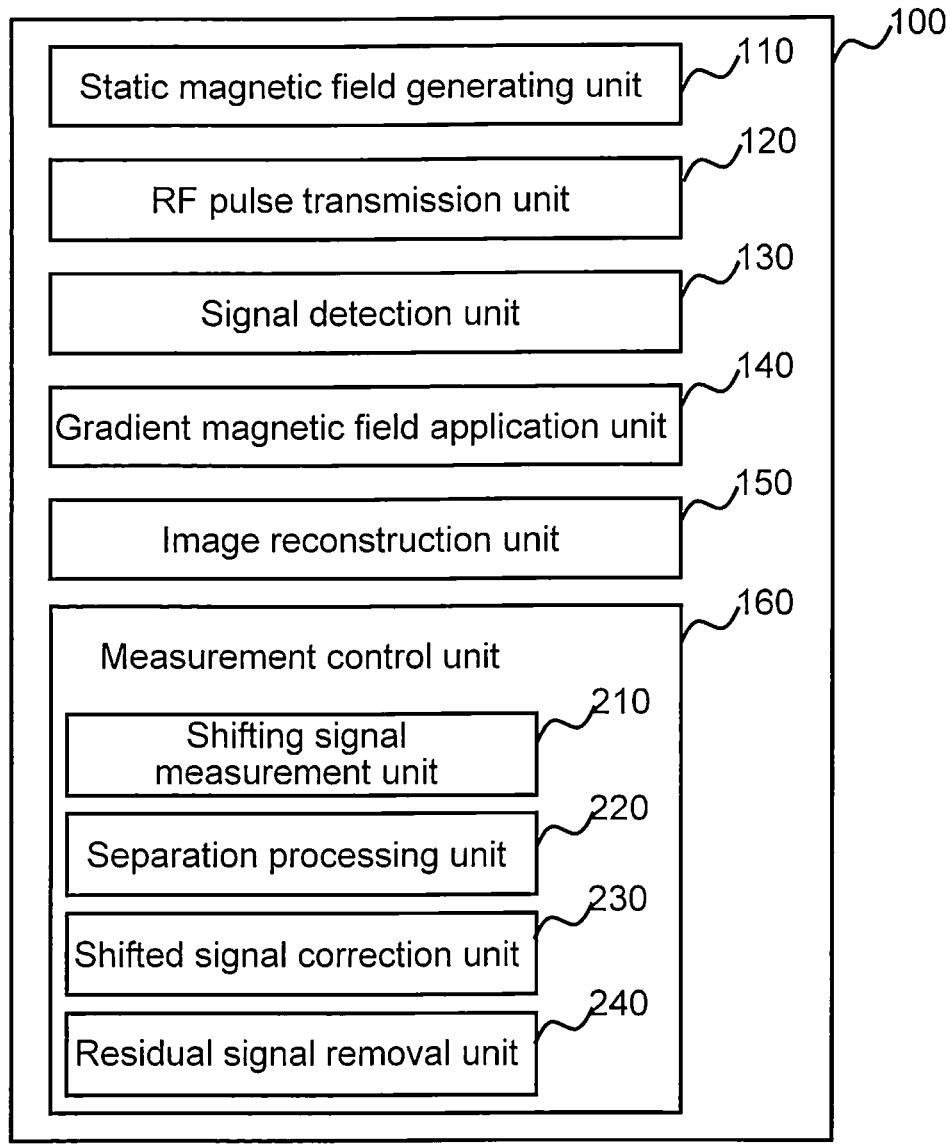

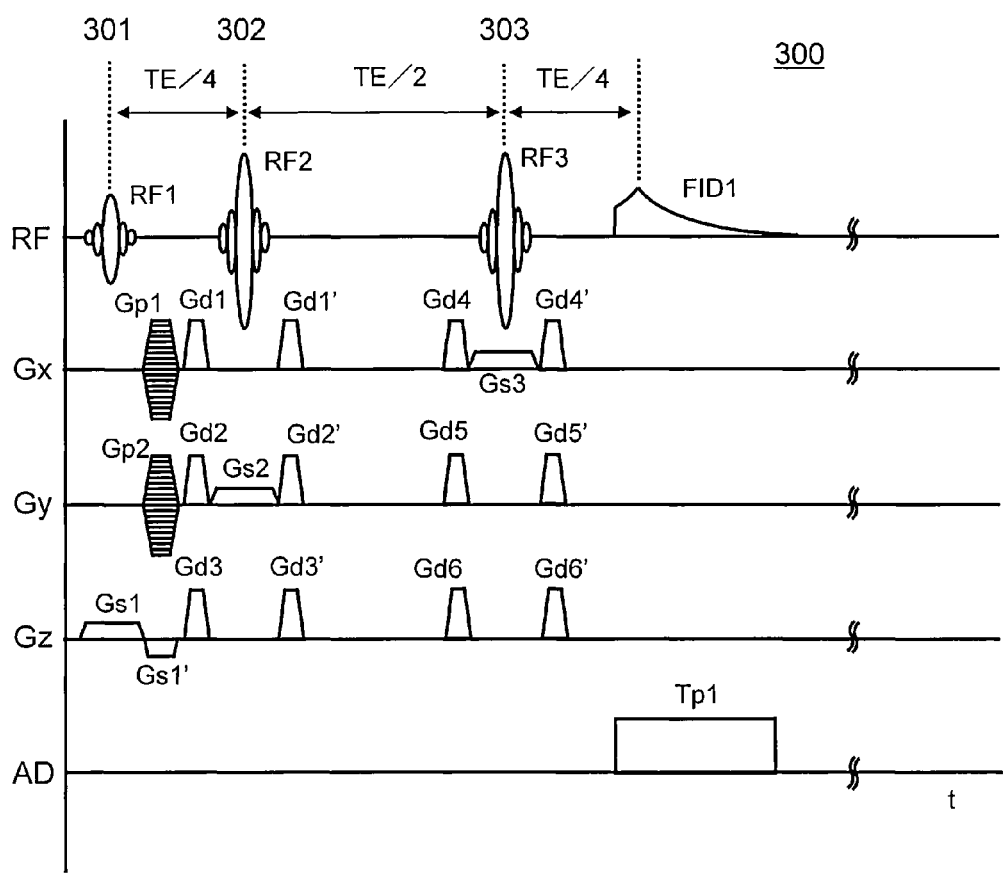

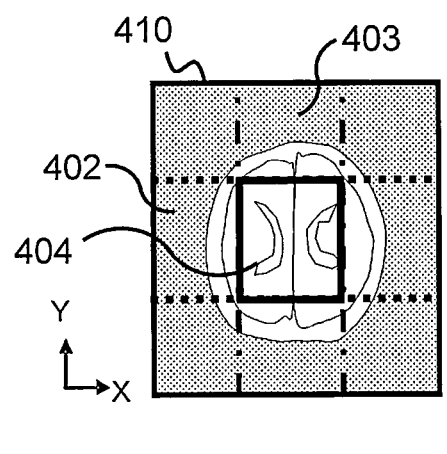
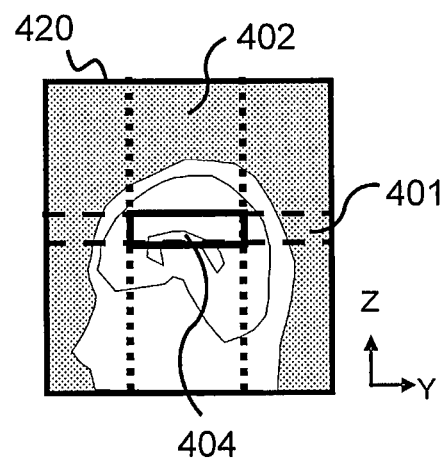
*Fig. 6A* *Fig. 6B*
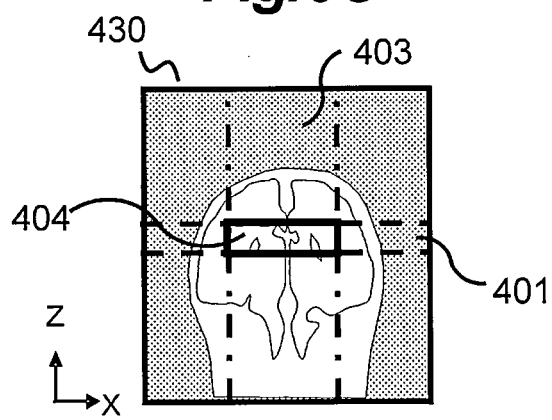
*Fig. 6C*

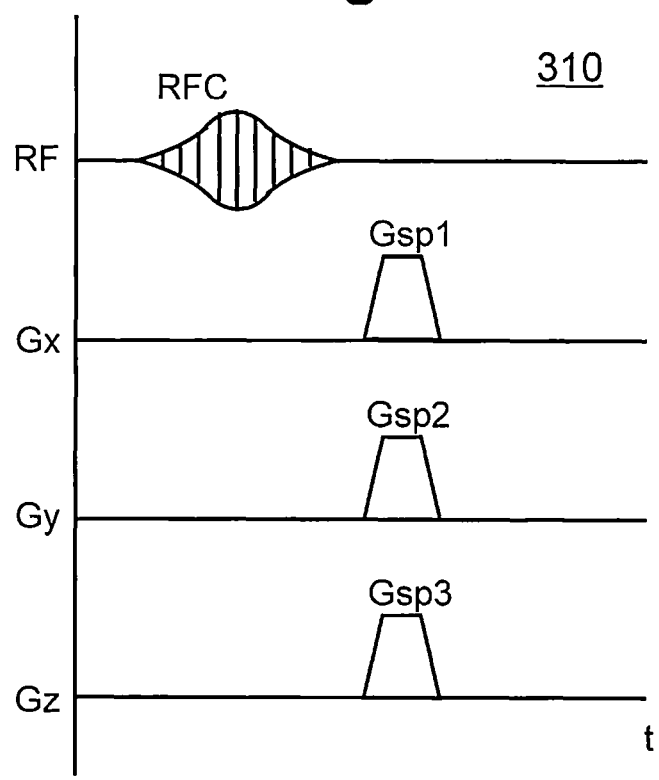

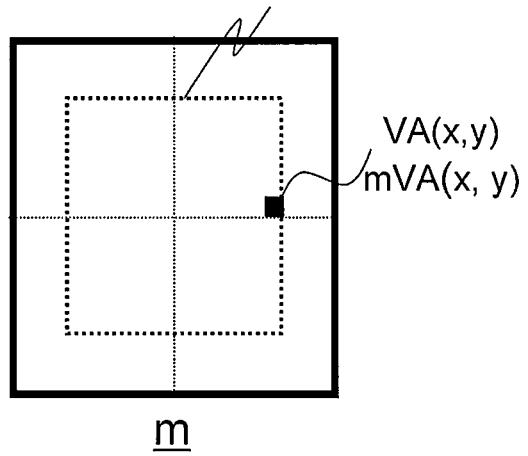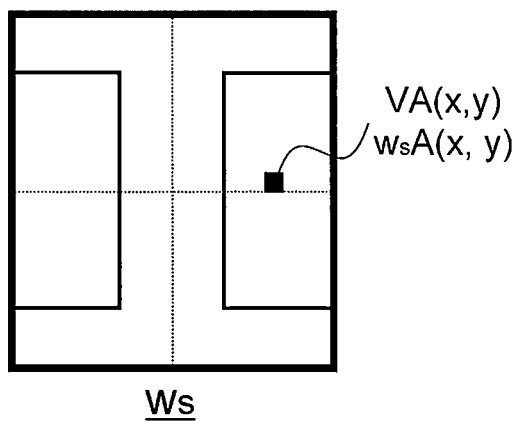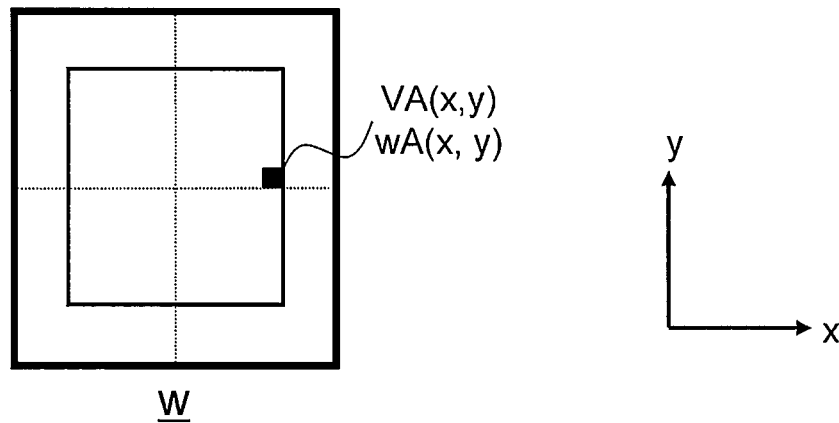

Cm

Cw

Fig.23A
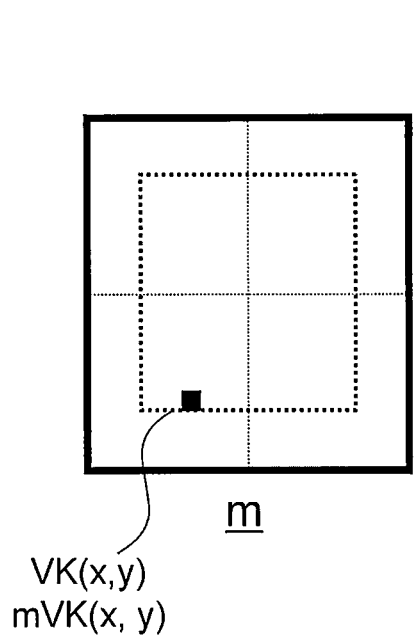
m
VK(x,y)
mVK(x, y)
Fig.23B
VL(x, y+N2/2)
wsVL(x, y+N2/2)
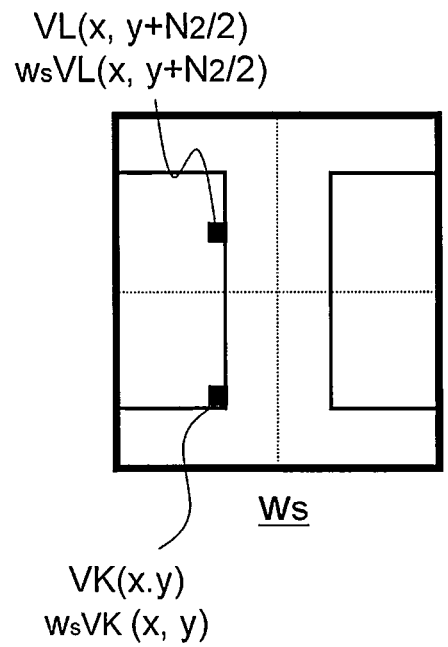
ws
VK(x.y)
wsVK (x, y)
Fig.23C
VL(x, y+N2/2)
wVL(x, y+N2/2)
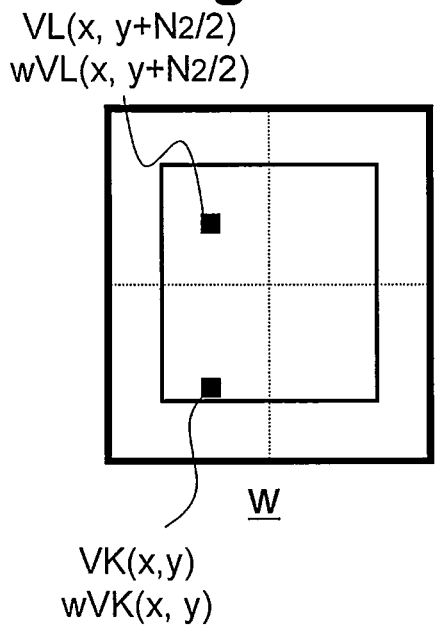
w
VK(x,y)
wVK(x, y)
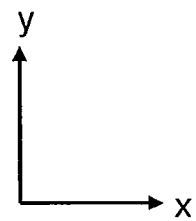

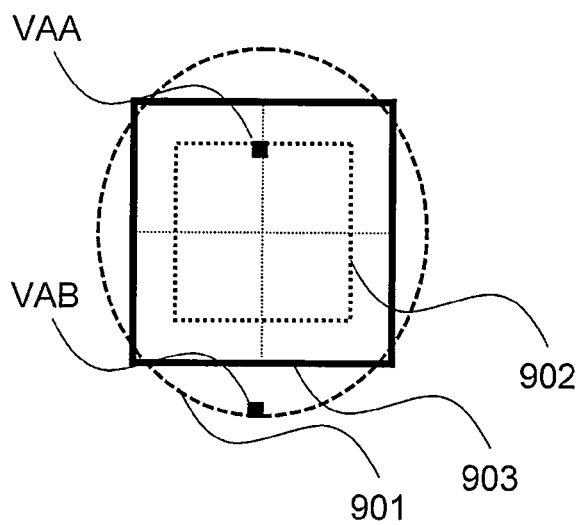
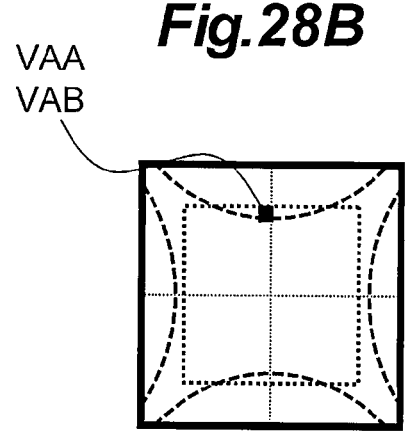
*Fig.28A*  *Fig.28B*
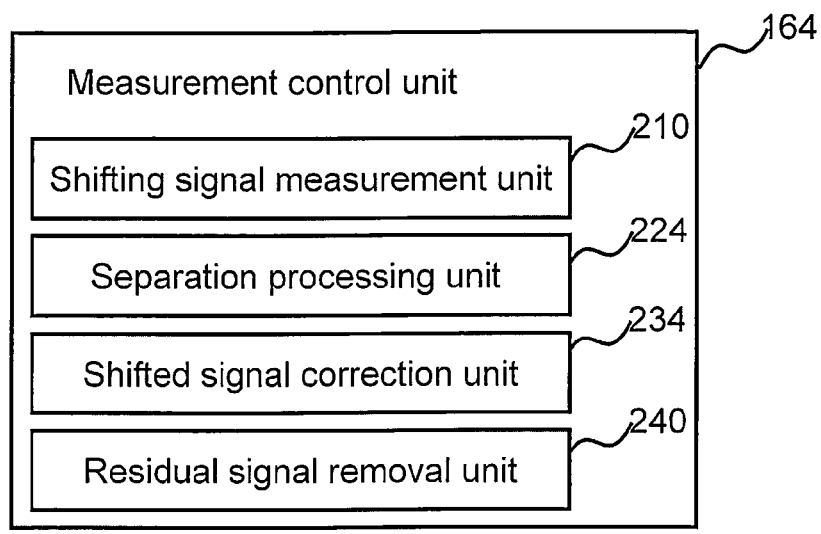
*Fig. 29*

Cm

Cm1

Cw1

Cw

MAGNETIC RESONANCE IMAGING DEVICE

TECHNICAL FIELD

The present invention relates to a technique for magnetic resonance imaging. In particular, the present invention relates to a technique for MRSI (Magnetic Resonance Spectroscopic Imaging), which images a spatial signal intensity distribution of every metabolite.

BACKGROUND ART

Magnetic resonance imaging (MRI) apparatuses are apparatuses for irradiating a radio frequency magnetic field of a specific frequency on an object of measurement placed in a static magnetic field to induce magnetic resonance phenomenon and thereby obtain physical and chemical information of the object of measurement. The magnetic resonance imaging (MRI) method currently widely spreading is a method of imaging hydrogen nucleus density, difference of relaxation time, or the like, which differs depending on type of body tissue, by mainly using magnetic resonance phenomenon of protons in water molecules. Difference of tissues can be thereby imaged, and thus it is highly effective for diagnosis of diseases.

On the other hand, magnetic resonance spectroscopy (MRS) and magnetic resonance spectroscopic imaging (MRSI) are methods of separating magnetic resonance signals for every molecule on the basis of difference in resonance frequency (chemical shift) caused by difference of chemical bonds in the molecules (metabolites), and measuring density, relaxation time, or the like for every molecular species. MRS is a method of observing molecular species in a certain selected special region, and MRSI is a method of imaging every molecular species. The atomic nuclei used as the object include those of $^{31}$H (proton), $^{31}$P, $^{13}$C, $^{17}$F, and so forth.

Major metabolites existing in human bodies and detectable by proton MRS or proton MRSI (henceforth referred to simply as MRS/MRSI) utilizing protons as the objective nucleus species include choline, creatine, N-acetylaspartic acid (NAA), lactic acid, and so forth. It is expected to perform non-invasive stage determination or early diagnosis, and diagnosis of malignancy of metabolic disorders such as cancers, on the basis of amounts of such metabolites.

Since such metabolites existing in human bodies show signal intensity corresponding to only about $^1\!/_{1000}$ of that of water molecules, weak signals from the metabolites are buried in the foot of the gigantic peak signal generated by water, and detection of metabolite signals is difficult. Therefore, there are methods of suppressing water signals in order to measure signals from metabolites. For example, there is a method of preliminarily suppressing water signals by using a radio frequency (RF) pulse having a frequency band similar to the frequency band of water signals, and detecting marginal signals of metabolites (refer to, for example, Patent document 1). The method of suppressing signals by pseudo saturation around the resonance frequency band of unnecessary signals is called CHESS (CHEmical shift Selective) method.

As described above, in order to measure metabolites, it is necessary to suppress water signals. However, measuring not only metabolite signals, but also water signals provides the following advantages.

(1) Correction of eddy current-induced distortion using phase of water signals:

By eddy currents generated at the time of application of the gradient magnetic field, phases of metabolite signals are changed and metabolite peaks are distorted. In order to correct such peak distortion due to the phase change, the phases are corrected by using water signals showing signal intensity higher than that of metabolite signals (refer to, for example, Non-patent document 1). The phase distortion is corrected by this correction of eddy current-induced distortion, and thus favorable metabolite peaks can be obtained.

(2) In vivo temperature measurement using resonance frequency of water:

The resonance frequency of water shifts depending on temperature, and the shift amount is represented with a temperature coefficient of −0.01 ppm/° C. On the other hand, it is known that the resonance frequencies of metabolites such as NAA do not change in the in vivo temperature range (refer to, for example, Non-patent document 2). It has been reported that in vivo temperature measurement is possible from frequency difference between water and metabolite by using the aforementioned characteristics (refer to, for example, Non-patent document 3). It is expected that in vivo temperature measurement may provide novel indexes for identification of ischemic region in chronic stage cerebral infarction, distinction of ischemic center and circumference region in acute stage cerebral infarction, and differentiation of tumor cytoma.

PRIOR ART REFERENCES

Patent Document

Patent document 1: Japanese Patent Unexamined Publication (KOKAI) No. 60-168041

Non-Patent Documents

Non-patent document 1: Klose U. et al., "In vivo proton spectroscopy in presence of eddy currents", Magnetic Resonance in Medicine, 1990, vol. 14, pp. 26-30

Non-patent document 2: Hindman J. C., "Proton Resonance shift of Water in the Gas and Liquid States", The Journal Of Chemical Physics, 1996, vol. 44, pp. 4582-4592

Non-patent document 3: Cady E. B. et al., "The Estimation of Local Brain Temperature by In Vivo 1H Magnetic Resonance Spectroscopy", Magnetic Resonance in Medicine, 1995, vol. 33, pp. 862-867

DISCLOSURE OF THE INVENTION

Object to be Achieved by the Invention

As described above, it is desired to obtain not only metabolite signals but also water signals in the MRS/MRSI measurement for correction of eddy current-induced distortion and in vivo temperature measurement. However, in order to obtain both water signals and metabolite signals, it is necessary to perform both metabolite signal measurement with suppressing water signals and water signal measurement without suppressing water signals. In MRSI, in particular, water images in the same matrix number as that of metabolite images must be obtained, and therefore actual measurement time is markedly increased.

The above situation is not limited to water and a metabolite, and also applies to two or more kinds of substances showing different resonance frequencies, and it is desired to separately obtain images of two or more kinds of substances without extending measurement time with eliminating influence on signals of a certain kind of substance by the other one or more kinds of substances among such two or more kinds of substances.

The present invention was accomplished in light of the aforementioned circumstance, and an object of the present invention is to provide a technique for obtaining images of two or more kinds of substances showing different chemical shifts, such as water image and metabolite image, without extending measurement time.

Means for Achieving the Object

According to the present invention, images of two or more kinds of substances showing different chemical shifts, such as water image and metabolite image, are obtained by one time of execution of an imaging sequence. In this imaging, measurement is performed by applying a pre-pulse so that signals of the substances to be separated shift on the image, and the magnetic resonance signals are received with receiver RF coils in a number not smaller than the number of types of the substances to be separated. An image reconstructed from the magnetic resonance signals is separated into images of the individual substances using sensitivity maps of the receiver RF coils. Then, correction is performed for returning the shifted image to the original position. Further, residual signals induced by errors generated in the measurement and the separation processing are eliminated by using spectroscopic images obtained after the separation.

Specifically, there is provided a magnetic resonance imaging apparatus comprising a static magnetic field generating unit which generates a static magnetic field in a space in which a subject is placed, a transmission unit which transmits a radio frequency magnetic field pulse to the subject, a reception unit which receives magnetic resonance signals generated from the subject, a gradient magnetic field application unit which applies a phase encoding gradient magnetic field for adding positional information to the magnetic resonance signals, an image reconstruction unit which reconstructs an image from the magnetic resonance signals received by the reception unit, and a measurement control unit which controls operations of the transmission unit, the reception unit, the gradient magnetic field application unit, and the image reconstruction unit to obtain a measured image, wherein the reception unit comprises receiver RF coils in a number not smaller than number of kinds of two or more kinds of substances as objects of measurement, and arranges the received magnetic resonance signals in a different k-space for every receiver RF coil, and the measurement control unit comprises a shifting signal measurement unit which obtains a measured image for every receiver RF coil with spatially shifting signals of substances as objects of measurement on the image by different amounts of shift, a separation unit which separates measured images obtained with the shifting signal measurement unit into measured images of two or more kinds of the substances by using sensitivity maps of the receiver RF coils, and a shifted signal correction unit which corrects the shift amounts in the measured images for the substances obtained after the separation with the separation unit.

Effect of the Invention

According to the present invention, images of two or more kinds of substances showing different chemical shifts, such as a water image and metabolite image, can be obtained without extending measurement time.

BRIEF DESCRIPTION OF THE DRAWINGS

FIG. 2 is a schematic configurational diagram of the magnetic resonance imaging apparatus (MRI apparatus) according to the first embodiment.

FIG. 3 is a functional block diagram of the MRI apparatus according to the first embodiment.

FIG. 5 is a sequence diagram of the main scan pulse sequence according to the first embodiment.

FIG. 6A is an explanatory diagram for explaining an example of region excited with the main scan pulse sequence according to the first embodiment.

FIG. 6B is an explanatory diagram for explaining an example of region excited with the main scan pulse sequence according to the first embodiment.

FIG. 6C is an explanatory diagram for explaining an example of region excited with the main scan pulse sequence according to the first embodiment.

FIG. 7 is an explanatory diagram for explaining an example of pre-pulse sequence according to the first embodiment.

FIG. 12A is an explanatory diagram for explaining water signal remaining in the metabolite spectroscopic image measured according to the first embodiment, which shows a metabolite spectroscopic image.

FIG. 12B is an explanatory diagram for explaining water signal remaining in the metabolite spectroscopic image measured according to the first embodiment, which shows shifted water spectroscopic image.

FIG. 12C is an explanatory diagram for explaining water signal remaining in the metabolite spectroscopic image measured according to the first embodiment, which shows a water spectroscopic image.

FIG. 23A is an explanatory diagram for explaining water signal remaining in a metabolite spectroscopic image measured according to the second embodiment, which shows the metabolite spectroscopic image.

FIG. 23B is an explanatory diagram for explaining water signal remaining in a metabolite spectroscopic image measured according to the second embodiment, which shows a shifted water spectroscopic image.

FIG. 23C is an explanatory diagram for explaining water signal remaining in a metabolite spectroscopic image measured according to the second embodiment, which shows a water spectroscopic image.

FIG. 28A is an explanatory view for explaining aliasing phenomenon.

FIG. 28B is an explanatory view for explaining aliasing phenomenon.

FIG. 29 is a functional block diagram of the measurement control unit according to the fourth embodiment.

MODES FOR CARRYING OUT THE INVENTION

First Embodiment

Hereafter, the first embodiment of the present invention will be explained with reference to the drawings. This embodiment will be explained below by exemplifying a case where two-dimensional water image and metabolite image are obtained simultaneously.

Figure 1A:
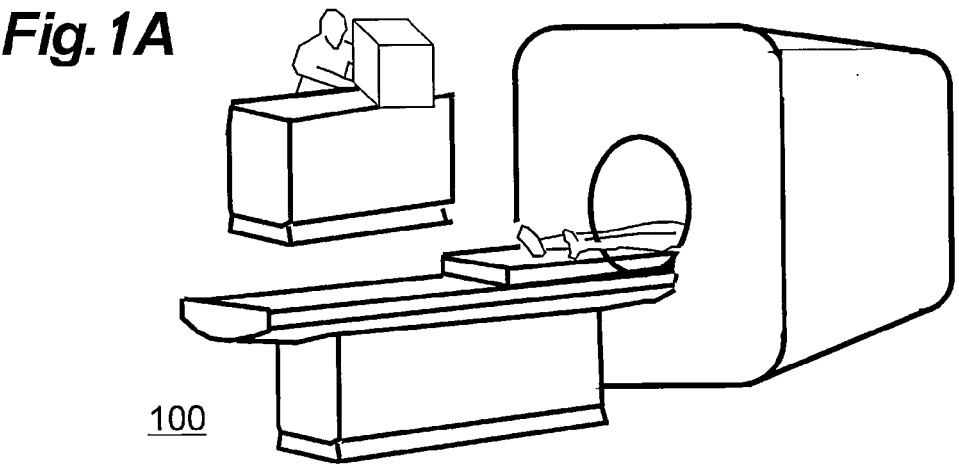
FIG. 1A is an exterior view of a magnetic resonance imaging apparatus according to the first embodiment.
Figure 1B:
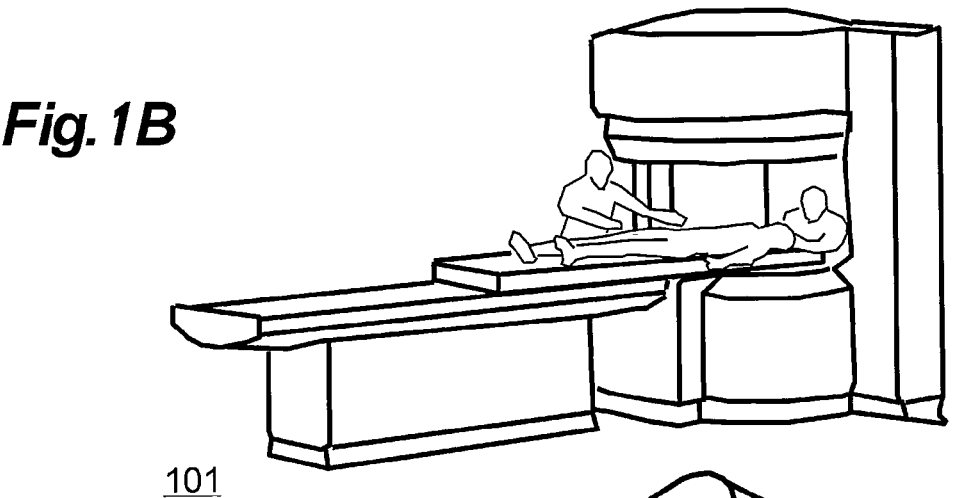
FIG. 1B is an exterior view of another magnetic resonance imaging apparatus according to the first embodiment.
Figure 1C:
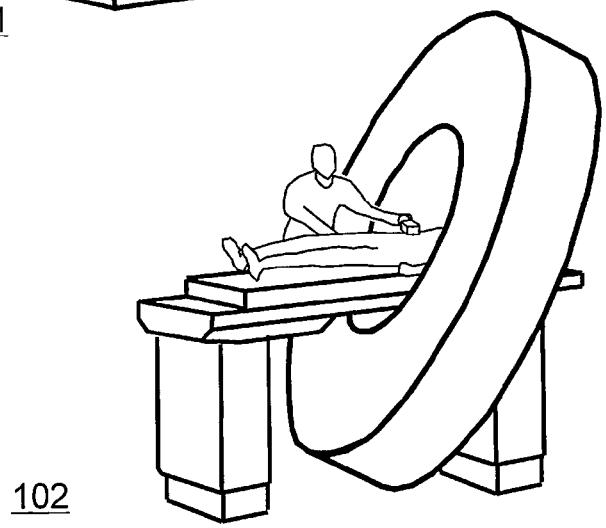
FIG. 1C is an exterior view of still another magnetic resonance imaging apparatus according to the first embodiment.

First, magnetic resonance imaging apparatuses (MRI apparatuses) according to this embodiment will be explained. FIGS. 1A to 1C are exterior views of MRI apparatuses according to this embodiment. FIG. 1A shows an MRI apparatus 100 of the horizontal magnetic field type utilizing a tunnel-shaped magnet that generates a static magnetic field with a solenoid coil. FIG. 1B shows an MRI apparatus 101 of the vertical magnetic field type utilizing a hamburger type (open type) magnet having separated upper and lower magnets, which are used for increasing spaciousness. Further, FIG. 1C shows a tunnel type MRI apparatus 102 similar to that of FIG. 1A, but depth of the magnet is shortened and the magnet is leaned to increase spaciousness. For this embodiment, any of MRI apparatuses having these exterior views can be used. These are mere examples, and the MRI apparatus according to this embodiment is not limited to these apparatuses. For this embodiment, various kinds of known MRI apparatuses can be used for this embodiment regardless of form or type thereof.

Hereafter, this embodiment will be explained by exemplifying a case of using the MRI apparatus 100 of the horizontal magnetic field type. There is used a coordinate system of which Z-direction is the static magnetic field direction, and among two directions perpendicular to the static magnetic field direction, one parallel to the bed surface on which a subject as an object of measurement is placed is the x-direction, and one perpendicular to the foregoing directions is the y-direction.

First, the apparatus configuration of the MRI apparatus of this embodiment will be explained. FIG. 2 is a configurational functional diagram of the MRI apparatus 100 according to this embodiment. As shown in this drawing, the MRI apparatus 100 according to this embodiment is provided with a static magnetic field generating magnet 11, a gradient magnetic field generating coil 12, a radio frequency magnetic field coil system 13, a control device 14, a gradient magnetic field power supply 15, a synthesizer 16, a modulator 17, an amplifier 18, an AD converter 19, and a computer 20.

The synthesizer 16 generates radio frequency waves, the modulator 17 performs waveform shaping and power amplification of the radio frequency waves generated by the synthesizer 16, and supplies an electric current to the radio frequency magnetic field coil system 13. The radio frequency magnetic field coil system 13 generates a radio frequency magnetic field for exciting nuclear spins of the object of measurement (subject) 10 (excitation pulse, RF pulse) with the supplied electric current, and irradiates it on the object of measurement 10.

The gradient magnetic field power supply 15 supplies an electric current to the gradient magnetic field generating coil 12, and the gradient magnetic field generating coil 12 supplied with the electric current generates a gradient magnetic field, and modulates radio frequency signals, which are magnetic resonance signals, from the object of measurement 10 according to spatial positions.

The radio frequency magnetic field coil system 13 receives (detects) the modulated radio frequency signals. The amplifier 18 amplifies the radio frequency signals received by the radio frequency magnetic field coil system 3. The AD converter 19 performs A/D conversion of the amplified radio frequency signals, and inputs them into the computer 20.

The control device 14 operates the components according to directions from the computer 20.

The computer 20 performs data processing of the inputted signals and saves them, and it controls the units so that they operate according to a time chart stored beforehand. The computer 20 is provided with CPU, a memory and a storage device, and it loads programs stored in the storage device beforehand to the memory, and executes them to realize various kinds of operation processings and control processings.

The MRI apparatus 100 of this embodiment realizes the functions of a static magnetic field generating unit 110 which generates a static magnetic field in a space in which the subject 10 is placed, an RF pulse transmission unit 120 which irradiates (transmits) a radio frequency magnetic field on the object of measurement, a signal reception unit 130 which detects (receives) radio frequency signals induced by the radio frequency magnetic field transmitted by the RF pulse transmission unit 120, a gradient magnetic field application unit 140 which applies a gradient magnetic field for adding special information to the radio frequency signals, an image reconstruction unit 150 which reconstructs an image from the radio frequency signals received by the signal reception unit 130, and a measurement control unit 160 which controls operations of the RF pulse transmission unit 120, the gradient magnetic field application unit 140, the signal reception unit 130, and the image reconstruction unit 150, as shown in FIG. 3, with the aforementioned components.

The static magnetic field generating unit 110 is realized by the static magnetic field generating magnet 11.

The RF pulse transmission unit 120 is realized by a part for irradiating a radio frequency magnetic field in the radio frequency magnetic field coil systems 13, the synthesizer 16, the modulator 17, and hardware and control software for applying a radio frequency magnetic field in the control device 14.

The signal reception unit 130 is realized by a part for detection of a radio frequency magnetic field in the radio frequency magnetic field coil systems 13, the amplifier 18, the AD converter 19, and hardware and control software for detecting a radio frequency magnetic field in the control device 14.

The gradient magnetic field application unit 140 is realized by the gradient magnetic field generating coil 12, the gradient magnetic field power supply 15, and hardware and control software for applying a gradient magnetic field in the control device 14.

The measurement control unit 160 is realized by hardware and control software for measurement control in the control device 14 and the computer 20.

The image reconstruction unit 150 is realized by hardware and control software for data processing in the computer 20.

In addition, depending on the configuration, the RF pulse transmission unit 120, the signal reception unit 130, the gradient magnetic field application unit 140, the measurement control unit 160, and the image reconstruction unit 150 may share hardware and software, and they may be inseparable. For example, when the radio frequency magnetic field coil system 13 is made up of a radio frequency magnetic field coil for transmission and reception which serves as both the transmission coil and the receiver RF coil for a radio frequency magnetic field, this radio frequency magnetic field coil belongs to both the RF pulse application unit and the signal reception unit 130. Further, since application and detection of a radio frequency magnetic field, modulation with a gradient magnetic field, and so forth are not independently performed, control software belonging to the units include a part for integrating the operations of them. In addition, the above configuration is just a typical configuration, and the configuration is not limited to the above configuration.

Hereafter, the radio frequency magnetic field coil system 13 will be explained in detail. According to this embodiment, signals of two or more kinds of substances of different resonance frequencies are measured simultaneously, and they are separated in the reconstructed images. In the separation, sensitivity maps of antennas which receive magnetic resonance signals generated from the object of measurement 10 (henceforth referred to as receiver RF coils) are used. Therefore, in this embodiment, the radio frequency magnetic field coil system 13 is provided with two or more receiver RF coils. The number thereof is at least the number of types of substances to be separated, or larger. This embodiment will be explained below by exemplifying a case where the substances to be separated are two kinds of substances, water and an arbitrary metabolite, and two of the receiver RF coils are provided.

Figure 4:
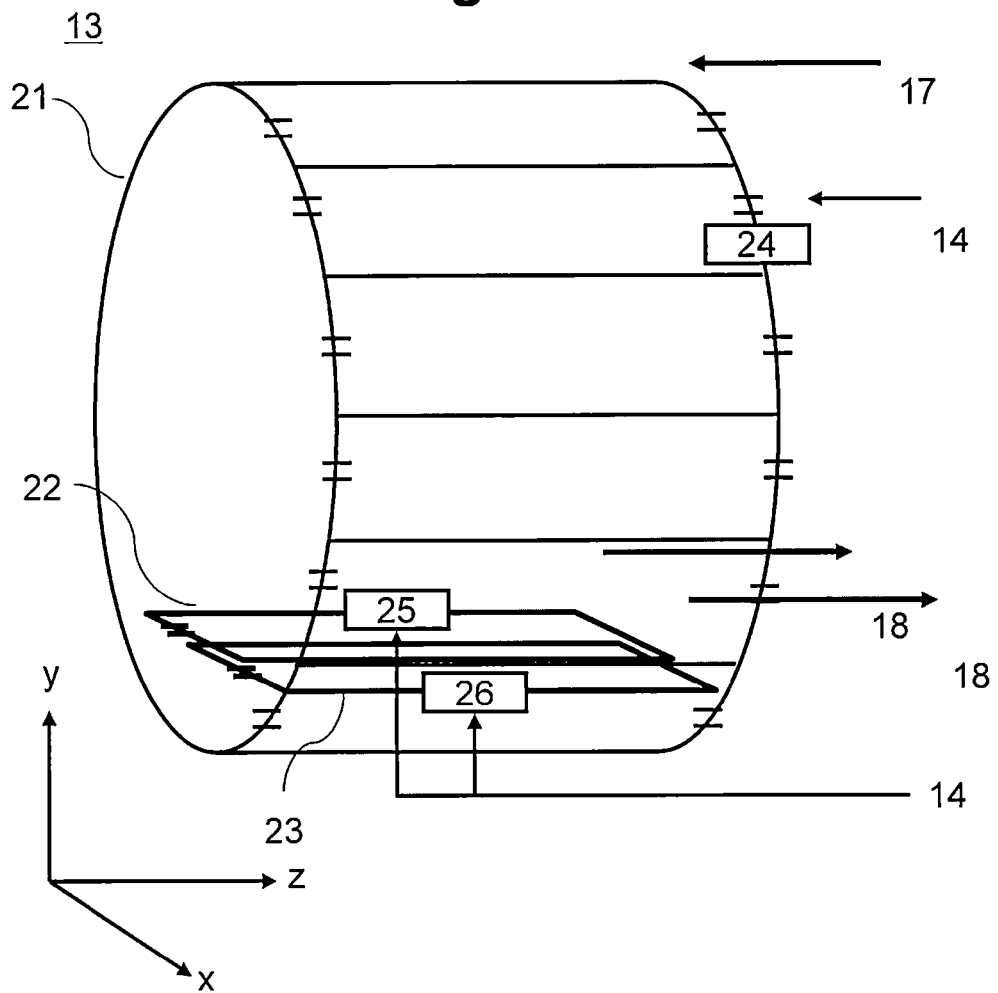
FIG. 4 is a configurational diagram of a radio frequency magnetic field coil system according to the first embodiment.

FIG. 4 is a drawing for explaining the configuration of the radio frequency magnetic field coil system 13 of this embodiment. The radio frequency magnetic field coil system 13 of this embodiment is provided with RF coils 21, 22, and 23 and detuning circuits 24, 25, and 26.

The RF coil 21 belongs to the RF pulse application unit, and functions as an antenna which transmits an excitation pulse to the object of measurement 10. It is henceforth called transmitter RF coil 21. The transmitter RF coil 21 is provided with a coil and a capacitor, and inductance (L) of the coil and capacity (C) of the capacitor are adjusted so that they match the resonance frequency of the magnetic resonance signals.

The RF coil 22 and the RF coil 23 belong to the signal reception unit 130, and function as receiver RF coils. The receiver RF coil 22 and the receiver RF coil 23 each is provided with a coil and a capacitor, and inductance (L) of the coil and capacity (C) of the capacitor are adjusted so that they match the resonance frequency of the magnetic resonance signals, like the transmitter RF coil 21. The receiver RF coils 22 and 23 are connected to different amplifiers 18, respectively, and obtained radio frequency signals (magnetic resonance signals) are separately send to the computer 20. In addition, in this embodiment, the receiver RF coil 22 and the receiver RF coil 23 are loop coils, and they are disposed so that the sensitivity matrices C explained later to be calculated from the sensitivity maps thereof have inverse matrices. For example, they are disposed so that the loop planes thereof are parallel to the xz-plane as shown in this drawing.

The detuning circuits 24, 25, and 26 shift LC resonance frequencies of each of the receiver RF coils 22 and 23 and the transmitter RF coil 21 from the frequency of the magnetic resonance signals at the time of transmission and reception of a radio frequency magnetic field to prevent interference between the coils. That is, at the time of applying the excitation pulses, the detuning circuits 25 and 26 are operated on the basis of a control signal sent from the control device 14 to shift the LC resonance frequencies of the receiver RF coils 22 and 23 from the frequency of the magnetic resonance signals so that they should not function as antennas. Further, at the time of signal detection, the detuning circuit 24 is operated on the basis of a control signal sent from the control device 14 to shift the LC resonance frequency of the transmitter RF coil 21 from the frequency of the magnetic resonance signals so that the transmitter RF coil 21 should not function as an antenna.

This configuration is just a typical example, and the number and shape of the RF coils, the detuning circuit, and so forth are not limited to those mentioned above. For example, the number of the receiver RF coils used for the signal detection may be three or larger. Further, they may be disposed so that they surround the circumference of the object of measurement 10. Further, two or more of the RF coils may serve as coils for transmission and reception. Furthermore, each RF coil may have any of various shapes including circular shape, quadrangular shape, birdcage shape, butterfly shape, saddle shape, and so forth, and the disposition of the capacitor is not particularly limited, either. Although each of the detuning circuits 24, 25, and 26 is shown at only one position in the drawing for simplicity, they may be disposed at a plurality of positions in order to enhance the effect of detuning.

Hereafter, the processing performed by the measurement control unit 160 will be explained in detail. As described above, the measurement control unit 160 of this embodiment controls operations of the RF pulse transmission unit 120, the signal reception unit 130, the gradient magnetic field application unit 140, and the image reconstruction unit 150 to perform imaging with the MRI apparatus 100. In this control of the operations, the measurement control unit 160 of this embodiment controls each unit so that images of water and a metabolite are obtained by one time of execution of an image acquisition sequence. Specifically, the measurement is performed so that only water signals shift on the image, and a spectroscopic image is reconstructed from obtained echo signals (magnetic resonance signals). Then, this spectroscopic image is separated into a spectroscopic image in which water signals shift (shifted water spectroscopic image) and a metabolite spectroscopic image by using sensitivity maps of two or more of the receiver RF coils. After the separation, the shift amounts in the shifted water spectroscopic image is corrected to obtain a water spectroscopic image in which water signals are returned to the correct positions. Further, water signals remaining in the metabolite spectroscopic image are eliminated by using the separated shifted water spectroscopic image and water spectroscopic image.

In order to realize the above processing, the measurement control unit 160 of this embodiment is provided with a shifting signal measurement unit 210, a separation processing unit 220, a shifted signal correction unit 230, and a residual signal removal unit 240, as shown in FIG. 3. Hereafter, the details of the functions of those units will be explained.

The shifting signal measurement unit 210 performs shifting signal measurement processing in which a spectroscopic image is obtained with shifting signals of two or more kinds of substances as objects of measurement by different amounts of shift. Since water and an arbitrary metabolite are the objects of measurement in this embodiment, the measurement is performed so that only water signals shift on the measured image. The measured image is obtained with each of the receiver RF coils 22 and 23 by reconstruction using three-dimensional data for two dimensions of k-space and one dimension of time obtained with each of the receiver RF coils 22 and 23. Such three-dimensional data for two dimensions of k-space and one dimension of time obtained with each of the receiver RF coils 22 and 23 are henceforth referred to simply as k-t data.

First, the pulse sequence executed by the shifting signal measurement unit 210 of this embodiment in order to collect the aforementioned k-t data will be explained. This pulse sequence is stored beforehand in the storage device of the computer 20. The shifting signal measurement unit 210 controls the RF pulse transmission unit 120, the signal reception unit 130, and the gradient magnetic field application unit 140 according to this pulse sequence.

The pulse sequence executed by the shifting signal measurement unit 210 has a pre-pulse sequence for modulating only the longitudinal magnetization of water signals to a predetermined intensity, and a region selective type MRSI pulse sequence (henceforth referred to as main scan pulse sequence) for imaging signals from a desired region.

First, the main scan pulse sequence will be explained. An example of the main scan pulse sequence 300 is shown in FIG. 5. In FIG. 5, the horizontal axis indicates time (t), and the radio frequency magnetic field RF, and the gradient magnetic fields Gx, Gy, and Gz for the x-, y-, and z-directions are indicated along the vertical axis to represent application timings and intensities of them. Further, AD represents a signal acquisition period. The above shall similarly apply to all the pulse sequences to be mentioned in this specification.

The main scan pulse sequence 300 shown in FIG. 5 is a known MRSI pulse sequence. The main scan pulse sequence 300 of this embodiment uses one excitation pulse RF1, two inversion pulses RF2 and RF3, and gradient magnetic field pulses Gs1, Gs1', Gs2 and Gs3 to selectively excite a predetermined region of interest and obtain an FID (free induction decay) signal FID1 from this region of interest. The time points corresponding to ½ of time integrations of the excitation pulse RF1, inversion pulses RF2, and RF3 are referred to as pulse centers 301, 302, and 303, respectively.

Operation realized with the main scan pulse sequence 300 shown in FIG. 5 will be briefly explained with reference to FIG. 6A, FIG. 6B and FIG. 6C. FIG. 6A, FIG. 6B and FIG. 6C includes drawings for explaining a region excited by using the main scan pulse sequence 300. FIGS. 6A, 6B, and 6C are an axial image 410 for positioning, a sagittal image 420, and a coronal image 430, respectively.

The excitation pulse RF1, and the gradient magnetic field pulses Gs1 and Gs1' are applied first to excite a section 401 for the z-direction. Then, the inversion pulse RF2 and the gradient magnetic field Gs2 are applied to invert only the nuclear magnetization in the region at which the section 401 for the z-direction and the section 402 for the y-direction intersect. In this operation, the application timings of the inversion pulse RF2 and the gradient magnetic field Gs2 are controlled so that the time lag between the pulse centers 301 and 302 should become TE/4 (TE is echo time). Then, the inversion pulse RF3 and the gradient magnetic field Gs3 are applied to invert only the nuclear magnetization in the region of interest 404 where the section 401 for the z-direction, the section 402 for the y-direction, and the section 403 for the x-direction intersect. In this operation, the application timings of the inversion pulse RF3 and the gradient magnetic field Gs3 are controlled so that the time lag between the pulse centers 302 and 303 should become TE/2. Then, AD is started to obtain the free induction decay signal FID1. The signal acquisition period Tp1 for the free induction decay signal FID1 is determined by setting desired spectrum band and sampling numbers.

The gradient magnetic fields Gd1 to Gd6 and the gradient magnetic fields Gd1' to Gd6' are gradient magnetic fields for rephasing the phase of the nuclear magnetization excited with the excitation pulse RF1, and dephasing the phase of the nuclear magnetization excited with the inversion pulses RF2 and RF3. Further, after application of the excitation pulse RF1, the phase encoding gradient magnetic fields Gp1 and Gp2 are applied. Intensities of the phase encoding gradient magnetic fields Gp1 and Gp2 are changed for every excitation to impart positional information to the magnetic resonance signals generated from the region of interest 404. In this embodiment, if it is supposed that, for example, Gp1 is changed $N_1$ times, and Gp2 is changed $N_2$ times, Gp2 is changed $N_2$ times for one Gp1. Therefore, in the whole measurement, Gp1 and Gp2 are changed as combinations in a number of $N_1 \times N_2$. $N_1 \times N_2$ of magnetic resonance signals FID1 obtained as described above are arranged in the k-space to obtain k-t data for the region of interest 404.

Hereafter, the pre-pulse sequence executed in advance of the main scan pulse sequence 300 will be explained. An example of the pre-pulse sequence 310 of this embodiment is shown in FIG. 7. The pre-pulse sequence 310 of this embodiment has a radio frequency magnetic field pulse for selectively exciting only nuclear magnetization contained in water, RFC (henceforth referred to as water selective pulse), and gradient magnetic fields Gsp1 to Gsp3 for spoiling transverse magnetization of water.

As the water selective pulse RFC of this embodiment, for example, a Gaussian radio frequency magnetic field pulse having a center frequency corresponding to the water resonance frequency and a narrowed excitation band (about 1.0 ppm) is used. After the irradiation of the water selective pulse RFC, any one or all of the spoiler gradient magnetic fields Gsp1 to Gsp3 for the x-axis, y-axis and z-axis directions are applied.

In this embodiment, in order to selectively excite only the nuclear magnetization contained in water, RF pulses having two different pulse intensities (flip angles) are used as the water selective pulse RFC. These are referred to as water selective pulses RFC1 and RFC2, respectively.

If longitudinal magnetization of the metabolite is represented as Mm, longitudinal magnetization of water intensity-modulated with the water selective pulse RFC1 is represented as Mw1, a signal acquired by exciting longitudinal magnetization Mw1 of water is represented as S1, longitudinal magnetization of water intensity-modulated with the water selective pulse RFC2 is represented as Mw2, and a signal acquired by exciting longitudinal magnetization Mw2 of water is represented as S2, the water selective pulses RFC1 and RFC2 are adjusted so that the conditions that Mm and Mw1 are parallel to each other, Mm and Mw2 are anti-parallel to each other, and $S2=S1 \times \exp(i\pi)$ are satisfied. The pulse intensities of the water selective pulses RFC1 and RFC2 are calculated beforehand, and stored in the computer 20.

Although the pre-pulse sequence 310 with which the water selective pulse RFC is irradiated once is shown in FIG. 7, the number of times of irradiation of the water selective pulse RFC within the pre-pulse sequence 310 is not limited to the above. The aforementioned conditions may be realized with two or more times of irradiation.

The shifting signal measurement unit 210 of this embodiment executes the pre-pulse sequence 310 so that the water selective pulses RFC1 and RFC2 are alternately irradiated in every one step of phase encoding in the main scan pulse sequence 300 as a pulse sequence to obtain k-t data for every receiver RF coil. The pulse sequence having the pre-pulse sequence 310 for modulating only the longitudinal magnetization of water signals to a predetermined intensity, and the main scan pulse sequence 300 is referred to as water shifting sequence, and the measurement for obtaining k-t data by using the water shifting sequence is called shifting water signal measurement.

Hereafter, the details of the shifting water signal measurement using a water shifting sequence will be explained with reference to FIGS. 8 and 9. A case of shifting water signals for the x-direction on the image will be explained below. In these drawings, phase encoding gradient magnetic fields for the x- and y-directions are represented as Gp1 and Gp2, respectively, coordinates for the kx-direction and the ky-direction in the k-space are represented as $kx_{n1}$ and $kx_{n2}$, respectively, intensities of phase encoding gradient magnetic fields corresponding to them are represented as $Gpx_{n1}$ and $Gpy_{n2}$, respectively, and total numbers of the phase encoding steps are represented as $N_1$ and $N_2$, respectively. $n_1$, $n_2$, $N_1$, and $N_2$ are natural numbers, and they satisfy the conditions of $n_1 \leq N_1$ and $n_2 \leq N_2$. Further, if $n_1$ and $n_2$ which make the intensities of the phase encoding gradient magnetic fields $Gpx_{n1}$ and $Gpy_{n2}$ to be 0 are represented as $v_1$ and $v_2$, respectively, the position represented by k-space coordinates $(kx_{v1}, ky_{v2})$ is defined as the center ($k_0$) of the k-space.

The shifting signal measurement unit 210 of this embodiment is controlled so that when $n_1$ is an odd number, the water selective pulse RFC1 is irradiated, and when $n_1$ is an even number, the water selective pulse RFC2 is irradiated, in the pre-pulse sequence 310.

Figure 8:
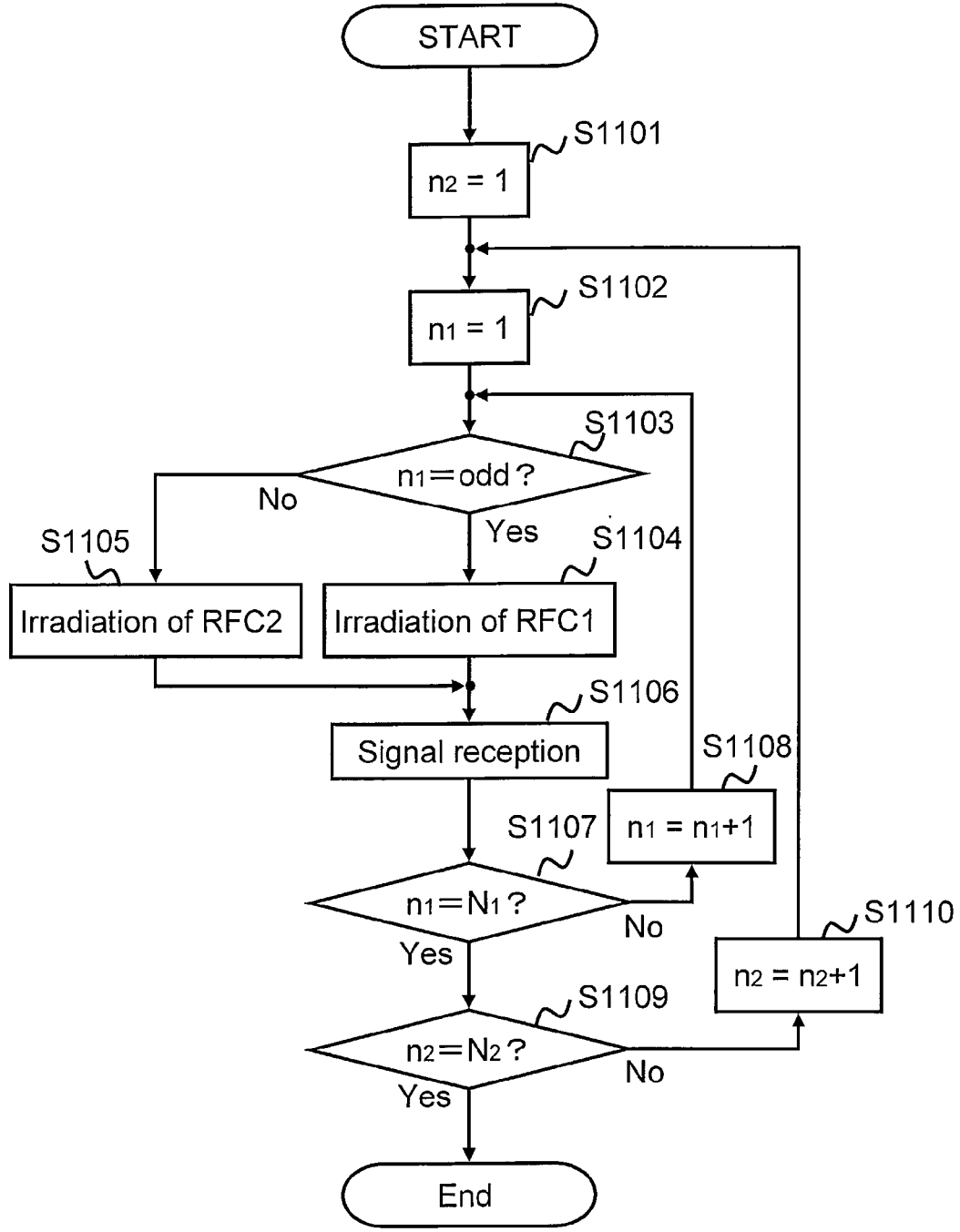
FIG. 8 is a flowchart of shifting water signal measurement processing according to the first embodiment.

FIG. 8 shows the process flow of the shifting water signal measurement processing performed by the shifting signal measurement unit 210.

If the shifting signal measurement unit 210 receives a direction for starting the shifting signal measurement processing, it sets a number of 1 as $n_2$ and $n_1$ as a count of phase encoding step (Steps S1101 and S1102). Then, it determines if $n_1$ is an even number or an odd number (Step S1103), and if it is an odd number, the water selective pulse RFC1 is irradiated in the pre-pulse sequence 310 (Step S1104). On the other hand, if $n_1$ is an even number, the water selective pulse RFC2 is irradiated in the pre-pulse sequence 310 (Step S1105).

Further, after the execution of the pre-pulse sequence 310, the shifting signal measurement unit 210 executes the main scan pulse sequence 300, receives signals with the receiver RF coil 22 and 23 (Step S1106), and arranges them in the k-space for each receiver RF coil.

The above operation is repeated for all of $n_1$ and all of $n_2$ (Steps S1107, S1108, S1109 and S1110).

In addition, in the shifting water signal measurement of this embodiment, it is sufficient that the measurement can be performed under the aforementioned condition for all the measurement points in the k-space, and the order of the steps of phase encoding is not limited. Further, so long as the measurement can be performed so that only water signals shift on the image, the combination for irradiation of water selective pulses RFC1 and RFC2 is not limited to that mentioned above.

Figure 9:
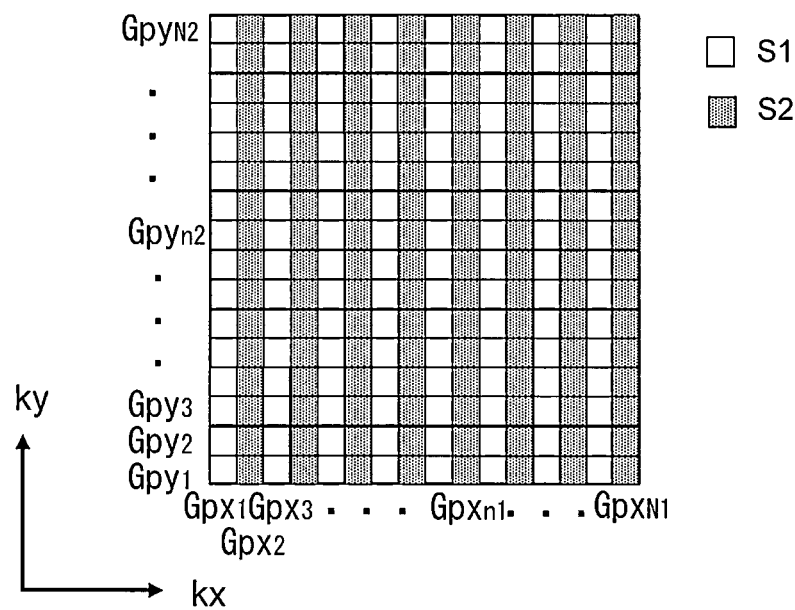
FIG. 9 is an explanatory diagram for explaining the k-t data obtained by the shifting water signal measurement processing according to the first embodiment.

FIG. 9 shows a k-space of k-t data at an arbitrary time measured by executing a water shifting sequence according to the flow shown in FIG. 8. In this drawing, S1 and S2 represent water signals which are intensity-modulated with the water selective pulse RFC1 and RFC2, respectively. In this drawing, intensities $Gpx_{n1}$ and $Gpy_{n2}$ of the phase encoding gradient magnetic fields applied in accordance with the coordinates $kx_{n1}$ of and $ky_{n2}$ for the kx- and ky-directions, respectively, are indicated on the axes of the coordinates. In the k-t data at an arbitrary time obtained with the above water shifting sequence, S1 and S2 appear alternately in a line along the kx-direction, and the signals of the same signal intensities appear in a line along the ky-direction, as shown in this drawing.

The shifting signal measurement unit 210 of this embodiment performs the shifting water signal measurement in accordance with the aforementioned water shifting sequence, and receives the signals S1 and S2 modulated with each phase encoding gradient magnetic field with the receiver RF coils 22 and 23, respectively. Then, it arranges the signals S1 and S2 in the k-t space provided for each of the receiver RF coil 22 and 23 as shown in FIG. 9 to obtain k-t data. Hereafter, the k-t data obtained with the receiver RF coil 22 are referred to as $kt_{22}$, and the k-t data obtained with the receiver RF coil 23 are referred to as $kt_{23}$.

Further, the shifting signal measurement unit 210 performs Fourier transform (FFT) of the k-t data $kt_{22}$ and $kt_{23}$ obtained by the shifting water signal measurement to calculate three-dimensional images $I_{22}$ and $I_{23}$ for two dimensions of space and one dimension of spectrum, respectively. The three-dimensional images $I_{22}$ and $I_{23}$ obtained above are referred to simply as spectroscopic images. In the obtained spectroscopic images, only the water signals shift.

Hereafter, it will be explained that only the water signals shift on the image in the spectroscopic images $I_{22}$ and $I_{23}$ obtained with the aforementioned water shifting sequence. In the following explanation, discrete Fourier transform (DFT) is used for the FFT processing, and explanation is made only for one dimension of the x-direction, for which the water signals are intensity-modulated, for simplicity of the explanation.

If the number of data for the x-direction is represented as $N_1$, k-space data are represented as K(k), and real space data obtained by DFT of K(k) are represented as I(x), there is a relation represented by the following equation (1) on the basis of the principle of DFT.

[Equation 1]

$$I(x - \Delta d) = F\left[K(k) \cdot e^{i\frac{2\pi}{N}k\Delta d}\right] \quad (1)$$

In the equation, i represents an imaginary unit, F[ ] represents a DFT operator, and Δd represent an image shift amount.

If phase to be multiplied with the water shifting sequence of this embodiment at each point in the k-space is represented as ϕ, the shift amount Δd of water in the image obtained by the Fourier transform can be calculated in accordance with the following equation (2).

[Equation 2]

$$\Delta d = \frac{N_1}{2\pi}\phi \quad (2)$$

Since the water signals S1 and S2 are measured so that the condition of S2=S1×exp(iπ) should be satisfied in this embodiment, the phase p to be multiplied at each point in the k-space is π. Therefore, from the equation (2), the shift amount of the water spectroscopic image is $N_1/2$, and the signals shift by ½ of $N_1$, which is the number of data for the x-direction in the image. Signals shifted out of the field of view appear on the opposite side. Hereafter, the above shift amount is simply referred to with an expression that the signals shift by ½ of image in the x-direction. On the other hand, metabolite signals are not influenced by the water selective pulses RFC1 and RFC2, and therefore the spectroscopic image of the metabolite does not shift.

Hereafter, the separation processing unit 220 of this embodiment will be explained. The separation processing unit 220 of this embodiment performs a separation processing for separating the measured image obtained with the shifting signal measurement unit 210 into images of substances as objects of measurement by using sensitivity maps of the receiver RF coils. In the separation processing, a coil sensitivity matrix is calculated on the basis of sensitivity maps of the receiver RF coils, and the spectroscopic image is separated into spectroscopic images of the substances as objects of measurement (water spectroscopic image and metabolite spectroscopic image in this case) by using an inverse matrix of the coil sensitivity matrix.

Figure 10A:
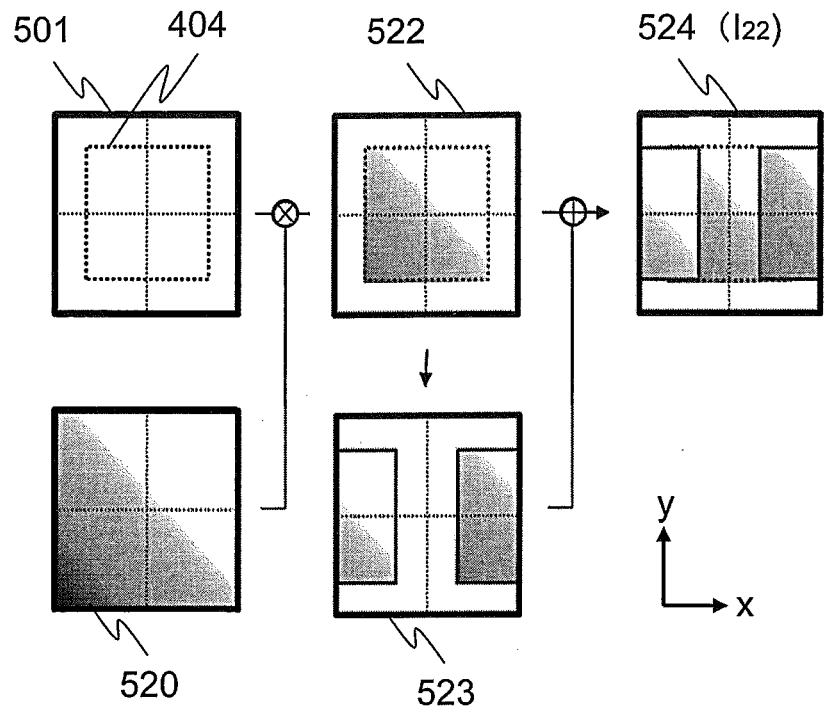
FIG. 10A is an explanatory diagram for explaining a spectroscopic image measured according to the first embodiment.
Figure 10B:
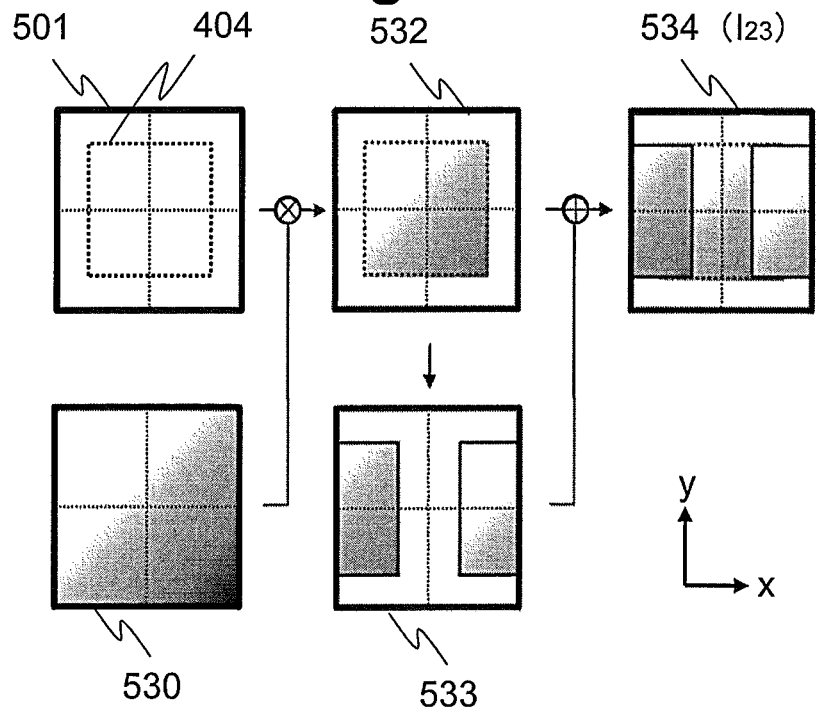
FIG. 10B is an explanatory diagram for explaining a spectroscopic image measured according to the first embodiment.

First, the relation between the spectroscopic images $I_{22}$ and $I_{23}$ measured with the receiver RF coils 22 and 23 and the sensitivity maps of the receiver RF coils 22 and 23 will be explained with reference to FIG. 10A and FIG. 10B. FIG. 10A is a drawing for explaining the spectroscopic image $I_{22}$, and FIG. 10B is a drawing for explaining the spectroscopic image $I_{23}$. Further, water and metabolite signal distribution 501 shown in FIGS. 10A and 10B imitates distributions of signals of water and the metabolite actually existing in the region of interest 404, and it is supposed that water and the metabolite are uniformly distributed in the region of interest 404.

A metabolite spectroscopic image 522 obtained with the receiver RF coil 22 shown in FIG. 10A is obtained by multiplying the water and metabolite signal distribution 501 and sensitivity map 520 of the receiver RF coil 22. Further, a shifted water spectroscopic image 523 is obtained by multiplying the water and metabolite signal distributions 501 and sensitivity map 520, and subsequently shifting by ½ of image in the x-direction with the water shifting sequence. A spectroscopic image 524 ($I_{22}$) actually measured is obtained as the sum of the shifted water spectroscopic image 523 and the metabolite spectroscopic image 522.

The same shall apply to FIG. 10B, and a metabolite spectroscopic image 532 obtained with the receiver RF coil 23 is obtained by multiplying the water and metabolite signal distribution 501 and the sensitivity map 530 of the receiver RF coil 23. Further, a shifted water spectroscopic image 533 is obtained by multiplying the water and metabolite signal distribution 501 and sensitivity map 530, and subsequently shifting by ½ of image in the x-direction with the water shifting sequence. A spectroscopic image 534 ($I_{23}$) actually measured is obtained as the sum of the shifted water spectroscopic image 533 and the metabolite spectroscopic image 532.

Figure 11:
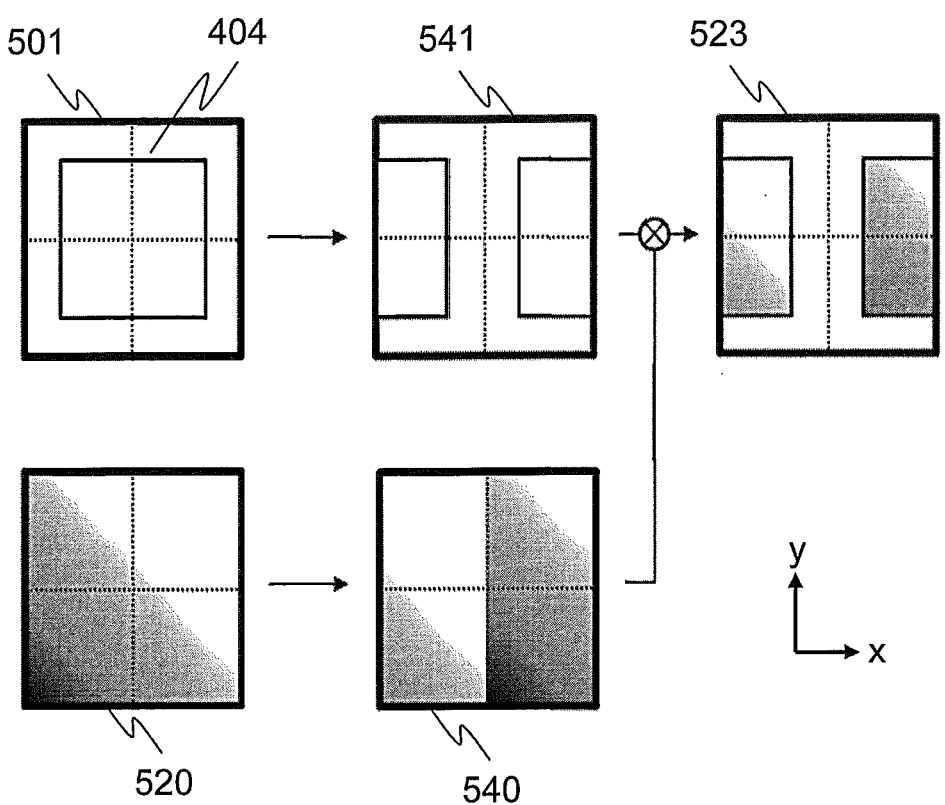
FIG. 11 is an explanatory diagram for explaining another interpretation of the spectroscopic image measured according to the first embodiment.

The shifted water spectroscopic image 523 measured with the receiver RF coil 22 can also be interpreted as one obtained by the procedure shown in FIG. 11. That is, the shifted water spectroscopic image 523 measured with the receiver RF coil 22 can be interpreted to be a product of sensitivity map of shifted water signal 541 obtained by shifting only the sensitivity map of water signal in the water and metabolite signal distribution 501 actually existing at the position of the region of interest 404 for the x-direction and shifted sensitivity map 540 obtained by shifting the sensitivity map 520 for the x-direction.

Therefore, the spectroscopic image 524 ($I_{22}$) can be interpreted as the sum of a product of the water and metabolite signal distribution 501 and the sensitivity map 520, and a product of the sensitivity map of shifted water signal 541 and the shifted sensitivity map 540.

The shifted water spectroscopic image 533 measured with the receiver RF coil 23 can also be similarly interpreted as a product of the sensitivity map of shifted water signal and the shifted sensitivity map obtained by shifting the sensitivity map 530 for the x-direction. Further, the spectroscopic image 534 ($I_{23}$) can be interpreted as the sum of a product of the water and the metabolite signal distribution 501 and the sensitivity map 530, and a product of the sensitivity map of shifted water signal and the shifted sensitivity map.

Therefore, if the sensitivity maps 520 and 530 are defined as metabolite sensitivity map $C_m$, sensitivity map obtained by shifting the metabolite sensitivity map $C_m$ for the x-direction is defined as water sensitivity map $C_w$, the metabolite spectroscopic image is represented as m, and the shifted water spectroscopic image shifted by ½ for the x-direction on the image is represented as $w_s$, and for an arbitrary voxel (x, y) in the measured spectroscopic images 524 ($I_{22}$) and 534 ($I_{123}$), the metabolite sensitivity maps $C_m$ of the receiver RF coils 22 and 23 are represented as $C_m$ (a, x, y) and $C_m$ (b, x, y), respectively, water sensitivity maps $C_w$ are represented as $C_w$ (a, x, y) and $C_w$ (b, x, y), respectively, the metabolite signal is represented as m (x, y), and the water shift signal shifted by ½ on the image in the x-direction is represented as $w_s$ (x, y), the signal intensities $I_{22}$ (x, y) and $I_{23}$ (x, y) of the arbitrary voxel (x, y) in the spectroscopic images $I_{22}$ and $I_{23}$ are represented by the following equation (3).

[Equation 3]

$$\begin{bmatrix} I_{22}(x,y) \\ I_{23}(x,y) \end{bmatrix} = \begin{bmatrix} C_m(a,x,y) & C_w(a,x,y) \\ C_m(b,x,y) & C_w(b,x,y) \end{bmatrix} \begin{bmatrix} m(x,y) \\ w_s(x,y) \end{bmatrix} \quad (3)$$

In the equation (3), the matrix having the sensitivity maps $C_m$ and $C_w$ is referred to as sensitivity matrix C.

The separation processing unit 220 of this embodiment separates metabolite signals and water signals by using difference in the sensitivity ratio of each receiver RF coil for water sensitivity map and metabolite sensitivity map for an arbitrary voxel. Therefore, when the determinant of the sensitivity matrix C is not 0, by using the inverse matrix $C^{-1}$ thereof, the metabolite signal m (x, y) and water shift signal $w_s$ (x, y) at the coordinate point (x, y) in the metabolite spectroscopic image m and the shifted water spectroscopic image $w_s$ are calculated in accordance with the following equation (4).

[Equation 4]

$$B = C^{-1}I \quad (4)$$

here, $$C^{-1} = \frac{1}{|C|}\begin{bmatrix} C_w(b,x,y) & -C_w(a,x,y) \\ -C_m(b,x,y) & C_m(a,x,y) \end{bmatrix},$$

$$|C| = C_m(a,x,y)C_w(b,x,y) - C_m(b,x,y)C_w(a,x,y),$$

$$B = \begin{bmatrix} m(x,y) \\ w_s(x,y) \end{bmatrix}, \quad I = \begin{bmatrix} I_{22}(x,y) \\ I_{23}(x,y) \end{bmatrix}$$

The separation processing unit 220 of this embodiment separates the spectroscopic images $I_{22}$ and $I_{23}$ obtained with the receiver RF coils 22 and 23, respectively, into a metabolite spectroscopic image of which signal value of arbitrary voxel (x, y) is m (x, y), and a shifted water spectroscopic image of which signal value of arbitrary voxel (x, y) is $w_3$ (x, y), by using the aforementioned equation (4).

The sensitivity map (metabolite sensitivity map $C_m$) used for the separation processing is calculated by a method similar to a generally known sensitivity map calculating method. For example, when the transmitter RF coil 21 belonging to the RF pulse transmission unit 120 has a spatially uniform sensitivity map, sensitivity maps of the receiver RF coils 22 and 23 are calculated from intensity ratio of an image obtained by transmission and reception performed with the transmitter RF coil 21 and an image obtained by using the transmitter RF coil 21 for transmission and the receiver RF coils 22 and 23 for reception. Further, the sensitivity maps of the receiver RF coils 22 and 23 may also be calculated from intensity ratios of root sum square image of images obtained by using the transmitter RF coil 21 for transmission and the receiver RF coils 22 and 23 for reception, and each of the images.

The sensitivities of the receiver RF coils 22 and 23 often spatially change smoothly. Therefore, when the sensitivity maps are calculated by these methods, by obtaining them only for a low frequency domain, measurement time can be shortened, and body motion artifacts can be suppressed.

Further, since the sensitivity maps depend on the structure or composition of the object of measurement, the measurement for calculating the sensitivity maps is desirably performed by using an actual object of measurement 10. In such a case, an imaging sequence for calculating sensitivity map may be executed, and a sensitivity map may be calculated from an obtained MRI image before performing the aforementioned shifting signal measurement.

However, a sensitivity map calculated from a result of a preliminary measurement performed by using a simulated sample may also be used. In this case, the calculated sensitivity map is stored in the storage device of the computer 20 beforehand.

Further, in this embodiment, the water sensitivity map $C_w$ is obtained by shifting the metabolite sensitivity map $C_m$ by the shift amount of water signal shifted in the shifting water signal measurement.

Hereafter, the shifted signal correction unit 230 of this embodiment will be explained. The shifted signal correction unit 230 of this embodiment performs a shifted signal correction processing for returning signals of a measured image obtained by the shifting signal measurement unit 210 among the measured images separated by the separation processing unit 220 to the original positions.

In the shifted water spectroscopic image $w_s$ calculated in accordance with the aforementioned equation (4), the signals constituting the spectroscopic image are shifted for the x-direction. Therefore, the shifted signal correction unit 230 of this embodiment moves the signals by the shift amount of the shifting performed with the water shifting sequence to the opposite direction to return them to the positions of the original image and thereby obtain a water spectroscopic image w.

The shifted signal correction may be performed on the shifted water spectroscopic image $w_s$, or may be performed in the k-space by using the equation (1) after Fourier transform of the shifted water spectroscopic image $w_s$ is performed. When the shifted signal correction is performed on the image, each pixel is moved by the shift amount to the direction opposite to the shifted direction. In this case, when the water selective pulse RFC2 is irradiated at the k-space center $k_0$ in the shifting water signal measurement, each pixel is moved by the shift amount to the direction opposite to the shifted direction, and then −1 is multiplied. When the correction is performed in the k-space, the phase −ϕ is multiplied at each point for the kx-direction by using the equation (1). The water spectroscopic image calculated as described above is represented as w.

Hereafter, the residual signal removal unit 240 of this embodiment will be explained. The residual signal removal unit 240 of this embodiment performs a remaining signal elimination processing for eliminating signals of other substances remained due to errors generated in the measurement and separation processing.

In the calculated metabolite spectroscopic image m, water signals remain due to the errors involved in the measurement and separation processing. The major factors of the generation of such remaining water signals include two factors, (1) errors induced by the water intensity-modulation performed with the water shifting sequence, and (2) errors induced by the separation processing using a sensitivity matrix.

First, the errors induced by the factor (1) mentioned above will be explained with reference to FIGS. 12A to 12C. FIG. 12A shows the metabolite spectroscopic image m, FIG. 12B shows the shifted water spectroscopic image w, calculated by the separation processing, and FIG. 12C shows the water spectroscopic image w obtained by the shifted signal correction of the shifted water spectroscopic image $w_s$. In these images, water signal intensities at a predetermined voxel VA (x, y) is represented as mVA (x, y), $w_s$VA (x, y), and wVA (x, y), respectively.

Since the water signal of the voxel VA is S1 when the measurement is performed with intensity modulation of water signals with only the water selective pulse RFC1, and the water signal of the voxel VA is S2 when the measurement is performed with intensity modulation of water signals with only the water selective pulse RFC2 as described above, the remaining water signal mVA in the metabolite spectroscopic image m and the water signal wVA in the water spectroscopic image w are represented by the following equations (5) and (6), respectively.

$$mVA = (S1+S2)/2 \quad (5)$$

$$wVA = (S1-S2)/2 \quad (6)$$

Under the ideal condition where the water signal S1 and the water signal S2 satisfy the aforementioned condition: $S2 = S1 \times \exp(i\pi) = -S1$, the equations (5) and (6) are represented as the following equations (7) and (8), respectively.

$$mVA = 0 \quad (7)$$

$$wVA = S1 \quad (8)$$

That is, in the metabolite spectroscopic image m, the remaining water signal mVA becomes zero, and thus water signal does not remain.

However, spatial unevenness is actually induced in the water intensity modulation with the water selective pulses RFC1 and RFC2 due to inhomogeneity of the static magnetic field or inhomogeneity of transmitted RF, and the aforementioned condition is not necessarily satisfied. When the intensity ratio of the actual water signal S1 and the water signal S2 is represented by p', the aforementioned conditions is represented as $S2 = p' \times S1 \times \exp(i\pi) = -p' \times S1$, and therefore the equations (5) and (6) are represented as the equation (9) and (10), respectively.

$$mVA = (S1+S2)/2 = (1-p') \times S1/2 \quad (9)$$

$$wVA = (S1-S2)/2 = (1+p') \times S1/2 \quad (10)$$

Furthermore, if $(1-p')/(1+p') = p$, the following equation (11) can be derived by using the equations (9) and (10).

$$mVA = p \times wVA \quad (11)$$

From the above, it can be understood that the remaining water signal mVA in the voxel VA of the metabolite spectroscopic image m is proportional to the water signal wVA in the voxel VA of the water spectroscopic image w.

Hereafter, the factor (2) mentioned above will be explained with reference to FIGS. 12A and 12B. Ideally, the remaining water signal mVA in the voxel VA of the metabolite spectroscopic image m calculated by the separation processing in accordance with the equation (4) is 0. However, the water signal mVA may remain due to noise components contained in the sensitivity map, or errors included in the sensitivity map at a position where the object of measurement (subject) 10 does not exist. When the ratio of the water signal remaining due to the errors of the separation processing is represented by q, the remaining water signal mVA in the voxel VA of the metabolite spectroscopic image m is represented by the equation (12).

$$mVA = q \times w_s VA \quad (12)$$

From the above, when both (1) the errors due to the intensity modulation of the water signals with the water shifting sequence, and (2) the errors due to the separation processing using a sensitivity matrix are induced, the remaining water signal mVA in the voxel VA of the metabolite spectroscopic image m is represented by the following equation (13) using the equations (11) and (12).

$$mVA = p \times wVA + q \times w_s VA \quad (13)$$

Therefore, if the proportionality constants p and q in the equation (13) are obtained, the value of the remaining water signal mVA included in the metabolite spectroscopic image m can be obtained, and eliminated.

Figure 13:
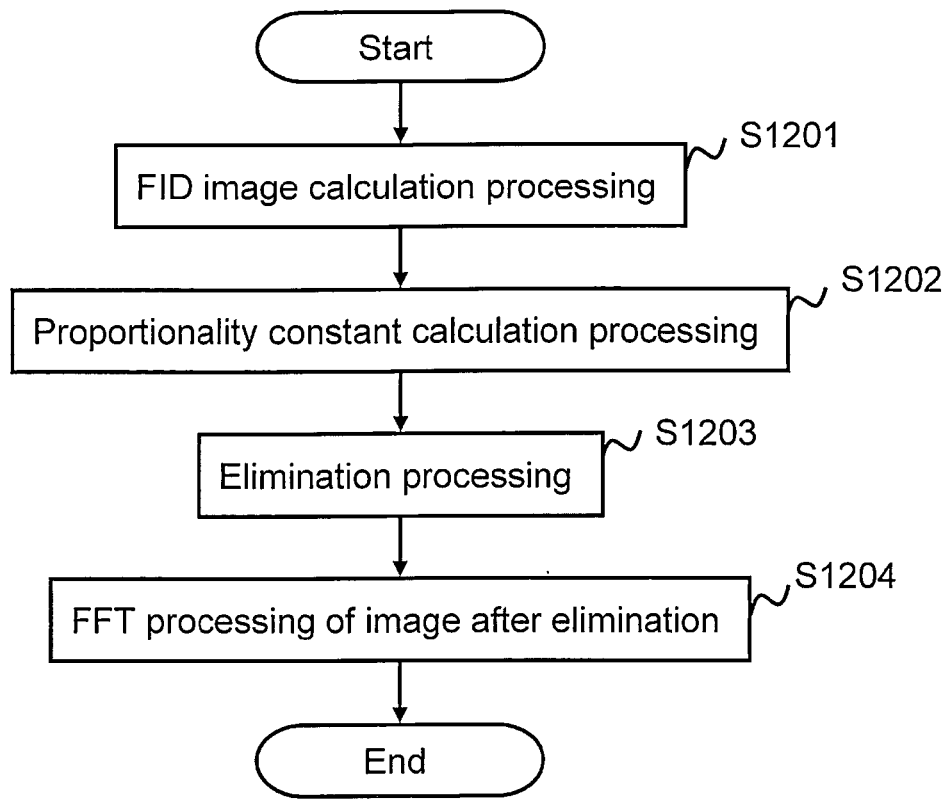
FIG. 13 is a flowchart of the remaining signal eliminating operation according to the first embodiment.

The flow of the remaining water signal elimination processing performed by the residual signal removal unit 240 of this embodiment according to the aforementioned principle will be explained with reference to FIG. 13.

First, the residual signal removal unit 240 performs Fourier transform (FFT) of the metabolite spectroscopic image m, the water spectroscopic image w, and the shifted water spectroscopic image $w_s$ for the spectrum direction to calculate the three-dimensional images for two dimensions of real space and one dimension of time, $m_t$, $w_t$, and $w_{st}$ (henceforth referred to simply as FID images), respectively (FID image calculation processing, Step 1201).

Then, the residual signal removal unit 240 calculates the proportionality constants p and q of each voxel in each of the FID images $m_t$, $w_t$, and $w_{st}$ by the least square method, respectively (proportionality constant calculation processing, Step S1202).

When the number of measurement points for the time direction is represented as T, the relation of the FID images $m_t$, $w_t$, and $w_{st}$ for each voxel (x, y) is represented by the simultaneous linear equation (14) from the equation (13).

[Equation 14]

$$\begin{bmatrix} m_t(t_1, x, y) \\ m_t(t_2, x, y) \\ \vdots \\ m_t(t_T, x, y) \end{bmatrix} = \begin{bmatrix} w_t(t_1, x, y) & w_{st}(t_1, x, y) \\ w_t(t_2, x, y) & w_{st}(t_2, x, y) \\ \vdots & \vdots \\ w_t(t_T, x, y) & w_{st}(t_T, x, y) \end{bmatrix} \begin{bmatrix} p \\ q \end{bmatrix} \quad (14)$$

Therefore, the residual signal removal unit 240 calculates the proportionality constants p and q by the least square method using the equation (15) derived from the equation (14) with $w_t$ and $w_{st}$ as the basis functions. H is a symbol representing a transposition complex conjugate.

[Equation 15]

$$P = (W^H W)^{-1} W^H M_t \qquad (15)$$

here, $$P = \begin{bmatrix} p \\ q \end{bmatrix}, \quad W = \begin{bmatrix} w_t(t_1, x, y) & w_{st}(t_1, x, y) \\ w_t(t_2, x, y) & w_{st}(t_2, x, y) \\ \vdots & \vdots \\ w_t(t_T, x, y) & w_{st}(t_T, x, y) \end{bmatrix},$$

$$M_t = \begin{bmatrix} m_t(t_1, x, y) \\ m_t(t_2, x, y) \\ \vdots \\ m_t(t_T, x, y) \end{bmatrix}$$

Then, the residual signal removal unit 240 calculates the remaining water signal mVA in each voxel VA (x, y) by using the calculated proportionality constants p and q, and subtracts mVA (x, y) from the FID image $m_t$ (x, y) obtained by using the equation (14) to calculate an FID image $m_{ct}$ (x, y) after the remaining signal elimination (elimination processing, Step 1203).

The residual signal removal unit 240 performs Fourier transform (FFT) of the FID image $m_{ct}$ after the remaining signal elimination to obtain a metabolite spectroscopic image in which the remaining water signal mVA is removed (FFT processing for image after elimination, Step 1204).

When the remaining water signals induced due to the factors (1) and (2) overlap the metabolite peak and are so small that they do not affect the metabolite spectroscopic image, the remaining signal elimination processing may not be performed. In such a case, the residual signal removal unit 240 may not be provided.

In the above, the details of the processings for the functions of the measurement control unit 160 of this embodiment were explained. The above explanation was made by exemplifying a case where the measurement control unit 160 is provided with the separation processing unit 220, the shifted signal correction unit 230, and the residual signal removal unit 240. However, the present invention is not limited to such a configuration. For example, the image reconstruction unit 150 may be provided with these units.

Figure 14:
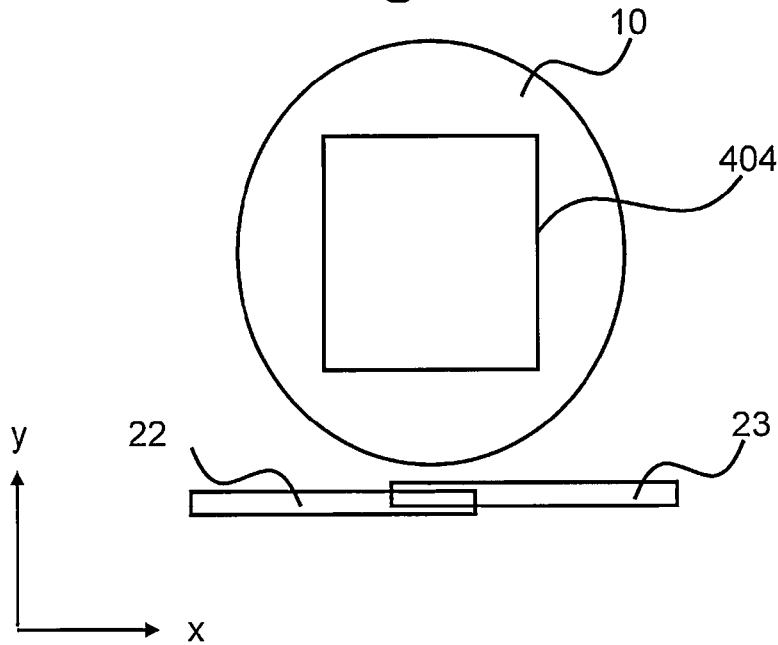
FIG. 14 is an explanatory diagram for explaining positional relationship of the receiver RF coils according to the first embodiment, a region of interest, and a measurement object.

Hereafter, relation of the disposition of the receiver RF coils 22 and 23 of this embodiment and the shifting direction in the shifting water signal measurement will be explained. An example of the positional relationship of the object of measurement 10, the region of interest 404 of which region selection is performed with the main scan pulse sequence 300, and the receiver RF coils 22 and 23 at the time of performing the measurement with the measurement control unit 160 of this embodiment is shown in FIG. 14.

As described above, the separation processing unit 220 of this embodiment uses difference in the sensitivity ratio of the receiver RF coils 22 and 23 for the water sensitivity map and the metabolite sensitivity map for an arbitrary voxel for separation of metabolite signal and water signal. Therefore, the disposition of the receiver RF coils 22 and 23 and the shifting direction in the shifting water signal measurement must be determined so that the condition that the determinant of the sensitivity matrix C, |C|, is not 0 is satisfied in the equation (4).

In general, sensitivity map of a loop coil monotonously decreases in proportion to the distance from the center of the loop for the direction parallel to the loop plane, and monotonously decreases in proportion to the distance from the loop plane for the direction perpendicular to the loop plane. Therefore, when shifting water signal measurement is performed with a water shifting sequence in which water signals shift for the x-direction as in this embodiment, the receiver RF coils 22 and 23 are disposed so that the loop planes are perpendicular to the slice plane, and they are disposed in an array for the x-direction, as shown in FIG. 14. On the contrary, when the receiver RF coils 22 and 23 are disposed so that the loop planes are perpendicular to the slice plane, and they are disposed in an array for the x-direction, the shifting direction of water signal in the water shifting sequence is determined to be the x-direction.

However, the disposition of the receiver RF coils 22 and 23 and the shifting direction are not limited to those mentioned above, and they may be determined so that the condition of the determinant |C|≠0 is satisfied.

Figure 15:
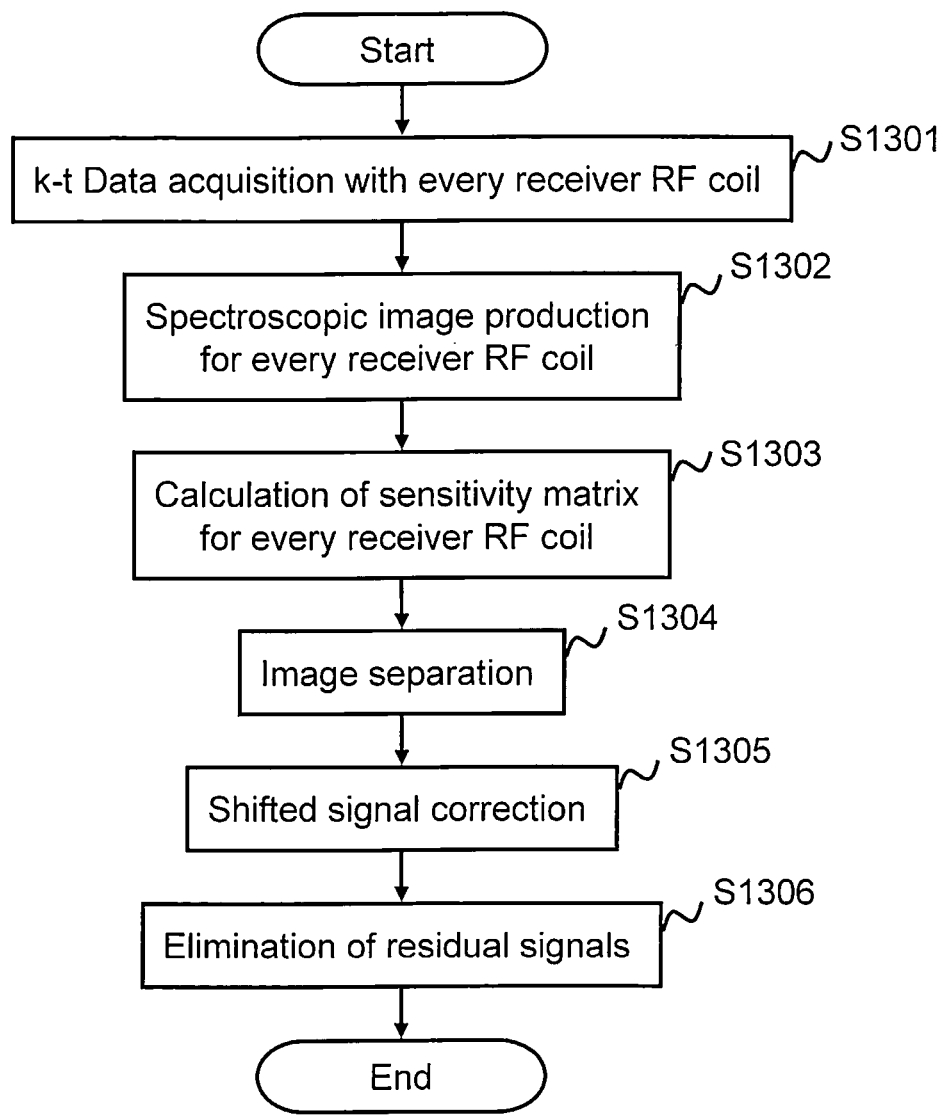
FIG. 15 is a flowchart of a measurement processing according to the first embodiment.

Next, the flow of the measurement processing performed by the measurement control unit 160 of this embodiment provided with the aforementioned units will be explained. FIG. 15 shows the process flow of the measurement processing of this embodiment.

When the shifting signal measurement unit 210 receives a direction for starting the measurement, it performs the shifting water signal measurement to obtain k-t data with every receiver RF coil (Step S1301). Then, the shifting signal measurement unit 210 performs FFT of the obtained k-t data to obtain a spectroscopic image for every receiver RF coil (Step S1302).

Then, the separation processing unit 220 calculates a coil sensitivity matrix for every receiver RF coil from sensitivity maps of the receiver RF coils (Step S1303). Then, it separates the spectroscopic image into a shifted water spectroscopic image and a metabolite spectroscopic image by using the coil sensitivity matrix (Step S1304).

The shifted signal correction unit 230 performs the shifted signal correction processing of the separated shifted water spectroscopic image to obtain a water spectroscopic image (Step S1305).

The residual signal removal unit 240 performs a remaining signal elimination processing, if needed (Step S1306).

As explained above, according to this embodiment, a water image and a metabolite image can be obtained with execution of one image acquisition sequence. That is, a water image and a metabolite image can be obtained without extending the measurement time.

Although this embodiment was explained by exemplifying a case of using two of receiver RF coils, the number of the receiver RF coil is not limited to two. It may be three or larger. For example, when the number of the receiver RF coils is three, the sensitivity matrix C is a matrix having two lines and three rows. In such a case, a solution can be obtained by, for example, a method of converting it into a regular matrix of two lines and two rows by normalization of a matrix, and obtaining an inverse matrix thereof, as a general solution of matrix. Further, noise components of the receiver RF coils may be measured, and an inverse matrix including weighting calculated by using a distributed covariance matrix of the noises of the receiver RF coils (henceforth referred to as noise correlation matrix) may be obtained.

Further, although the this embodiment was explained by exemplifying a case of using two of the receiver RF coils 22 and 23 disposed in an array for the x-direction so that they were perpendicular to the xy-plane as the receiver RF coils, the receiver RF coils to be used are not limited to these. For example, two or more receiver RF coils disposed in the shape of cylinder around the object of measurement 10 as the center may also be used.

An example of such a case as mentioned above is shown in FIG. 16. In this example, each of four receiver RF coils 31, 32, 33, and 34 has a shape of about ¼ of a circle in a plane parallel to the xy plane, and they are disposed so as to form a cylindrical shape as a whole. The receiver RF coils 31, 32, 33, and 34 are separately connected to the amplifier 18, and measured radio frequency signals are separately obtained.

In this drawing, the RF coil for transmission and the detuning circuit are omitted for simplicity of the drawing. Further, in this example, four of the receiver RF coils 31, 32, 33, and 34 are indicated so that they do not overlap with each other, but they are actually disposed so that parts of adjacent receiver RF coils overlap with each other in the side of the cylindrical shape.

Figure 16:
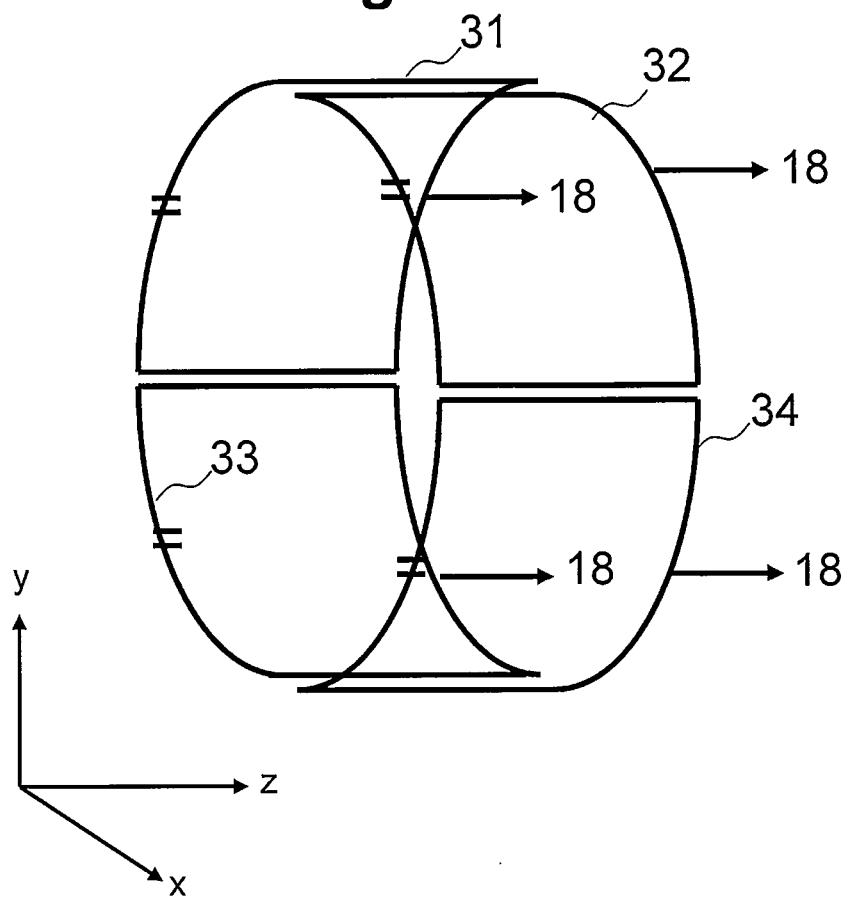
FIG. 16 is an explanatory diagram for explaining another shape of the receiver RF coil according to the first embodiment.

It is sufficient that an inverse matrix of the sensitivity matrix C calculated on the basis of these four of the receiver RF coils 31, 32, 33, and 34 is available, thus the shape and disposition of these four of the receiver RF coils 31, 32, 33, and 34 are not limited to those shown in FIG. 16, and various modifications may be possible.

In addition, in the measurement using the receiver RF coils 31, 32, 33, and 34 shown in FIG. 16, the sensitivity matrix C acquired from the sensitivity maps of the receiver RF coils 31, 32, 33, and 34 is a matrix of two lines and four rows. Therefore, for an inverse matrix operation, a solution used for an inverse matrix operation of high order matrix such as LU decomposition and singular value decomposition is used.

Further, although this embodiment was explained by exemplifying a case where water signals are shifted for the x-direction in the shifting water signal measurement performed by the shifting signal measurement unit 210, the shifting direction is not limited to this direction. It is sufficient that the determinant of the aforementioned sensitivity matrix is not 0, and the shift may be possible for an arbitrary axis along which a phase encoding gradient magnetic field is applied, such as shift for the y-direction and shift for the xy-direction.

The details of the shifting water signal measurement where the shifting direction is the xy-direction will be explained with reference to FIGS. 17 and 18. In these drawings, phase encoding gradient magnetic fields for the x- and y-directions are represented as Gp1 and Gp2, respectively, coordinates for the kx-direction and the ky-direction in the k-space are represented as $kx_{n1}$ and $ky_{n2}$, respectively, intensities of phase encoding gradient magnetic fields corresponding to them are represented as $Gpx_{n1}$ and $Gpy_{n2}$, respectively, and total numbers of the phase encoding steps are represented as $N_1$ and $N_2$, respectively. $n_1$, $n_2$, $N_1$, and $N_2$ are natural numbers, and they satisfy the conditions of $n_1 \le N_1$ and $n_2 \le N_2$. Further, if $n_1$ and $n_2$ which make the intensities of the phase encoding gradient magnetic fields $Gpx_{n1}$ and $Gpy_{n2}$ to be 0 are represented as $v_1$ and $v_2$, respectively, the position represented by k-space coordinates $(kx_{v1}, ky_{v2})$ is defined as the center ($k_0$) of the k-space.

Also in this modification, the shifting signal measurement unit 210 controls the units to execute a water shifting sequence so that the water selective pulse RFC1 is irradiated when both $n_1$ and $n_2$ are even numbers, or when both $n_1$ and $n_2$ are odd numbers, and the water selective pulse RFC2 is irradiated in the other cases.

Figure 17:
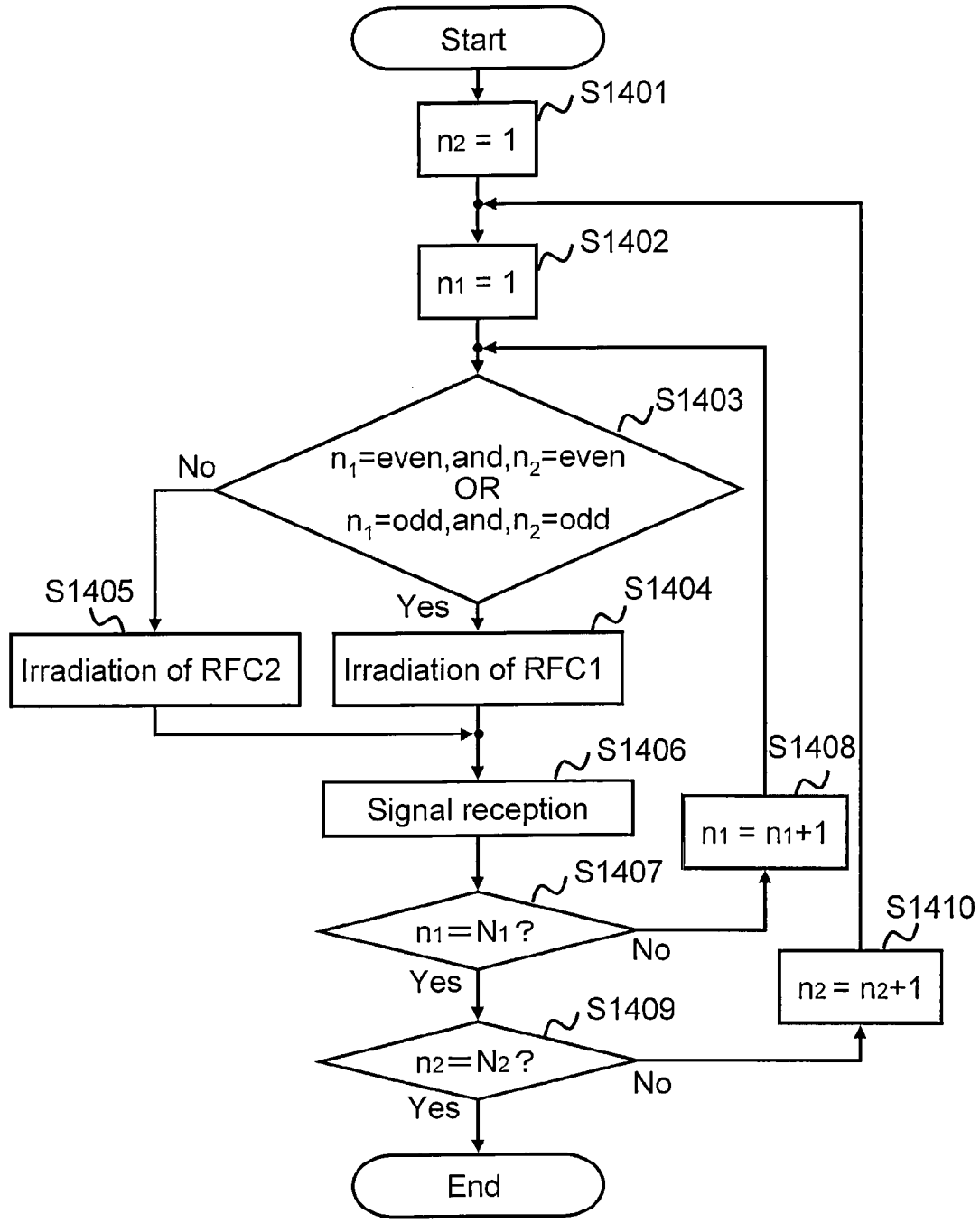
FIG. 17 is a flowchart of the shifting water signal measurement processing in the case of shifting water signals for the xy-direction in the first embodiment.

FIG. 17 shows the process flow of the measurement processing performed by the shifting signal measurement unit 210.

If the shifting signal measurement unit 210 receives a direction for starting the shifting signal measurement processing, it sets a number of 1 as $n_2$ and $n_1$ as a count of phase encoding step (Steps S1401 and S1402). Then, it determines if $n_1$ and $n_2$ are an even number or an odd number (Step S1403), and if the both are odd numbers or the both are even numbers, the water selective pulse RFC1 is irradiated in the pre-pulse sequence 310 (Step S1404). On the other hand, if one of the both is an odd number and the other is an even number, the water selective pulse RFC2 is irradiated in the pre-pulse sequence 310 (Step S1405).

Further, after the execution of the pre-pulse sequence 310, the shifting signal measurement unit 210 executes the main scan pulse sequence 300, receives magnetic resonance signals with the receiver RF coil 22 and 23 (Step S1406), and arranges them in the k-space for each receiver RF coil.

The above operation is repeated for all of $n_1$ and all of $n_2$ (Steps S1407, S1408, S1409 and S1410).

In addition, in the shifting water signal measurement of this modification, it is sufficient that the measurement can be performed for all the measurement points in the k-space, and the order of the steps of phase encoding is not limited.

Figure 18:
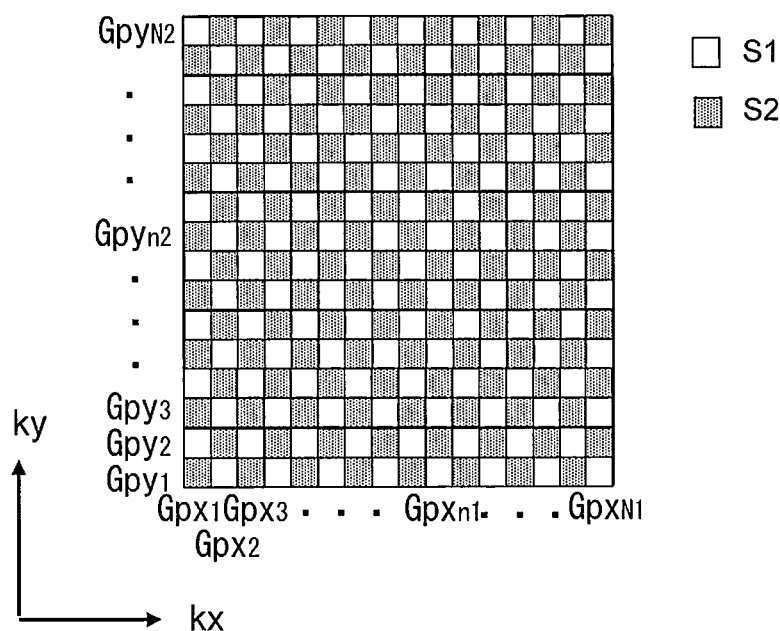
FIG. 18 is an explanatory diagram for explaining the k-t data obtained by the shifting water signal measurement processing in the case of shifting water signals for the xy-direction in the first embodiment.

FIG. 18 shows a k-space of k-t data at an arbitrary time for each receiver RF coil measured by executing a water shifting sequence according to the procedure shown in FIG. 17. In this drawing, S1 and S2 represent water signals intensity-modulated with the water selective pulses RFC1 and RFC2, respectively. In this drawing, intensities $Gpx_{n1}$ and $Gpy_{n2}$ of the phase encoding gradient magnetic fields applied in accordance with the coordinates $kx_{n1}$ of and $ky_{n2}$ for the kx- and ky-directions, respectively, are indicated on the axes of coordinates. In the k-t data at an arbitrary time obtained with the above water shifting sequence, S1 and S2 appear alternately in a line along the kx-direction and the ky-direction, as shown in this drawing.

Figure 19A:
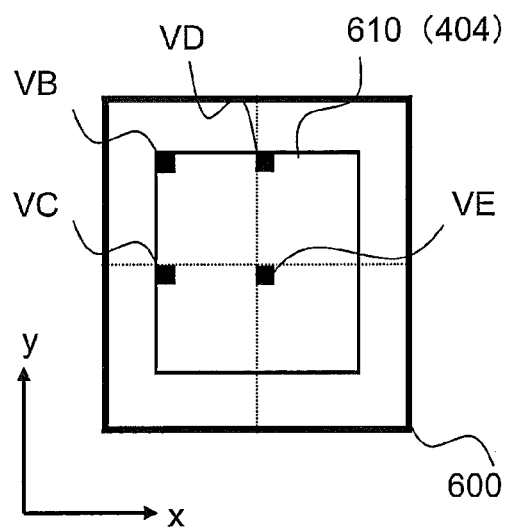
FIG. 19A is an explanatory diagram for explaining the water spectroscopic image in the case of shifting water signals for the xy-direction in the first embodiment, which shows a water spectroscopic image.
Figure 19B:
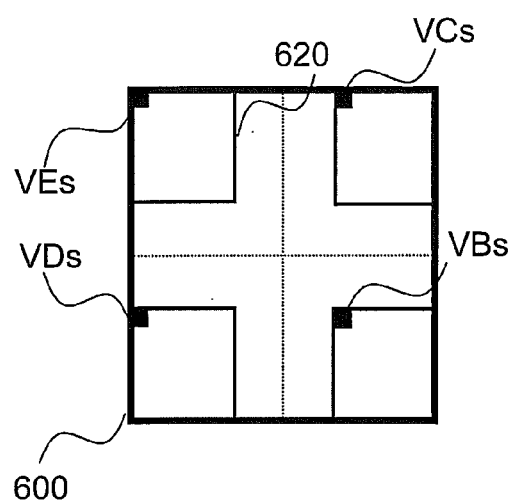
FIG. 19B is an explanatory diagram for explaining the water spectroscopic image in the case of shifting water signals for the xy-direction in the first embodiment, which shows a shifted water spectroscopic image.

In the spectroscopic image obtained by Fourier transform of the k-t data, water signals shift by ½ of the image in the x-direction and the y-direction. The shift of a water signal in this case is shown in FIGS. 19A and 19B. FIG. 19A shows sensitivity map of water signal without shift (water spectroscopic image) 610 in a field of view 600, and FIG. 19B show a shifted water spectroscopic image 620 in which the signals shift by ½ for the x-direction and ½ for the y-direction in the field of view 600. By the shift of water signals, voxels VB, VC, VD and VE on the sensitivity map of water signal (water spectroscopic image) 610 shift to VBs, VCs, VDs, and VEs on the shifted water spectroscopic image 620, respectively.

Figure 19C:
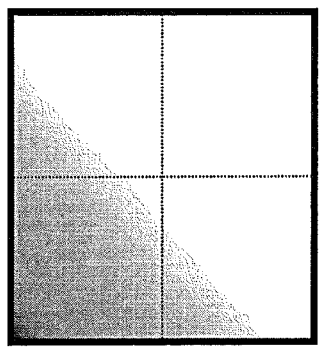
FIG. 19C is an explanatory diagram for explaining the water spectroscopic image in the case of shifting water signals for the xy-direction in the first embodiment, which shows a metabolite sensitivity map.
Figure 19D:
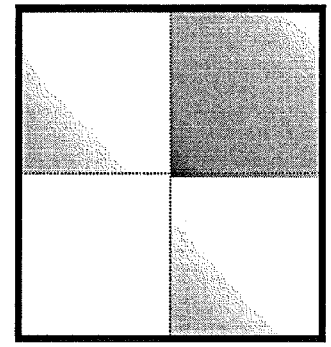
FIG. 19D is an explanatory diagram for explaining the water spectroscopic image in the case of shifting water signals for the xy-direction in the first embodiment, which shows a water sensitivity map.

Further, when the shifting direction is the xy-direction, the water sensitivity map $C_w$ is also calculated by shifting the metabolism sensitivity map (sensitivity map of receiver RF coil) $C_m$ for the xy-directions by ½, respectively. The metabolite sensitivity map $C_m$ of this case is shown in FIG. 19C, and the water sensitivity map $C_w$ of this case is shown in FIG. 19D.

Further, the shifting direction of water signal may be determined to be such a direction that SNR of the metabolite spectroscopic image is maximized by using g factor distribution (g factor map). The g factor distribution is an index for evaluating SNR of water and metabolite spectroscopic images calculated by the water and metabolite separation processing, and it is defined by the following equation (16) using the sensitivity matrix C.

[Equation 16]

$$g(n) = \sqrt{\text{diag}[(C^H C)^{-1}(C^H C)]} \quad (16)$$

here, $$C = \begin{bmatrix} C_m(a, x, y) & C_w(a, x, y) \\ C_m(b, x, y) & C_w(b, x, y) \end{bmatrix}$$

In the equation, diag[ ] represents a diagonal component of the matrix in [ ]. n is a natural number. When n=1, g factor distribution of a metabolite spectroscopic image $g_m$ (henceforth referred to simply as metabolite g factor distribution) is represented, and when n=2, g factor distribution of a shifted water spectroscopic image $g_{ws}$ (henceforth referred to simply as water shifted g factor distribution) is represented. Further, by performing shifted signal correction of $g_{ws}$, g factor distribution of a water spectroscopic image $g_w$ (henceforth referred to simply as water g factor distribution) can be calculated. The metabolite g factor distribution $g_m$ and the water shifted g factor distribution $g_{ws}$ are equivalent to each other. The g factor has a value of 1 or larger, and SNR in each voxel of metabolite and water spectroscopic images to be calculated is in inverse proportion to the g factor value.

When the shifting direction is determined by using the g factor distribution, g factor distributions are calculated by using three patterns of water sensitivity maps for the x-direction, the y-direction, and the xy-direction, and the shifting water signal measurement is performed with the shifting direction giving the smallest g factor value.

In addition, as in the acquisition of an inverse matrix of the sensitivity matrix C instead of $C^H C$ in the equation (16), a regularized matrix $CH\psi^{-1}C$ obtained by weighting with a noise correlation matrix $\psi$ of each RF coil may be used as described above.

Further, although this embodiment was explained by exemplifying a case of using a pulse sequence with which phase encoding is performed for two dimensions of the x- and y-directions as the main scan pulse sequence 300 of the water shifting sequence, the main scan pulse sequence 300 to be used may be a pulse sequence with which phase encoding is performed for three dimensions of the x-, y-, and z-directions. The selectable shifting directions of water signals in this case are in seven patterns of x, y, z, xy, yz, zx, and xyz directions. The shifting direction may be determined to be a direction giving the maximum SNR by using the g factor distributions also in this case.

Further, although the sensitivity maps of the receiver RF coils are calculated from the MRI image obtained beforehand in the aforementioned explanation of this embodiment, the present invention is not limited to such a configuration. For example, they may be calculated from an FID image itself obtained by the shifting signal measurement unit 210 with a water shifting sequence, in which only water signals shift. In such a case, a water sensitivity map $C_w$ is calculated from an arbitrary point for the direction of time in this FID image, and then a metabolite sensitivity map $C_m$ is calculated by shifting the water sensitivity map $C_w$.

Further, although this embodiment was explained above by exemplifying a case of separating images of water and arbitrary metabolite, the objective substances of the measurement are not limited to them. They may be two or more kinds of substances showing different chemical shifts, such as fat and metabolite, and different metabolites. Further, the substances to be separated are not limited to two kinds of substances, and may be three or more kinds of substances. This embodiment can be applied to a case where predetermined substances showing different chemical shifts can be selectively shifted on the image.

Second Embodiment

Hereafter, the second embodiment of the present invention will be explained. The MRI apparatus 100 of this embodiment has basically the same configuration as that of the first embodiment. In the first embodiment, signals in the same number as that in a desired image matrix are measured to obtain k-t data. On the other hand, in this embodiment, the measurement is performed with reducing the measurement points in a phase encoding axis different from the water signal shifting direction to obtain k-t data. Then, aliased signals on a spectroscopic image are returned by using RF coil sensitivity, and signals of water and metabolite are separated. Therefore, the measurement time can be further shortened according to the second embodiment compared with the first embodiment. Hereafter, this embodiment will be explained focusing on the configuration different from that of the first embodiment.

Figure 20:
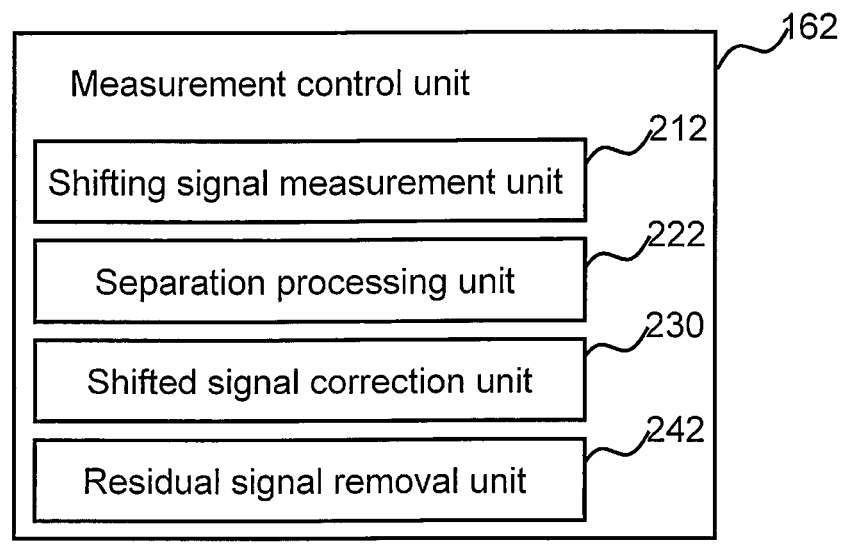
FIG. 20 is a functional block diagram of the measurement control unit according to the second embodiment.

A measurement control unit 162 of this embodiment has basically the same configuration as that of the first embodiment, as shown in FIG. 20. However, in this embodiment, the measurement is performed with reducing the measurement points for a phase encoding axis at the time of obtaining k-t data as described above, and therefore the functions of a shifting signal measurement unit 212, a separation processing unit 222, and a residual signal removal unit 242 are different. Hereafter, the details of the parts of the measurement control unit 162 of this embodiment will be explained.

The objective substances of the measurement are water and a metabolite as in the first embodiment. Further, the RF coils of the radio frequency magnetic field coil system 13 of this embodiment have a configuration having four receiver RF coils 31 to 34 as shown in FIG. 16.

First, the shifting signal measurement processing performed by the shifting signal measurement unit 212 of this embodiment will be explained. As in the first embodiment, the shifting signal measurement unit 212 of this embodiment realizes the shifting signal measurement processing by operating the RF pulse transmission unit 120, the signal reception unit 130, and the gradient magnetic field application unit 140 according to a pulse sequence stored beforehand, and making the image reconstruction unit 150 perform an image reconstruction processing.

The pulse sequence executed in the shifting signal measurement processing of this embodiment is basically the same as that of the first embodiment, and is a water shifting sequence having the pre-pulse sequence 310 for modulating only the longitudinal magnetization of water signals to a predetermined intensity, and the main scan pulse sequence 300 based on a region selective type MRSI pulse sequence for imaging signals from a desired region.

The shifting signal measurement unit 212 of this embodiment controls the water shifting sequence so that RFC1 and RFC2 are alternately irradiated as the water selective excitation pulses RFC of the pre-pulse sequence 310 in every one step of phase encoding in the main scan pulse sequence 300 to perform the shifting water signal measurement, as in the first embodiment.

For example, phase encoding gradient magnetic fields for the x- and y-directions are represented as Gp1 and Gp2, respectively, coordinates for the kx-direction and the ky-direction in the k-space are represented as $kx_{n1}$ and $ky_{n2}$, respectively, intensities of phase encoding gradient magnetic fields corresponding to them are represented as $Gpx_{n1}$ and $Gpy_{n2}$, respectively, and total numbers of the phase encoding steps of the first embodiment are represented as $N_1$ and $N_2$, respectively. $n_1$, $n_2$, $N_1$, and $N_2$ are natural numbers, and they satisfy the conditions of $n_1 \leq N_1$ and $n_2 \leq N_2$. Further, if $n_1$ and $n_2$ which make the intensities of the phase encoding gradient magnetic field $Gpx_{n1}$ and $Gpy_{n2}$ to be 0 are represented as $v_1$ and $v_2$, respectively, the position represented by k-space coordinates $(kx_{v1}, ky_{v2})$ is defined as the center ($k_0$) of the k-space.

Figure 21A:
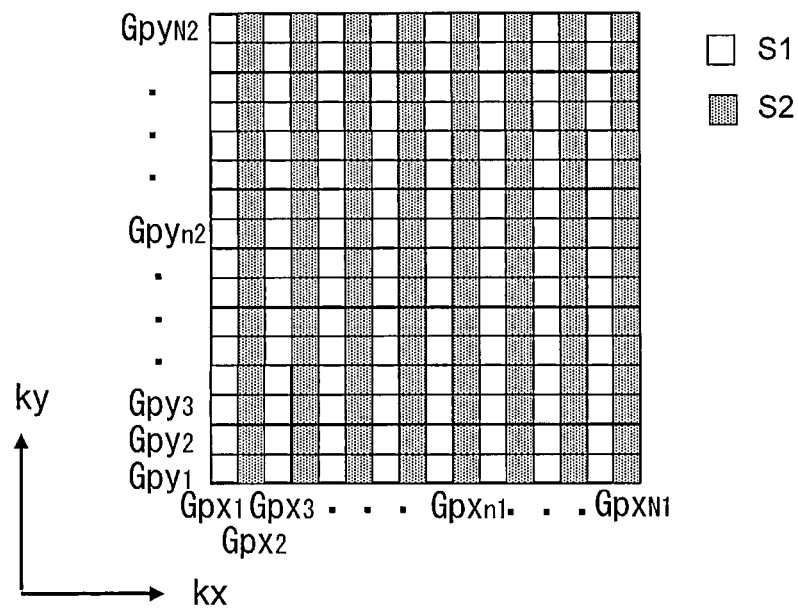
FIG. 21A is an explanatory diagram for explaining k-t data obtainable by the shifting water signal measurement processing according to the first embodiment.

In the first embodiment, the shifting signal measurement unit 210 controls the units so that when $n_1$ is an odd number, the water selective pulse RFC1 is irradiated, and when $n_1$ is an even number, the water selective pulse RFC2 is irradiated, for the kx-direction. Further, the measurement is performed without adding any particular change for the ky-direction to obtain k-t data with each of the receiver RF coils 31 to 34. The k-space of the k-t data obtained above at an arbitrary time is shown in FIG. 21A. In this drawing, S1 and S2 represent water signals intensity-modulated with the water selective pulses RFC1 and RFC2, respectively.

Figure 21B:
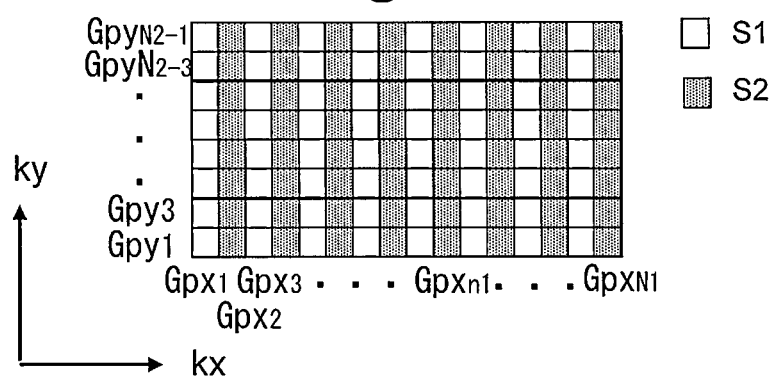
FIG. 21B is an explanatory diagram for explaining k-t data obtainable by the shifting water signal measurement processing according to the second embodiment.

On the other hand, in this embodiment, the shifting signal measurement unit 212 controls the units so that when $n_1$ is an odd number, the water selective pulse RFC1 is irradiated, and when $n_1$ is an even number, the water selective pulse RFC2 is irradiated, for the kx-direction. However, the measurement is performed with omitting, for example, the measurement points of even numbers of $n_2$ for the ky-direction to obtain k-t data with each of the receiver RF coils 31 to 34. The k-space of the k-t data obtained above at an arbitrary time is shown in FIG. 21B. In this drawing, S1 and S2 represent water signals intensity-modulated with the water selective pulses RFC1 and RFC2, respectively. Further, phase encoding gradient magnetic field intensities $Gpx_{n1}$ and $Gpy_{n2}$ are indicated along the coordinate axes.

Thus, in the k-t data at an arbitrary time obtained with the water shifting sequence of this embodiment, S1 and S2 appear alternately in a line along the kx-direction, and the signals of the same signal intensities appear in a line along the ky-direction, but signals are omitted for every second step for the ky-direction, as shown in FIG. 21B.

In addition, also in this embodiment, the shifting signal measurement unit 212 performs FFT of the k-t data obtained by shifting water signal measurement to obtain a spectroscopic image for each of the receiver RF coils 31 to 34.

Figure 22:
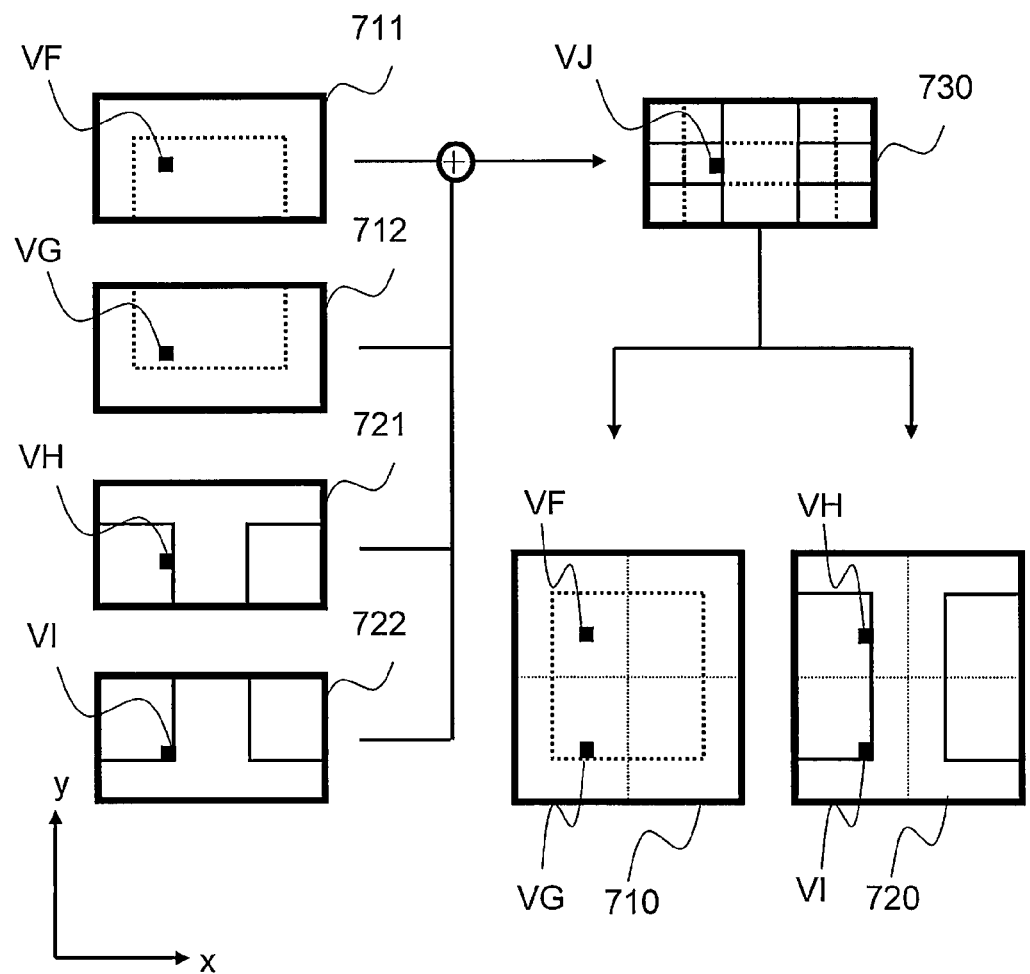
FIG. 22 is an explanatory diagram for explaining the spectroscopic image measured according to the second embodiment and the separation processing.

Hereafter, the separation processing performed by the separation processing unit 222 of this embodiment will be explained. In advance of explanation of the separation processing, a spectroscopic image of this embodiment obtained by the shifting signal measurement unit 212 of this embodiment will be explained with reference to FIG. 22. In FIG. 22, an image 711 and an image 712 represent upper part and lower part of a metabolite spectroscopic image 710, an image 721 and an image 722 represent upper part and lower part of a shifted water spectroscopic image 720, respectively. A spectroscopic image 730 to be measured is calculated as the sum of the images 711, 712, 721, and 722.

That is, in the spectroscopic image 730 measured by the shifting signal measurement unit 212 of this embodiment, water signals are shifted in the x-direction by shifting water signal measurement, and the image is aliased in the y-direction because the measurement is performed with reducing measurement points for the ky-direction. Therefore, a voxel VJ on the spectroscopic image 730 corresponds to the sum of voxels VF, VG, VH and VI of the same positions in the images 711, 712, 721, and 722.

The separation processing unit 222 of this embodiment also performs separation of the aliased signals, in addition to the separation of signals of water and metabolite similar to that of the first embodiment. Signals of voxels VM, VN, VO, and VP are thereby separated from the voxel VJ to eventually calculate the metabolite spectroscopic image 710 and the shifted water spectroscopic image 720.

The calculation is performed by using a water sensitivity map $C_w$ and a metabolite sensitivity map $C_m$. This water sensitivity map $C_w$ is calculated by shifting the sensitivity map of each of the receiver RF coils 31 to 34 (metabolite sensitivity map $C_m$) by ½ for the x-direction, as in the first embodiment.

If the metabolite spectroscopic image is represented as m, the shifted water spectroscopic image shifted by ½ for the x-direction on the image is represented as $w_s$, and for an arbitrary voxel (x, y) in each spectroscopic images obtained by measurement with the receiver RF coils 31 to 34, the metabolite sensitivity maps are represented as $C_m$ (a, x, y), $C_m$ (b, x, y), $C_m$ (c, x, y), and $C_m$ (d, x, y), respectively, water sensitivity maps $C_w$ are represented as $C_w$ (a, x, y), $C_w$ (b, x, y), $C_w$ (c, x, y), and $C_w$ (d, x, y), respectively, the metabolite signal is represented as m (x, y), the water shift signal is represented as $w_s$ (x, y), and the number of voxels for the y-direction is represented as $N_2$, signal intensities I (a, x, y), I (b, x, y), I (c, x, y), and I (d, x, y) of the voxel (x, y) in the spectroscopic images reconstructed from the echo signals measured with the receiver RF coils 31 to 34 are represented by the following equation (17).

[Equation 17]

$$\begin{bmatrix} I(a, x, y) \\ I(b, x, y) \\ I(c, x, y) \\ I(d, x, y) \end{bmatrix} = C \begin{bmatrix} m(x, y + N_2/2) \\ m(x, y) \\ w_s(x, y + N_2/2) \\ w_s(x, y) \end{bmatrix} \quad (17)$$

here, $$C = \begin{bmatrix} C_m(a, x, y+N_2/2) & C_m(a, x, y) & C_w(a, x, y+N_2/2) & C_w(a, x, y) \\ C_m(b, x, y+N_2/2) & C_m(b, x, y) & C_w(b, x, y+N_2/2) & C_w(b, x, y) \\ C_m(c, x, y+N_2/2) & C_m(c, x, y) & C_w(c, x, y+N_2/2) & C_w(c, x, y) \\ C_m(d, x, y+N_2/2) & C_m(d, x, y) & C_w(d, x, y+N_2/2) & C_w(d, x, y) \end{bmatrix}$$

Therefore, when the determinant of the sensitivity matrix C is not 0, the metabolite signal m (x, y) and the water shift signal $w_s$ (x, y) at each coordinate point (x, y) of the metabolite spectroscopic image m and the shifted water spectroscopic image $w_s$ are calculated in accordance with the following equations (18) by using the inverse matrix $C^{-1}$ of the sensitivity matrix C.

[Equation 18]

$$B = (C^H C)^{-1} C^H I \quad (18)$$

here, $$C = \begin{bmatrix} C_m(a, x, y+N_2/2) & C_m(a, x, y) & C_w(a, x, y+N_2/2) & C_w(a, x, y) \\ C_m(b, x, y+N_2/2) & C_m(b, x, y) & C_w(b, x, y+N_2/2) & C_w(b, x, y) \\ C_m(c, x, y+N_2/2) & C_m(c, x, y) & C_w(c, x, y+N_2/2) & C_w(c, x, y) \\ C_m(d, x, y+N_2/2) & C_m(d, x, y) & C_w(d, x, y+N_2/2) & C_w(d, x, y) \end{bmatrix},$$

$$B = \begin{bmatrix} m(x, y+N_2/2) \\ m(x, y) \\ w_s(x, y+N_2/2) \\ w_s(x, y) \end{bmatrix}, \quad I = \begin{bmatrix} I(a, x, y) \\ I(b, x, y) \\ I(c, x, y) \\ I(d, x, y) \end{bmatrix}$$

In the equation, m (x, y+$N_2$/2) and m (x, y) represent the upper part and the lower part of the metabolite spectroscopic image m, respectively. Further, $w_s$ (x, y+$N_2$/2) and $w_s$ (x, y) represent the upper part and the lower part of the shifted water spectroscopic image $w_s$, respectively.

By combining the upper part and the lower part of the obtained metabolite spectroscopic image m for the y-direction, the metabolite spectroscopic image m is calculated, and by combining the upper part and the lower part of the shifted water spectroscopic image $w_s$ for the y-direction, the shifted water spectroscopic image $w_s$ is calculated.

In addition, in this embodiment, the separation processing unit 222 may calculate the metabolite spectroscopic image m and the shifted water spectroscopic image $w_s$, respectively, by using a weighting operation using the noise correlation matrix $\psi$, as shown in the following equation (19).

[Equation 19]

$$B = (C^H \Psi^{-1} C)^{-1} C^H \Psi^{-1} I \quad (19)$$

A shifted signal correction unit 230 of this embodiment performs shifted signal correction for correcting a position for the shift amount shifted by the shifting water signal measurement for the calculated shifted water spectroscopic image $w_3$ to calculate the sensitivity map of water signal (water spectroscopic image) w, as in the first embodiment. In this embodiment, the calculation is performed with shifting by ½ of the image in the x-direction.

Next, the remaining water signal elimination processing performed by the residual signal removal unit 242 of this embodiment will be explained. Also in this embodiment, the residual signal removal unit 242 performs a remaining signal elimination processing as in the first embodiment. The procedure of the remaining signal elimination processing performed by the residual signal removal unit 242 of this embodiment is basically the same as that of the remaining signal elimination processing according to the first embodiment shown in FIG. 13. However, the simultaneous equation used in the elimination processing step S1203 is different.

First, the remaining water signal of this embodiment will be explained with reference to FIG. 23A, FIG. 23B and FIG. 23C. FIG. 23A shows a metabolite spectroscopic image m, FIG. 23B shows a shifted water spectroscopic image $w_s$ calculated by the separation processing, and FIG. 23C shows a water spectroscopic image w obtained by performing shifted signal correction of the shifted water spectroscopic image $w_s$. Further, signal intensities of water at a voxel VK (x, y) in the spectroscopic images are represented as mVK, wVK, and $w_s$VK, respectively, and signal intensities of water at a voxel VL (x, y+$N_2$/2) in the shifted water spectroscopic image $w_s$ and the water spectroscopic image w are represented as wVL and $w_s$VL, respectively.

As explained for the first embodiment, the remaining water signal mVK in the voxel VK of the metabolite spectroscopic image m contains remaining water signal due to errors occurring in the measurement and separation processing. In this embodiment, in particular, the separation processing unit 223 performs not only the separation of water signals and metabolite signals, but also separation of the aliased signals in the y-direction, and therefore the remaining water signal mVK in the voxel VK of the metabolite spectroscopic image m contains not only the water signal of the voxel VK, but also the aliased water signal of the voxel VL.

Therefore, the remaining water signal mVK in the voxel VK of the metabolite spectroscopic image m is represented by the following equation (20), wherein p, q, r, and s are proportionality constants.

$$mVK = p \times wVK + q \times w_s VK + r \times wVL + s \times w_s VL \quad (20)$$

Therefore, if the proportionality constants p, q, r and s in the equation (20) are obtained, intensity of the remaining water signal mVK of the metabolite spectroscopic image 631 can be obtained, and eliminated.

These proportionality constants p, q, r and s are calculated by the least square method for every voxel from FID images $m_t$, $w_t$, and $w_{st}$ obtained by FFT of the metabolite spectroscopic image m, the water spectroscopic image w, and the shifted water spectroscopic image $w_s$ in the spectrum direction, as in the first embodiment.

If the number of measurement points for the time direction is represented as T, the relation of the FID images $m_t$, $w_t$, and $w_{st}$ of each voxel (x, y) is represented by the simultaneous linear equation (21).

[Equation 21]

$$\begin{bmatrix} m_t(t_1, x, y_i) \\ m_t(t_2, x, y_i) \\ \vdots \\ m_t(t_T, x, y_i) \end{bmatrix} = \quad (21)$$

$$\begin{bmatrix} w_t(t_1, x, y_i) & w_{st}(t_1, x, y_i) & w_t(t_1, x, y_j) & w_{st}(t_1, x, y_j) \\ w_t(t_2, x, y_i) & w_{st}(t_2, x, y_i) & w_t(t_2, x, y_j) & w_{st}(t_2, x, y_j) \\ \vdots & \vdots & \vdots & \vdots \\ w_t(t_T, x, y_i) & w_{st}(t_T, x, y_i) & w_t(t_T, x, y_j) & w_{st}(t_T, x, y_j) \end{bmatrix} \begin{bmatrix} p \\ q \\ r \\ s \end{bmatrix}$$

When $y_i \leq N_2/2$, $y_j = y_i + N_2/2$, and when $y_i > N_2/2$, $y_j = y_i - N_2/2$.

The residual signal removal unit 242 of this embodiment calculates the proportionality constant p, q, r and s as described above. Then, by using the calculated proportionality constant p, q, r and s, it calculates the remaining water signal mVK of the voxel VK (x, y), and subtracts the calculated remaining water signal mVK from the FID image $m_t$ obtained according to the equation (21) to calculate the FID image $m_{ct}$ after elimination of the remaining signal.

Further, the residual signal removal unit 242 performs Fourier transform (FFT) of the FID image $m_{ct}$ after elimination of the remaining signal to obtain the metabolite spectroscopic image in which the remaining water signal mVK is eliminated.

Also in this embodiment, this residual signal removal unit 242 may not be provided.

The process flows of the measurement control processing performed by the parts of the aforementioned measurement control unit 162 of this embodiment are the same as those of the first embodiment.

As explained above, according to this embodiment, the same effect as that of the first embodiment can be obtained. Further, in this embodiment, the measurement is performed with reducing the number of measurement points for a phase encoding axis different from the water signal shifting direction to obtain k-t data. Therefore, measurement time is shortened to ½ compared with the first embodiment. Accordingly, images of two or more kinds of substances showing different chemical shifts can be obtained at higher speed.

The modifications of the first embodiment are also applicable to this embodiment. For example, the number of the receiver RF coils may be four or larger. Further, the shape and disposition of the receiver RF coils are not limited so long as an inverse matrix is available for the sensitivity matrix calculated on the basis of the sensitivity maps of the receiver RF coils. The shifting direction of water signal is not also limited so long as an inverse matrix is available for the sensitivity matrix, as in the first embodiment. The shifting direction may be determined by using the g factor distribution. Further, the shift amount of each substance as the object of measurement is not limited to that mentioned above, either. Furthermore, the pulse sequence may be a pulse sequence with which three-dimensional phase encoding is performed. The sensitivity map of each receiver RF coil may also be calculated from an FID image in which only water signals are shifted, not from an MRI image obtained beforehand. Types and number of types of the substance as the object of measurement are not limited, either, so long as the chemical shifts thereof are different.

Third Embodiment

Hereafter, the third embodiment of the present invention will be explained. The MRI apparatus 100 of this embodiment has basically the same configuration as that of the second embodiment. In the second embodiment, the measurement is performed with reducing the number of measurement points for a phase encoding axis different from the water signal shifting direction to obtain k-t data. However, in this embodiment, the measurement is performed with reducing the number of measurement points for a phase encoding axis the same as the water signal shifting direction to obtain k-t data. Then, on the basis of RF coil sensitivity, aliased signals on the spectroscopic image are returned, and signals of water and metabolite are separated. Hereafter, this embodiment will be explained focusing on the configuration different from that of the second embodiment.

Figure 24:
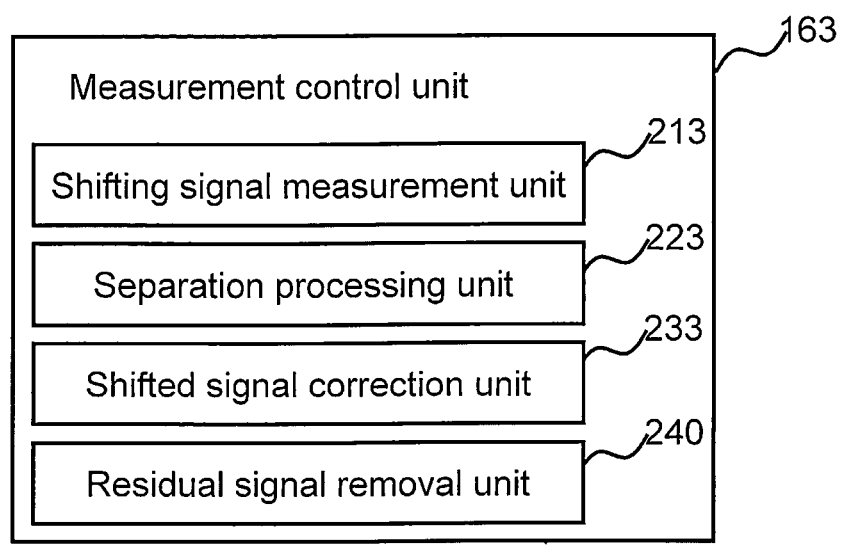
FIG. 24 is a functional block diagram of the measurement control unit according to the second embodiment.

A measurement control unit 163 of this embodiment has basically the same configuration as that of the second embodiment, as shown in FIG. 24. However, in this embodiment, the direction of the phase encoding axis for which the number of the measurement points is reduced at the time of obtaining k-t data is different as described above, and therefore functions of a shifting signal measurement unit 213, a separation processing unit 223, and a shifted signal correction unit 233 are different. Hereafter, the details of the units will be explained.

The objective substances of the measurement are water and a metabolite as in the second embodiment. Further, the RF coils of the radio frequency magnetic field coil system 13 of this embodiment have a configuration having four receiver RF coils 31 to 34 as shown in FIG. 16.

First, the shifting signal measurement processing performed by the shifting signal measurement unit 213 of this embodiment will be explained. As in the second embodiment, the shifting signal measurement unit 213 of this embodiment realizes the shifting signal measurement processing by operating the RF pulse transmission unit 120, the signal reception unit 130, and the gradient magnetic field application unit 140 according to an imaging pulse sequence stored beforehand, and making the image reconstruction unit 150 perform an image reconstruction processing.

The pulse sequence executed in the shifting signal measurement processing of this embodiment is basically the same as that used in the second embodiment, and is a water shifting sequence having the pre-pulse sequence 310 for modulating only the longitudinal magnetization of water signals to a predetermined intensity, and the main scan pulse sequence 300 based on a region selective type MRSI pulse sequence for imaging signals from a desired region.

The shifting signal measurement unit 213 of this embodiment controls the water shifting sequence so that RFC1 and RFC2 are alternately irradiated as the water selective excitation pulses RFC of the pre-pulse sequence 310 in every one step of phase encoding in the main scan pulse sequence 300 to perform the shifting water signal measurement.

For example, phase encoding gradient magnetic fields for the x- and y-directions are represented as Gp1 and Gp2, respectively, coordinates for the kx-direction and the ky-direction in the k-space are represented as $kx_{n1}$ and $ky_{n2}$, respectively, intensities of phase encoding gradient magnetic fields corresponding to them are represented as $Gpx_{n1}$ and $Gpy_{n2}$, respectively, and total numbers of the phase encoding steps of the first embodiment are represented as $N_1$ and $N_2$, respectively. $n_1$, $n_2$, $N_1$, and $N_2$ are natural numbers, and they satisfy the conditions of $n_1 \leq N_1$ and $n_2 \leq N_2$. Further, if $n_1$ and $n_2$ which make the intensities of the phase encoding gradient magnetic fields $Gpx_{n1}$ and $Gpy_{n2}$ to be 0 are represented as $v_1$ and $v_2$, respectively, the position represented by k-space coordinates ($kx_{v1}$, $ky_{v2}$) is defined as the center ($k_0$) of the k-space.

Figure 25A:
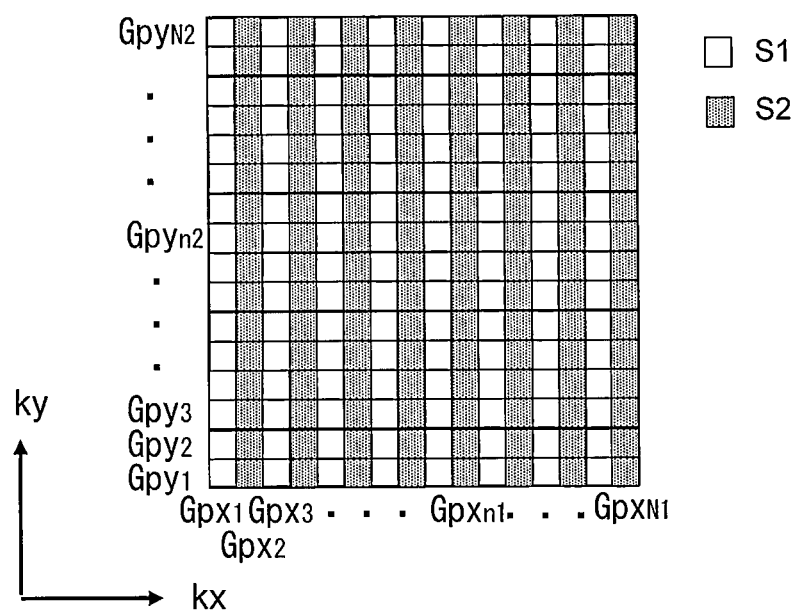
FIG. 25A is an explanatory diagram for explaining k-t data obtainable by the shifting water signal measurement processing according to the first embodiment.

In the first embodiment, the shifting signal measurement unit 210 performs such control that when $n_1$ is an odd number, the water selective pulse RFC1 is irradiated, and when $n_1$ is an even number, the water selective pulse RFC2 is irradiated, for the kx-direction. Further, the measurement is performed without adding any particular change for the ky-direction to obtain k-t data with each of the receiver RF coils 31 to 34. The k-space of the k-t data obtained above at an arbitrary time is shown in FIG. 25A. In this drawing, S1 and S2 represent water signals intensity-modulated with the water selective pulses RFC1 and RFC2, respectively.

Figure 25B:
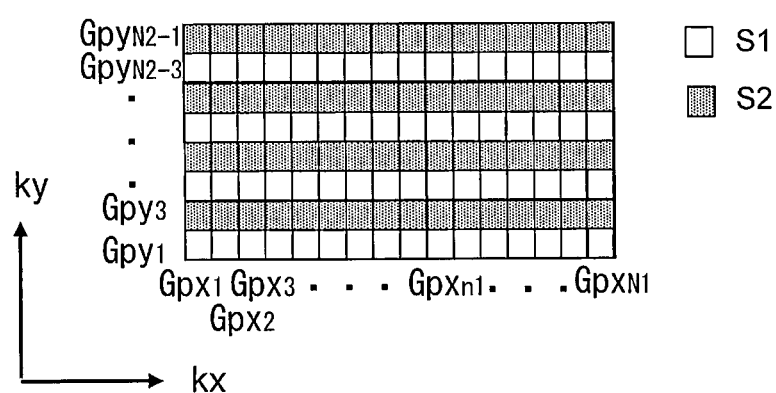
FIG. 25B is an explanatory diagram for explaining k-t data obtainable by the shifting water signal measurement processing according to the third embodiment.

On the other hand, in this embodiment, the shifting signal measurement unit 213 performs the measurement without adding any particular change for the kx-direction, but for the ky-direction, it performs the measurement with omitting the measurement points of which $n_2$ is an even number, so that when $n_2$ is 1, 5, 9 ... $4_{n2}-3$, ..., the water selective pulse RFC1 is irradiated, and when $n_2$ is 3, 7, 11 ... $4n_2-1$, ..., the water selective pulse RFC2 is irradiated, to obtain k-t data with each of the receiver RF coils 31 to 34. The k-space of the k-t data obtained above at an arbitrary time is shown in FIG. 25B. In this drawing, S1 and S2 represent water signals intensity-modulated with the water selective pulses RFC1 and RFC2, respectively. Further, phase encoding gradient magnetic field intensities $Gpx_{n1}$ and $Gpy_{n2}$ are indicated along the coordinate axes.

Thus, in the k-t data at an arbitrary time obtained with the water shifting sequence of this embodiment, S1 and S2 appear alternately in a line along the ky-direction for every second step, and the signals of the same signal intensities appear in a line along the kx-direction, as shown in FIG. 25B.

In addition, also in this embodiment, the shifting signal measurement unit 213 performs FFT for each of the k-t data obtained by shifting water signal measurement to obtain a spectroscopic image for each of the receiver RF coils 31 to 34.

Figure 26:
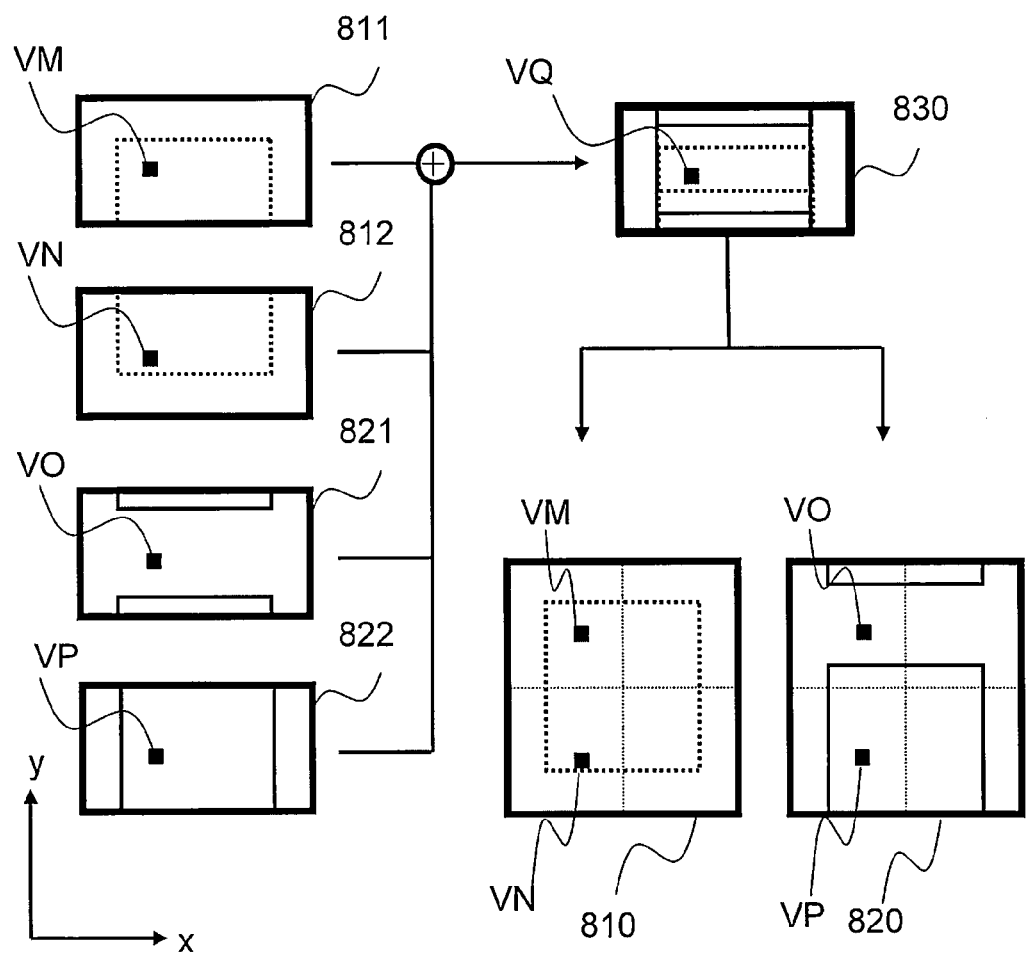
FIG. 26 is an explanatory diagram for explaining a spectroscopic image measured according to the third embodiment and the separation processing.

Hereafter, the separation processing performed by the separation processing unit 223 of this embodiment will be explained. In advance of explanation of the separation processing, a spectroscopic image of this embodiment obtained by the shifting signal measurement unit 213 of this embodiment according to the aforementioned procedure will be explained with reference to FIG. 26. In FIG. 26, an image 811 and an image 812 represent upper part and lower part of a metabolite spectroscopic image 810, an image 821 and an image 822 represent upper part and lower part of a shifted water spectroscopic image 820, respectively. A spectroscopic image 830 to be measured is calculated as the sum of the images 811, 812, 821, and 822.

That is, in the spectroscopic image 830 measured by the shifting signal measurement unit 213 of this embodiment, the image is aliased in the y-direction because the measurement is performed with reducing measurement points for the ky-direction, and water signals are shifted for the y-direction by the shifting water signal measurement. Therefore, a voxel VQ on the spectroscopic image 830 corresponds to the sum of voxels VM, VN, VO and VP of the same positions in the images 811, 812, 821, and 822.

The separation processing unit 223 of this embodiment also performs separation of the aliased signals, in addition to the separation of signals of water and metabolite, as the separation processing, as in the second embodiment. Signals of voxels VM, VN, VO, and VP are thereby separated from the voxel VQ, and the metabolite spectroscopic image 810 and the shifted water spectroscopic image 820 are eventually calculated.

The calculation is performed by using water sensitivity map $C_w$ and metabolite sensitivity map $C_m$. This water sensitivity map $C_w$ is calculated by shifting the sensitivity map of each of the receiver RF coils 31 to 34 (metabolite sensitivity map $C_m$) by $-\frac{1}{4}$ for the y-direction.

If the metabolite spectroscopic image is represented as m, the shifted water spectroscopic image shifted by $-\frac{1}{4}$ for the y-direction on the image is represented as $w_s$, and for an arbitrary voxel (x, y) in the spectroscopic images obtained by measurement with the receiver RF coils 31 to 34, the metabolite sensitivity maps are represented as $C_m$ (a, x, y), $C_m$ (b, x, y), $C_m$ (c, x, y), and $C_m$ (d, x, y), respectively, water sensitivity maps $C_w$ are represented as $C_w$ (a, x, y), $C_w$ (b, x, y), $C_w$ (c, x, y), and $C_w$ (d, x, y), respectively, the metabolite signal is represented as m (x, y), the water shift signal is represented as $w_s$ (x, y), and the number of voxels for the y-direction is represented by $N_2$, when the determinant of the sensitivity matrix C is not 0, the metabolite signal m (x, y) and the water shift signal $w_s$ (x, y) at each coordinate point (x, y) of the metabolite spectroscopic image m and the shifted water spectroscopic image w, shifted by $-\frac{1}{4}$ for the y-direction on the image are calculated from signal intensities I (a, x, y), I (b, x, y), I (c, x, y), and I (d, x, y) of the voxels (x, y) in the spectroscopic images reconstructed from the echo signals measured with the receiver RF coils 31 to 34 by using the inverse matrix $C^{-1}$ of the matrix C in accordance with the equation (18) or (19), as in the second embodiment.

The shifted signal correction unit 233 of this embodiment performs shifted signal correction for correcting positions for the shift amount shifted by the shifting water signal measurement for the calculated shifted water spectroscopic image $w_s$ to calculate the sensitivity map of water signal (water spectroscopic image) w, as in the first embodiment. However, in the shifted signal correction of this embodiment, when the shifted signal correction is performed on the image, shifting is performed by $+\frac{1}{4}$ of the image in the y-direction. When the water selective pulse RFC2 is irradiated at the k-space center $k_0$ in the shifting water signal measurement, after shifting by $+\frac{1}{4}$ of the image in the y-direction, $-1$ is multiplied. On the other hand, when the shifted signal correction processing is performed on the k-space, phase $+\pi/2$ is multiplied at each point for the ky-direction by using the equation (1).

The remaining signal elimination processing performed by the residual signal removal unit 243 of this embodiment is the same as that of the second embodiment. Further, the residual signal removal unit may not be provided, like the aforementioned embodiments.

Further, the process flow of the measurement control processing performed by the units of the aforementioned measurement control unit 163 of this embodiment is the same as that of the aforementioned embodiments.

As explained above, according to this embodiment, the same effect as that of the second embodiment can be obtained. Further, this embodiment can also be applied to, for example, a case where a pulse sequence of which phase encoding direction is limited, such as a pulse sequence for EPSI (Echo-Planar Spectroscopic Imaging), is used as the main scan pulse sequence 300. Therefore, according to this embodiment, the same effect as that of the second embodiment can be obtained irrespective of the pulse sequence used for the main scan.

The modifications of the first embodiment are also applicable to this embodiment. For example, the number of the receiver RF coils may be four or larger. Further, the shape and disposition of the receiver RF coil are not limited so long as an inverse matrix is available for the sensitivity matrix calculated on the basis of the sensitivity map of the receiver RF coil. The shifting direction of water signal is not also limited so long as an inverse matrix is available for the sensitivity matrix, as in the first embodiment. The shifting direction may be determined by using the g factor distribution. Further, the shift amount of each substance as the object of measurement is not limited to that mentioned above, either. Furthermore, the pulse sequence may be a pulse sequence with which three-dimensional phase encoding is performed. The sensitivity map of each receiver RF coil may also be calculated from an FID image in which only water signals are shifted, not from an MRI image obtained beforehand. Types and number of types of the substances as the objects of measurement are not limited, either, so long as the chemical shifts thereof are different.

The aforementioned embodiments were explained by exemplifying a case of using a basic MRSI pulse sequence shown in FIG. 5 as the main scan pulse sequence 300. However, the pulse sequence used for the main scan pulse sequence 300 is not limited to such a pulse sequence. For example, pulse sequences for FSE type high-speed MRSI or oscillating gradient magnetic field type high-speed MRSI may also be used.

Figure 27:
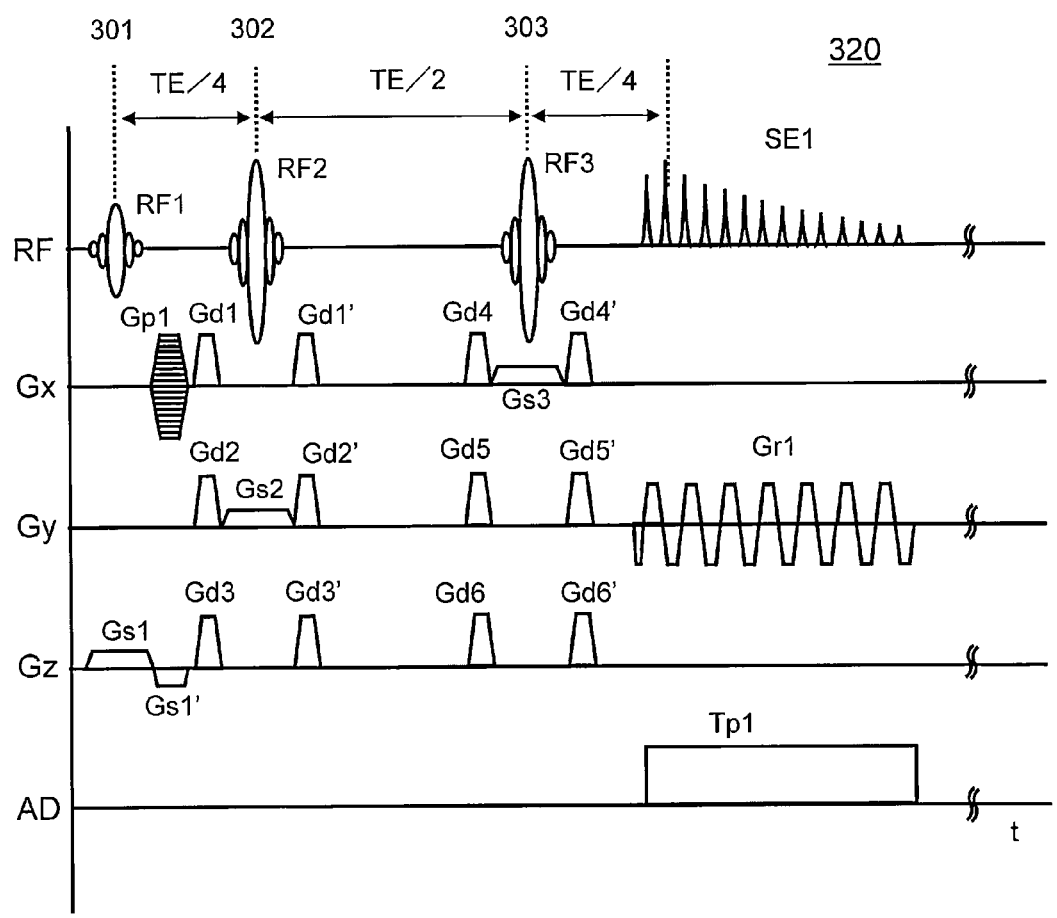
FIG. 27 is a sequence chart of another example of the main scan pulse sequence used in the embodiments of the present invention.

FIG. 27 shows an example of high-speed MRSI pulse sequence with oscillating gradient magnetic field 320. In the high-speed MRSI pulse sequence with oscillating gradient magnetic field 320 shown in this drawing, an oscillating gradient magnetic field Gr1 is applied instead of the phase encoding gradient magnetic field Gp2 of the MRSI pulse sequence 300 shown in FIG. 5. By receiving signals with applying the oscillating gradient magnetic field Gr1, signals SE1 frequency-encoded for the application axis direction are obtained as time series data.

However, when the high-speed MRSI pulse sequence with oscillating gradient magnetic field 320 is used as the main scan pulse sequence 300, the phase encoding gradient magnetic field is applied along one axis, and therefore the direction for shifting water signals is limited to the two directions of x- and y-directions. For example, as explained for the first embodiment, the g factor distribution is calculated, and the direction giving the maximum SNR among the x-direction and y-direction is determined to be the phase encoding direction to perform the measurement.

The high-speed MRSI pulse sequence with oscillating gradient magnetic field 320 shown in FIG. 27 is an example of a pulse sequence for two-dimensional measurement of which phase encoding direction is the x-direction. However, an high-speed MRSI pulse sequence with oscillating gradient magnetic field for three-dimensional measurement using phase encoding for two directions among the x, y, and z-directions may be used for the main scan. In this case, patterns of the selectable shifting directions of water signals are six patterns of x, y, z, xy, yz, and zx directions. Also in this case, the direction giving the maximum SNR may be determined to be the shifting direction.

Although the first to third embodiments were explained by exemplifying a case where the shift amount for the substance as the object of measurement to be shifted is ½ of the number of data points for each direction on the image. However, the shift amounts for the substances as the objects of measurement are not limited to such an amount. It is sufficient that the shift amounts are different so that the separation is enabled.

As explained above, in the aforementioned first to third embodiments, the signal reception unit is provided with receiver RF coils in a number not smaller than number of types of substances to be separated, and arranges the received magnetic resonance signals in a k-space different for every receiver RF coil, and the measurement control unit is provided with a shifting signal measurement unit which obtains a measured image for every receiver RF coil with spatially shifting signals of substances as objects of measurement on the image by different amounts of shift, the separation processing unit which separates measured images obtained with the shifting signal measurement unit into measured images of two or more kinds of the substances by using sensitivity maps of the receiver RF coils, and the shifted signal correction unit which corrects the shift amounts in the measured images for the substances obtained after the separation with the separation processing unit.

For example, the shifting signal measurement unit may execute an imaging sequence having a pre-pulse sequence for irradiating a frequency-selective pulse which intensity-modulates only the longitudinal magnetization of each substance among the two or more kinds of substances, and control the imaging sequence so that the frequency selective pulse is irradiated alternately with two kinds of different flip angles for every phase encoding performed with the main scan sequence.

For example, two kinds of the different flip angles of the frequency selective pulse may be those having positive and negative opposite polarities and giving the same absolute values of the longitudinal magnetization of the substance to be intensity-modulated with the frequency selective pulse after the intensity modulation.

For example, the measurement control unit may be further provided with a residual signal removal unit which eliminates signals of one or more kinds of substances remaining in signals of another substance in the measured image.

For example, the shifting signal measurement unit may obtain a measured image for every receiver RF coil with shifting each substance for the direction giving the maximum SNR, and the shifting direction may be determined by using a g factor map, which is calculated from a sensitivity map of each of the receiver RF coils and serves as an index of SNR.

Furthermore, two kinds of the different flip angles of the frequency selective pulse may be, for example, 0 degree, and a value of degree giving 0 of longitudinal magnetization of the substance to be intensity-modulated with the frequency selective pulse after the intensity modulation.

Further, for example, the sensitivity maps used by the separation processing unit may be prepared in the number of types of substances as the objects of measurement according to the shift amounts of the substances as the objects of measurement.

Fourth Embodiment

Hereafter, the fourth embodiment of the present invention will be explained. In the first embodiment, a water spectroscopic image and a metabolite spectroscopic image of the same field of view as the field of view of the spectroscopic image obtained by shifting water signal measurement are calculated. However, in this embodiment, the field of view of the spectroscopic image obtained by the shifting water signal measurement similar to that of the first embodiment is developed twice for each axial direction (henceforth simply expressed as developed twice), signals of water and metabolite are separated, and a water spectroscopic image and a metabolite spectroscopic image of the doubled field of view are calculated.

For example, when signals of water and metabolites including a substance showing a high signal intensity such as subcutaneous fat are separated, signals of the subcutaneous fat existing out of the field of view of shifting water signal measurement are aliased and contained in the metabolite spectroscopic image after the separation. The signals of the outside of the field of view aliased and contained in the metabolite spectroscopic image can be eliminated by developing the field of view twice. Therefore, according to this embodiment, in a case where signals existing outside of the field of view of the shifting water signal measurement are aliased and contained in the metabolite spectroscopic image, signals of water and metabolite can be separated with eliminating such aliased signals.

In advance of explanation of this embodiment, the phenomenon that signals existing outside the field of view of shifting water signal measurement are aliased and contained in the signals inside the field of view (wraparound phenomenon) will be explained with reference to FIG. 28A and FIG. 28B. In FIG. 28A, a broken line 901 represents subcutaneous fat, a dotted line 902 represents a region of interest, and a solid line 903 represents a field of view. A voxel VAA is a voxel locating in the region of interest 902, and a voxel VAB is a voxel locating in the subcutaneous fat 901 and outside of the field of view. Hereafter, the aliasing phenomenon will be explained by exemplifying a usual region selective type MRSI measurement performed with sufficiently suppressing water signals, not the shifting water signal measurement of this embodiment, for simplicity of the explanation.

When the region of interest 902 is excited in the region selective type MRSI measurement, the irradiation time of RF pulse is limited, and therefore the excitation profile is not a perfectly rectangular profile, but an excitation profile gently rising and having a side lobe. The subcutaneous fat 901 locating in the voxel VAB is also slightly excited by this side lobe.

FIG. 28B is a schematic diagram representing the region selective type MRSI measurement performed for the field of view 903. As shown in FIG. 28B, the signal of the voxel VAB is aliased and contained in the voxel VAA. Since the signal intensity of subcutaneous fat is usually several hundreds to several thousands times higher than that of metabolites, the signal intensity of subcutaneous fat to be included is so strong that it affects the signals of metabolites, even when the side lobe of the excitation profile is small. Therefore, when the excitation profile is not perfectly rectangular, subcutaneous fat signals of high signal intensity are contained to degrade diagnostic ability.

According to this embodiment, fat signals aliased in the field of view are developed to the doubled field of view to separate water and metabolite signals. Therefore, even when subcutaneous fat signals out of the field of view are excited and included due to the inaccuracy of the excitation profile, inclusion of subcutaneous fat signals unnecessary for the diagnosis can be prevented, and diagnostic ability can be improved.

Hereafter, this embodiment will be explained focusing on the configuration different from that of the first embodiment. The MRI apparatus 100 of this embodiment has basically the same configuration as that of the first embodiment. Further, as shown in FIG. 29, the configuration of the measurement control unit 164 of this embodiment is also basically the same as that of the first embodiment.

However, in this embodiment, as described above, when the substances as the objects of measurement are separated, they are also developed into a doubled field of view. Therefore, processing performed by the separation processing unit 224 is different from that of the first embodiment. In connection with this difference, the processing performed by the shifted signal correction unit 234 also differs from that of the first embodiment.

The radio frequency magnetic field coil system 13 of this embodiment simultaneously measures signals of two or more kinds of substances of different resonance frequencies, and separates them in the reconstructed images, basically as in the first embodiment. Furthermore, a aliased and overlapped region is also separated in this embodiment. Also in this embodiment, the sensitivity maps of the receiver RF coils are used for this separation. Therefore, in this embodiment, the receiver RF coils are required at least in a number of regions to be separated for every substance to be separated ("number of substances to be separated" x "number of regions to be separated").

Hereafter, the details of the parts of the measurement control unit 164 of this embodiment will be explained. The objective substances of the measurement are water and a metabolite as in the first embodiment.

First, the shifting signal measurement processing performed by the shifting signal measurement unit 210 of this embodiment will be explained. The shifting signal measurement unit 210 of this embodiment spatially shifts signals of two or more kinds of substances as the objects of measurements by different amounts of shift on the image to obtain a measured image for every receiver RF coil. As in the first embodiment, the shifting signal measurement unit 210 of this embodiment realizes the shifting signal measurement processing by operating the RF pulse transmission unit 120, the signal reception unit 130, and the gradient magnetic field application unit 140 according to a pulse sequence stored beforehand, and making the image reconstruction unit 150 perform an image reconstruction processing.

The pulse sequence executed in the shifting signal measurement processing of this embodiment is the same as that of the first embodiment, and is a water shifting sequence having a pre-pulse sequence 310 for modulating only the longitudinal magnetization of water signals to a predetermined intensity, and the main scan pulse sequence 300 based on a region selective type MRSI pulse sequence for imaging signals from a desired region.

The shifting signal measurement unit 210 of this embodiment controls the water shifting sequence so that RFC1 and RFC2 are alternately irradiated as the water selective excitation pulses RFC of the pre-pulse sequence 310 in every one step of phase encoding in the main scan pulse sequence 300 to perform the shifting water signal measurement, as in the first embodiment.

Hereafter, this embodiment will be explained by exemplifying a case where the shifting signal measurement unit 210 performs the shifting water signal measurement in which the shifting direction shown in FIGS. 17 and 18 is the xy-direction.

Also in this embodiment, the shifting signal measurement unit 210 performs FFT of the k-t data obtained by the shifting water signal measurement, respectively, to obtain a spectroscopic image for each of a plurality of the receiver RF coils.

Figure 30:
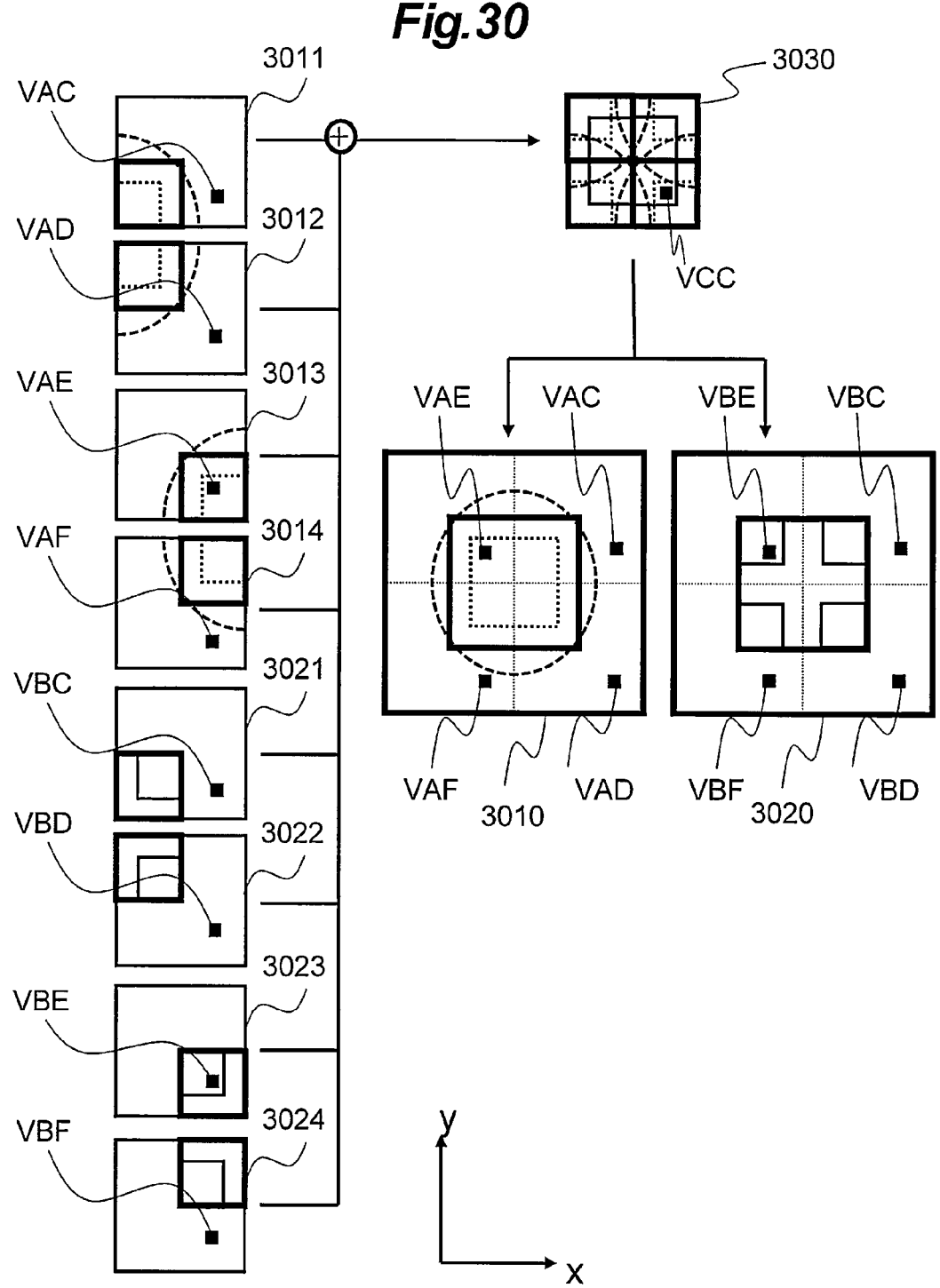
FIG. 30 is an explanatory diagram for explaining configuration of a spectroscopic image obtained by the shifting signal measurement unit according to the fourth embodiment.

Hereafter, a spectroscopic image to be obtained by the shifting signal measurement unit 210 of this embodiment will be explained with reference to FIG. 30. In FIG. 30, images 3011, 3012, 3013, and 3014 represent upper right region (upper right part), lower right region (lower right part), upper left region (upper left part), and lower left region (lower left part) of a metabolite spectroscopic image 3010 of a field of view twice larger than the field of view of the shifting water signal measurement. Further, images 3021, 3022, 3023, and 3024 represent upper right part, lower right part, upper left part, and lower left part of a shifted water spectroscopic image 3020 of a field of view twice larger than the field of view of the shifting water signal measurement. Hereafter, the field of view of the shifting water signal measurement is referred to simply as field of view, and the field of view twice larger than the field of view of the shifting water signal measurement is referred to as double field of view.

A spectroscopic image 3030 to be measured is the sum of the images 3011, 3012, 3013, 3014, 3021, 3022, 3023, and 3024, as shown in FIG. 30.

That is, the voxel VCC on the spectroscopic image 3030 measured by the shifting signal measurement unit 210 of this embodiment is the sum of the voxels VAC, VAD, VAE, VAF, VBC, VBD, VBE, and VBF of the same positions on the images 3011, 3012, 3013, 3014, 3021, 3022, 3023, and 3024.

The separation processing unit 224 of this embodiment performs separation of aliased signals as well as separation of signals of water and metabolite as in the first embodiment, as the separation processing described later. The separation processing unit 224 of this embodiment thereby separates the signals of the voxels VAC, VAD, VAE, VAF, VBC, VBD, VBE, and VBF from the signals of the voxel VCC, and finally calculates the metabolite spectroscopic image 3010 and the shifted water spectroscopic image 3020 of double field of view.

Thus, in this embodiment, four regions are separated. Further, two kinds of substances, water and metabolite, are separated. Therefore, the radio frequency magnetic field coil system 13 of this embodiment is provided with at least $4\times2=8$ of the receiver RF coils.

Hereafter, the configuration of the receiver RF coils of the radio frequency magnetic field coil system 13 of this embodiment will be explained. The radio frequency magnetic field coil system 13 explained here is provided with eight receiver RF coils 41, 42, 43, 44, 45, 46, 47, and 48 shown in FIG. 31.

Each of these eight receiver RF coils 41 to 48 has a shape of about ⅛ of a circle in a plane parallel to the xy plane, and they are disposed so as to form a cylindrical shape as a whole. The receiver RF coils 41 to 48 are separately connected to the amplifier 18, and measured radio frequency signals are separately obtained.

In this drawing, the RF coil for transmission and the detuning circuit are omitted for simplicity of the drawing. Further, in this example, eight of the receiver RF coils 41 to 48 are indicated so that ends of the constituent conductors of adjacent receiver RF coils are at the same position or contact with each other, but the configuration is not limited to such a configuration. For example, they may be disposed so that parts of adjacent receiver RF coils overlap each other in the side of the cylindrical shape of the receiver RF coils 41 to 48.

Figure 31:
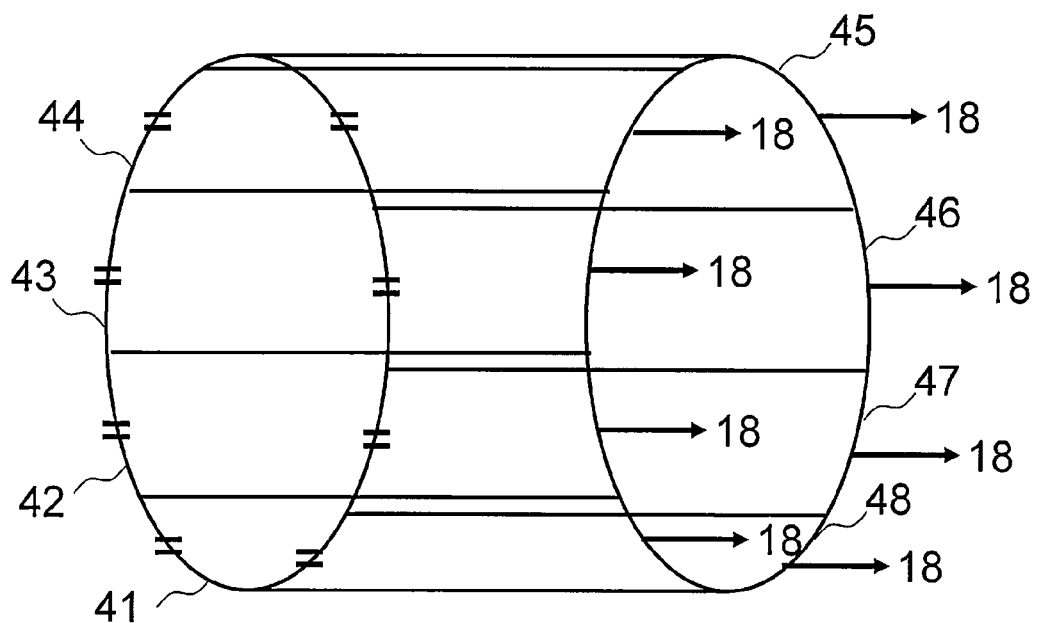
FIG. 31 is an explanatory diagram for explaining configuration of the receiver RF coil according to the fourth embodiment.

The shape and disposition of these eight of the receiver RF coils 41 to 48 are not limited to those shown in FIG. 31. It is sufficient that an inverse matrix of the sensitivity matrix C calculated on the basis of sensitivity maps of these eight of the receiver RF coils 41 to 48 is available, and various modifications may be possible.

Hereafter, the separation processing performed by the separation processing unit 224 of this embodiment will be explained. The separation processing unit 224 of this embodiment also separates the measured image obtained by the shifting signal measurement unit 210 into measured images for two or more kinds of substances as in the first embodiment by using sensitivity maps of the receiver RF coils. Further, in this embodiment, at the time of the separation, the measured image obtained with each of the receiver RF coils is developed into an image of a field of view having a double size (double field of view) for each axis direction to calculate a measured image for every substance. Further, the sensitivity maps to be used are prepared in the number of types of the substances as the objects of measurement. Then, a standard substance is chosen from the substances as the objects of measurement. Standard substance sensitivity map as the sensitivity map of this standard substance is created by shifting the sensitivity map of the double field of view for every receiver RF coil created beforehand according to the shift amount of the standard substance. The sensitivity maps of the other substances in the objects of measurement are each created as a sensitivity map of double field of view by extracting a sensitivity map of the size of the field of view from the standard substance sensitivity map, shifting the extracted sensitivity map according to a relative shift amount of each substance as the object of measurement based on the shift amount of the standard substance, and performing 0 padding of the region other than the extracted region. When the sensitivity map of the field of view size is extracted from the standard substance sensitivity map, it is extracted so that the profiles have the same center, and corresponding sides of the profiles are parallel to each other. In this embodiment, the signal reception unit 130 is at least provided with the receiver RF coils in the number of regions to be developed and separated for every substance to be separated.

That is, also in this embodiment, the sensitivity map is prepared for every substance as the object of measurement, and the separation processing is performed by using it. In this embodiment, the objective substances of the separation are water and metabolite, and therefore the separation processing unit 224 creates water sensitivity map $C_w$ and metabolite sensitivity map $C_m$ of the double field of view from sensitivity maps of the double field of view of the receiver RF coils obtained beforehand. Then, by using these created sensitivity maps, the metabolite spectroscopic image 3010 and the shifted water spectroscopic image 3020 of the double field of view are calculated. In this embodiment, the aforementioned standard substance is the metabolite. Since the metabolite is not shifted, the sensitivity map of the double field of view of the receiver RF coil obtained beforehand is used as it is as the metabolite sensitivity map $C_m$.

Figure 32:
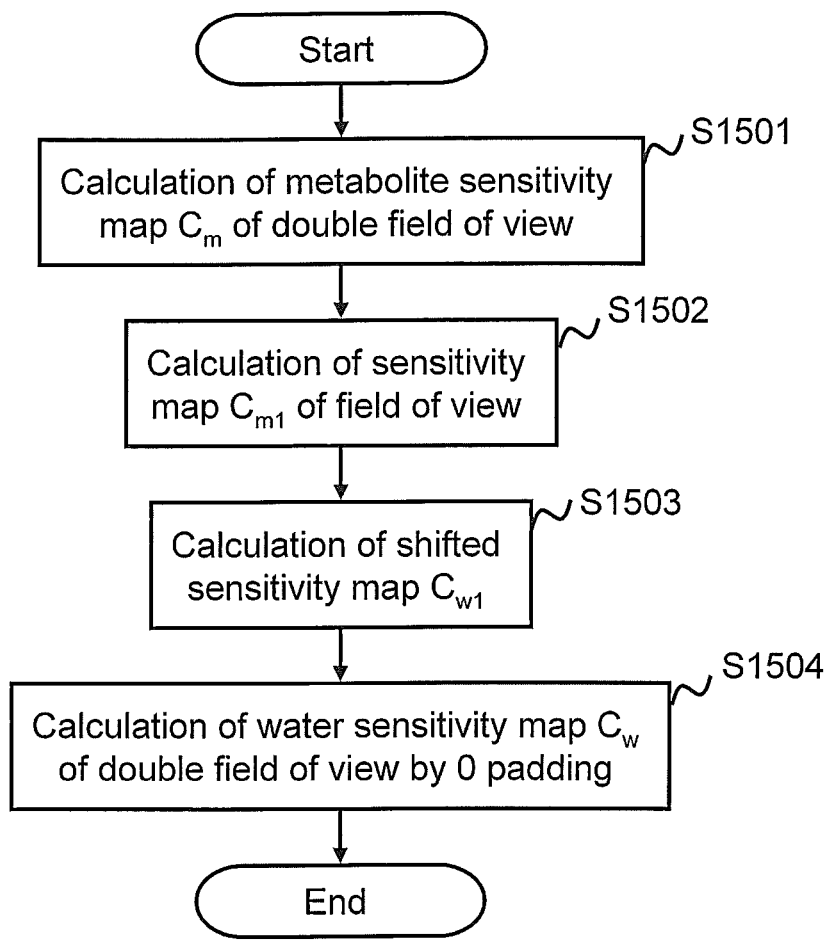
FIG. 32 is a flowchart of the sensitivity map calculation processing according to the fourth embodiment.

First, procedure of the calculation of the water sensitivity map $C_w$ and the metabolite sensitivity map $C_m$ performed by the separation processing unit 224 of this embodiment will be explained with reference to FIGS. 32 and 33. Hereafter, methods for calculation of the water sensitivity map $C_w$ and the metabolite sensitivity map $C_m$ of the receiver RF coil 41 will be explained as examples. FIG. 32 shows the process flow for preparing the sensitivity maps performed by the separation processing unit 224 of this embodiment. Further, in FIG. 33A, FIG. 33B, FIG. 33C and FIG. 33D, the field of view and the double field of view are indicated with reference numerals 3101 and 3102, respectively.

Figure 33A:
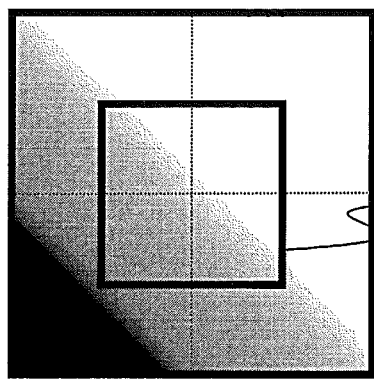
FIG. 33A is an explanatory diagram for explaining the sensitivity map calculation processing according to the fourth embodiment, which shows a metabolite sensitivity map in double field of view.

First, the metabolite sensitivity map $C_m$ of the double field of view 3102 is calculated (S1501). This metabolite sensitivity map $C_m$ is calculated in a manner similar to that of the generally known sensitivity map calculating method, as in the first embodiment, as described above. This metabolite sensitivity map $C_m$ is shown in FIG. 33A.

Figure 33B:
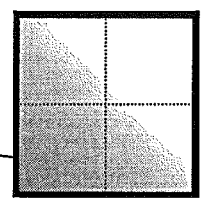
FIG. 33B is an explanatory diagram for explaining the sensitivity map calculation processing according to the fourth embodiment, which shows a cut-out metabolite sensitivity map.

Then, the metabolite sensitivity map $C_m$ is cut down to the size of the field of view 3101 of the shifting water signal measurement, and a sensitivity map $C_{m1}$ of the field of view 3101 is calculated (S1502). The obtained sensitivity map $C_{m1}$ is shown in FIG. 33B.

Figure 33C:
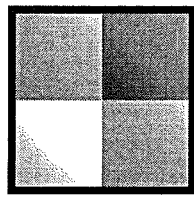
FIG. 33C is an explanatory diagram for explaining the sensitivity map calculation processing according to the fourth embodiment, which shows a shifted water sensitivity map.

Then, the sensitivity map $C_{m1}$ is shifted by the sift amount of water in the shifting water signal measurement to calculate a shifted sensitivity map $C_{m1}$ shifted by the same shift amount as that of the shifting water signal measurement (S1503). In the example of this embodiment, the sensitivity map $C_{m1}$ is shifted for the x-direction and the y-direction by ½ of the field of view 3101 for the shifting water signal measurement, respectively. The obtained sensitivity map $C_{w1}$ is shown in FIG. 33C.

Figure 33D:
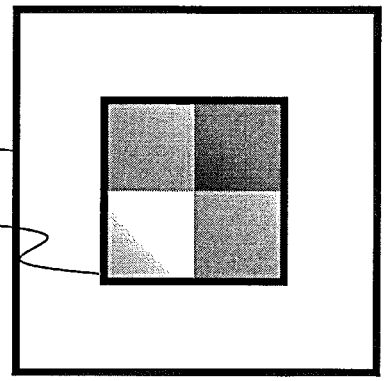
FIG. 33D is an explanatory diagram for explaining the sensitivity map calculation operation according to the fourth embodiment, which shows a water sensitivity map in double field of view.

Finally, 0 padding is performed for the region of the double imaging view 3102 other than the field of view 3101 of the sensitivity map $C_{w1}$ to calculate water sensitivity map $C_w$ of the double field of view 3102 (S1504). The obtained water sensitivity map $C_w$ of the double field of view is shown in FIG. 33D.

Similar calculations are performed for the receiver RF coils 42, 43, 44, 45, 46, 47, and 48 to obtain the metabolite sensitivity map and water sensitivity map of the double field of view 3102 for every receiver RF coil.

Hereafter, the separation processing performed by the separation processing unit 224 using the water sensitivity map $C_w$ and the metabolite sensitivity map $C_m$ by will be explained. As described above, signal intensity of an arbitrary voxel in a spectroscopic image reconstructed from echo signals measured with each of the receiver RF coils 41 to 48 is obtained by adding the signals of the four regions for each substance to be separated, developed into the double field of view, and multiplied with weights according to the sensitivity of each of the receiver RF coils 41 to 48.

That is, if a metabolite spectroscopic image of a double field of view is represented as M, a shifted water spectroscopic image is represented as $W_s$ for arbitrary voxels $r_1$ (x, y) on the spectroscopic images obtained by measurement for the receiver RF coils 41 to 48, metabolite sensitivity maps are represented as $C_m(c_1, x, y), C_m(c_2, x, y), C_m(c_3, x, y), C_m(c_4, x, y), C_m(c_5, x, y), C_m(c_6, x, y), C_m(c_7, x, y)$ and $C_m(c_8, x, y)$, respectively, water sensitivity maps are represented as $C_w(c_1, x, y), C_w(c_2, x, y), C_w(c_3, x, y), C_w(c_4, x, y), C_w(c_5, x, y), C_w(c_6, x, y), C_w(c_7, x, y)$ and $C_w(c_8, x, y)$, respectively, metabolite signal is represented as M (x, y), water shift signal is represented as $W_s$ (x, y), and the numbers of voxels for the x-direction and the y-direction are represented as $N_1$ and $N_2$, respectively, the signal intensities at the voxel $r_1$ (x, y) in the spectroscopic images reconstructed from the echo signals measured with the receiver RF coils 41 to 48, $I(c_1, x, y), I(c_2, x, y), I(c_3, x, y), I(c_4, x, y), I(c_5, x, y), I(c_6, x, y), I(c_7, x, y)$, and $I(c_8, x, y)$ are represented by the following equation (22).

[Equation 22]

$$\begin{bmatrix} I(c_1, r_1) \\ I(c_2, r_1) \\ I(c_3, r_1) \\ I(c_4, r_1) \\ I(c_5, r_1) \\ I(c_6, r_1) \\ I(c_7, r_1) \\ I(c_8, r_1) \end{bmatrix} = C \begin{bmatrix} M(r_1) \\ M(r_2) \\ M(r_3) \\ M(r_4) \\ W_s(r_1) \\ W_s(r_2) \\ W_s(r_3) \\ W_s(r_4) \end{bmatrix} \quad (22)$$

here, $$C = \begin{bmatrix} C_m(c_1, r_1) & \cdots & C_m(c_1, r_4) & C_w(c_1, r_1) & \cdots & C_w(c_1, r_4) \\ \vdots & \ddots & \vdots & \vdots & \ddots & \vdots \\ C_m(c_8, r_1) & \cdots & C_m(c_8, r_4) & C_w(c_8, r_1) & \cdots & C_w(c_8, r_4) \end{bmatrix}$$

$r_1 = (x, y), r_2 = (x + N_1, y), r_3 = (x, y + N_2), r_4 = (x + N_1, y + N_2)$

Therefore, when the determinant of the sensitivity matrix C is not 0, the metabolite signal M (x, y) and the water shift signal $W_s$ (x, y) at the coordinate point (x, y) of the metabolite spectroscopic image M of the double field of view and the shifted water spectroscopic image $W_s$ are calculated in accordance with the following equation (23) by using the inverse matrix $C^{-1}$ of the sensitivity matrix C.

[Equation 23]

$$B = C^{-1} I \quad (23)$$

here, $$C = \begin{bmatrix} C_m(c_1, r_1) & \cdots & C_m(c_1, r_4) & C_w(c_1, r_1) & \cdots & C_w(c_1, r_4) \\ \vdots & \ddots & \vdots & \vdots & \ddots & \vdots \\ C_m(c_8, r_1) & \cdots & C_m(c_8, r_4) & C_w(c_8, r_1) & \cdots & C_w(c_8, r_4) \end{bmatrix}$$

$$B = \begin{bmatrix} M(r_1) \\ M(r_2) \\ M(r_3) \\ M(r_4) \\ W_s(r_1) \\ W_s(r_2) \\ W_s(r_3) \\ W_s(r_4) \end{bmatrix}, I = \begin{bmatrix} I(c_1, r_1) \\ I(c_2, r_1) \\ I(c_3, r_1) \\ I(c_4, r_1) \\ I(c_5, r_1) \\ I(c_6, r_1) \\ I(c_7, r_1) \\ I(c_8, r_1) \end{bmatrix}$$

$r_1 = (x, y), r_2 = (x + N_1, y), r_3 = (x, y + N_2),$
$r_4 = (x + N_1, y + N_2)$

M (x, y+$N_2$), M (x, y), M (x+$N_1$, y+$N_2$), and M (x+$N_1$, y) represent the upper left part, the lower left part, the upper right part, and the lower right part of the metabolite spectroscopic image M of the double field of view, respectively. Further, $W_s$ (x, y+$N_2$), $W_s$ (x, y), $W_s$ (x+$N_1$, y+$N_2$), and $W_s$ (x+$N_1$, y) represent the upper left part, the lower left part, the upper right part, and the lower right part of the shifted water spectroscopic image $W_s$ of the double field of view, respectively.

The upper left part, the lower left part, the upper right part, and the lower right part of the obtained metabolite spectroscopic image M are combined for the x-direction and the y-direction to calculate the metabolite spectroscopic image M of the double field of view, and the upper left part, the lower left part, the upper right part, and the lower right part of the shifted water spectroscopic image $W_s$ are combined for the x-direction and the y-direction to calculate the shifted water spectroscopic image $W_s$ of the double field of view.

However, the method for calculating the metabolite spectroscopic image M and the shifted water spectroscopic image $W_s$ of the double field of view is not limited to the aforementioned method. For example, they may be calculated by a weighting operation using the noise correlation matrix $\psi$ mentioned in the following equation (24).

[Equation 24]

$$B = (C^H \Psi^{-1} C)^{-1} C^H \Psi^{-1} I \quad (24)$$

Hereafter, the shifted signal correction processing performed by the shifted signal correction unit 234 of this embodiment will be explained. The shifted signal correction unit 234 of this embodiment corrects shift amounts in the measured image for every substance obtained after the separation performed by the separation processing unit 224, as in the first embodiment. In this operation of this embodiment, an image corresponding to the field of view before the development is further cut out from the measured image after the development.

That is, the shifted signal correction unit 234 of this embodiment first performs a field of view cutting-out processing for cutting out (extracting) parts of the obtained metabolite spectroscopic image M and the shifted water spectroscopic image $W_s$ of the double field of view in a size of the field of views. By performing this field of view cutting-out processing, the shifted signal correction unit 234 of this embodiment calculates the metabolite spectroscopic image m and the shifted water spectroscopic image $w_s$.

Then, the shifted signal correction, in which the positions are corrected by the shift amounts shifted in the shifting water signal measurement, is performed for the calculated shifted water spectroscopic image $w_s$, as in the first embodiment, to calculate the sensitivity map of water signal (water spectroscopic image) w. In this embodiment, the shifting is performed for the x-direction and the y-direction by ½ of the image.

The field of view cutting-out processing, which is performed by the shifted signal correction unit 234 of this embodiment, may be performed by the separation processing unit 224. In such a case, the shifted signal correction unit 234 performs only correction of shift amount like the shifted signal correction unit 230 of the first embodiment.

This embodiment may also use a configuration that the residual signal removal unit 240 is provided to eliminate remaining water signals, as in the first embodiment. Similarly, this residual signal removal unit 240 may not be provided.

The other configurations of the measurement control unit 164 of this embodiment are the same as those of the first embodiment. Therefore, the process flow of the measurement control processing performed by the parts of the measurement control unit 164 of this embodiment is the same as that of the first embodiment.

As explained above, according to this embodiment, the signal reception unit 130 is at least provided with the receiver RF coils in a number not smaller than the number of the types of the substances to be separated, and arranges the received magnetic resonance signal in a different k-space for every receiver RF coil, and the measurement control unit 164 is provided with the shifting signal measurement unit 210 which obtains a measured image for every receiver RF coil with spatially shifting signals of substances as objects of measurement on the image by different amounts of shift, the separation processing unit 224 which separates measured images obtained with the shifting signal measurement unit 210 into measured images of two or more kinds of the substance by using sensitivity maps of the receiver RF coils, and the shifted signal correction unit 234 which corrects the shift amounts in the measured images for the substances obtained after the separation performed by the separation processing unit 220.

Therefore, the same effect as that of the first embodiment can be obtained according to this embodiment. Furthermore, in this embodiment, the separation processing unit 224 develops the measured image for every receiver RF coil into a field of view twice as large as the field of view to calculate a measured image for every substance, the shifting signal measurement unit 234 further extracts an image corresponding to the field of view before the development from the measured image after the development, and the signal reception unit 130 is at least provided with receiver RF coils in a number of regions to be developed and separated for every substance to be separated.

Therefore, according to this embodiment, when signals of a substance having such a strong intensity that signals of a substance as an object of measurement are affected are excited out of the field of view due to inaccuracy of excitation profile in the region selective type MRSI, such signals of strong intensity aliased into the field of view can be eliminated by the development into the double field of view, thereby quality of the images to be obtained can be improved, and thus the diagnostic ability can be enhanced. When the object of measurement is a metabolite, the signals out of the field of view and having such a strong intensity that signals of a substance as an object of measurement are affected are, for example, signals of subcutaneous fat. In this case, inclusion of signals of subcutaneous fat unnecessary for diagnosis can be prevented by developing the fat signals aliased into the field of view into the double field of view, and thereby diagnostic ability can be improved.

The modifications of the first embodiment are also applicable to this embodiment. For example, the shifting direction of water signal is not also limited so long as an inverse matrix is available for the aforementioned sensitivity matrix, as in the first embodiment. The shifting direction may be determined by using the g factor distribution. Further, the pulse sequence may be a pulse sequence with which three-dimensional phase encoding is performed. The sensitivity map of each receiver RF coil may also be calculated from an FID image in which only water signals are shifted, not only from an MRI image obtained beforehand. Further, although this embodiment was explained by exemplifying a case where the substances as the objects of measurements were water and a metabolite, the substances as the object of measurement are not limited to them. Further, the number of types of the substances as the objects of measurement is not limited to the above number, either. Furthermore, although this embodiment was explained by exemplifying a case where the shift amount of the metabolite is 0, and the shift amount of water is ½ of data numbers for each direction of the image, the shift amounts of the substances as the objects of measurement are not limited to those mentioned above, either.

When the number of types of the substances as the objects of measurement is three or larger, one substance used as a standard is chosen, and sensitivity map of a double field of view prepared by a known method is used for the sensitivity map of the substance as the object of measurement used as a standard as shown in FIG. 33A. However, when the sensitivity map of the substance used as the standard is shifted, the sensitivity map for the double field of view prepared by a known method is shifted by the same shift amount. For the other substances as the objects of measurement, the sensitivity map of the substance as the object of measurement used as the standard is used as the sensitivity map of FIG. 33A, and sensitivity maps are prepared from it by the method explained with reference to FIG. 33A. In this case, as the shift amount, relative shift amounts based on the shift amount of the substance as the object of measurement used as the standard are used.

That is, the sensitivity maps used by the separation processing unit 224 are created in a number of types of the substances as the objects of measurement. Then, one of the substances as the objects of measurement is determined to be the standard substance. The standard substance sensitivity map as the sensitivity map of the standard substance is prepared by shifting the sensitivity map of the double field of view prepared beforehand according to the shift amount of the standard substance. The sensitivity maps of the other substances as the objects of measurement are prepared as sensitivity maps of the double field of view by extracting the sensitivity map of the field of view from the standard substance sensitivity map, shifting the extracted sensitivity map according to the relative shift amount of each substance as the object of measurement based on the shift amount of the standard substance, and performing 0 padding.

DENOTATION OF REFERENCE NUMERALS

10: Object of measurement, 11: static magnetic field generating magnet, 12: gradient magnetic field generating coil, 13: radio frequency magnetic field coil system, 14: control device, 15: gradient magnetic field power supply, 16: synthesizer, 17: modulator, 18: amplifier, 19: AD converter, 20: computer, 21: transmitter RF coil, 22: receiver RF coil, 23: receiver RF coil, 24: detuning circuit, 25: detuning circuit, 26: detuning circuit, 31: receiver RF coil, 32: receiver RF coil, 33: receiver RF coil, 34: receiver RF coil, 41: receiver RF coil, 42: receiver RF coil, 43: receiver RF coil, 44: receiver RF coil, 45: receiver RF coil, 46: receiver RF coil, 47: receiver RF coil, 48: receiver RF coil, 100: MRI apparatus, 101: MRI apparatus, 102: MRI apparatus, 110: static magnetic field generating unit, 120: RF pulse irradiation unit, 130: signal detection unit, 140: gradient magnetic field application unit, 150: image reconstruction unit, 160: measurement control unit, 162: measurement control unit, 163: measurement control unit, 164: measurement control unit, 210: shifting signal measurement unit, 212: shifting signal measurement unit, 213: shifting signal measurement unit, 220: separation processing unit, 222: separation processing unit, 223: separation processing unit, 224: separation processing unit, 230: shifted signal correction unit, 233: shifted signal correction unit, 234: shifted signal correction unit, 240:

residual signal removal unit, 242: residual signal removal unit, 300: main scan pulse sequence, 301: high-speed MRSI pulse sequence with oscillating gradient magnetic field, 302: pulse center, 303: pulse center, 310: pre-pulse sequence, 320: pulse center, 401: section, 402: section, 403: section, 404: region of interest, 410: axial image, 420: sagittal image, 430: coronal image, 501: signal intensity map of water and metabolite, 520: sensitivity map, 522: metabolite spectroscopic image, 523: water spectroscopic image, 524: spectroscopic image, 530: sensitivity map, 532: metabolite spectroscopic image, 533: water spectroscopic image, 534: spectroscopic image, 540: shifted sensitivity map, 541: sensitivity map of shifted water signal, 600: field of view, 610: sensitivity map of water signal, 620: sensitivity map of shifted water signal, 630: spectroscopic image, 710: metabolite spectroscopic image, 711: upper part of metabolite spectroscopic image, 712: lower part of metabolite spectroscopic image, 720: shifted water spectroscopic image, 721: upper part of shifted water spectroscopic image, 722: lower part of shifted water spectroscopic image, 810: metabolite spectroscopic image, 811: upper part of metabolite spectroscopic image, 812: lower part of metabolite spectroscopic image, 820: shifted water spectroscopic image, 821: upper part of shifted water spectroscopic image, 822: lower part of shifted water spectroscopic image, 830: spectroscopic image, 901: subcutaneous fat, 902: region of interest, 903: field of view, 3010: metabolite spectroscopic image, 3011: upper right part of metabolite spectroscopic image, 3012: lower right part of metabolite spectroscopic image, 3013: upper left part of metabolite spectroscopic image, 3014: lower left part of metabolite spectroscopic image, 3020: shifted water spectroscopic image, 3021: upper right part of shifted water spectroscopic image, 3022: lower right part of shifted water spectroscopic image, 3023: upper left part of shifted water spectroscopic image, 3024: lower left part of shifted water spectroscopic image, 3030: measured spectroscopic image, 3101: field of view, 3102: double field of view.

The invention claimed is:

1. A magnetic resonance imaging apparatus comprising
a static magnetic field generating unit which generates a static magnetic field in a space in which a subject is placed;
a transmission unit which transmits a radio frequency magnetic field pulse to the subject;
a reception unit which receives magnetic resonance signals generated from the subject;
a gradient magnetic field application unit which applies a phase encoding gradient magnetic field for adding positional information to the magnetic resonance signals;
an image reconstruction unit which reconstructs an image from the magnetic resonance signals received by the reception unit; and
a measurement control unit which controls operations of the transmission unit, the reception unit, the gradient magnetic field application unit, and the image reconstruction unit to obtain a measured image: wherein
the reception unit comprises receiver RF coils in a number not smaller than number of two or more kinds of substances as objects of measurement, and arranges the received magnetic resonance signals in a different k-space for every receiver RF coil; and
the measurement control unit comprises:
a shifting signal measurement unit which obtains a measured image for every receiver RF coil with spatially shifting signals of substances as objects of measurement on the image by different amounts of shift;
a separation unit which separates measured images obtained with the shifting signal measurement unit into measured images of two or more kinds of the substance by using sensitivity maps of the receiver RF coils; and
a shifted signal correction unit which corrects the shift amounts in the measured images of the substances obtained after the separation with the separation unit.

2. The magnetic resonance imaging apparatus according to claim 1, wherein
the shifting signal measurement unit executes an imaging sequence having a pre-pulse sequence for irradiating a frequency selective pulse for intensity-modulating only the longitudinal magnetization of two or more kinds of the substances and a main scan sequence, for each of the substances; and
the imaging sequence is controlled so that the frequency selective pulse is alternately irradiated with two kinds of different flip angles in the pre-pulse sequence for every phase encoding in the main scan sequence.

3. The magnetic resonance imaging apparatus according to claim 2, wherein
two kinds of the different flip angles of the frequency selective pulse have positive and negative opposite polarities, and values giving the same absolute values of the longitudinal magnetization of the substance to be intensity-modulated with the frequency selective pulse after the intensity modulation.

4. The magnetic resonance imaging apparatus according to claim 1, wherein
the measurement control unit further comprises a residual signal removal unit which eliminates signals of other substances remaining in signals of one kind of substance in the measured image.

5. The magnetic resonance imaging apparatus according to claim 1, wherein
the shifting signal measurement unit obtains a measured image for every receiver RF coil with shifting each substance for the direction giving the maximum SNR, and
the shifting direction is determined by using a g factor map, which is calculated from a sensitivity map of each of the receiver RF coils and serves as an index of SNR.

6. The magnetic resonance imaging apparatus according to claim 1, wherein
the shifting signal measurement unit performs the measurement with a reduced number of times of phase encoding; and
the separation unit further eliminates aliasing on the measured image for every receiver RF coil using sensitivity map of each of the receiver RF coils.

7. The magnetic resonance imaging apparatus according to claim 2, wherein
two kinds of the different flip angles of the frequency selective pulse are 0 degree, and a degree giving 0 of longitudinal magnetization of the substance to be intensity-modulated with the frequency selective pulse after the intensity modulation.

8. The magnetic resonance imaging apparatus according to claim 2, wherein
two kinds of the different flip angles of the frequency selective pulse are 0 degree, and 180 degrees.

9. The magnetic resonance imaging apparatus according to claim 6, wherein the axis for which the measurement is performed with a reduced number of times of phase encoding is determined by using a g factor map calculated from the sensitivity map of each of the receiver RF coils and serving as an index of SNR.

10. The magnetic resonance imaging apparatus according to claim 1, wherein
the separation unit calculates the sensitivity map from the measured image for every receiver RF coil obtained by the shifting signal measurement unit.

11. The magnetic resonance imaging apparatus according to claim 2, wherein
the main scan sequence is a magnetic resonance spectroscopic imaging sequence or an echo-planar spectroscopic imaging sequence.

12. The magnetic resonance imaging apparatus according to claim 1, wherein
two or more kinds of the substances are water and a metabolite; and
the shift amount of the metabolite is 0.

13. The magnetic resonance imaging apparatus according to claim 1, wherein
the sensitivity map used by the separation unit is created in a number of types of substances as the objects of measurement according to the shift amount of each of the substances as the objects of measurement.

14. The magnetic resonance imaging apparatus according to claim 1, wherein
the separation unit calculates a measured image for every substance by developing a measured image for every receiver RF coil into a double field of view having a size twice larger for each axis direction at the time of the separation;
the shifted signal correction unit further extracts an image corresponding to the field of view before the development from the measured image for every substance after the development; and
the reception unit at least comprises the receiver RF coils in a number of regions for the development and separation for every substance to be separated.

15. The magnetic resonance imaging apparatus according to claim 14, wherein
the sensitivity maps used by the separation unit include a sensitivity map of a standard substance determined beforehand by selecting it from the substances as the objects of measurement, and sensitivity maps of the other substances as the objects of measurement;
the sensitivity map of the standard substance is created by shifting the sensitivity map of the receiver RF coil of the double field of view created beforehand according to the shift amount of the standard substance; and
the sensitivity maps of the other substances as the objects of measurement are created as sensitivity maps of a double field of view in a number of types of the other substance as the objects of measurement by extracting the sensitivity map of the field of view from the sensitivity map of the standard substance, shifting the extracted sensitivity map according to the relative shift amount of each substance as the object of measurement based on the shift amount of the standard substance, and then performing 0 padding.

* * * * *